(12) United States Patent
Ochiiwa et al.

(10) Patent No.: US 10,894,048 B2
(45) Date of Patent: Jan. 19, 2021

(54) ANTITUMOR DRUG FOR INTERMITTENT ADMINISTRATION OF FGFR INHIBITOR

(71) Applicant: Taiho Pharmaceutical Co., Ltd., Tokyo (JP)

(72) Inventors: Hiroaki Ochiiwa, Tsukuba (JP); Hiroshi Hirai, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 16/274,573

(22) Filed: Feb. 13, 2019

(65) Prior Publication Data
US 2019/0183897 A1 Jun. 20, 2019

Related U.S. Application Data

(63) Continuation of application No. 14/905,420, filed as application No. PCT/JP2014/069086 on Jul. 17, 2014, now abandoned.

(30) Foreign Application Priority Data

Jul. 18, 2013 (JP) ................. 2013-149963

(51) Int. Cl.
| A61K 31/519 | (2006.01) |
| C07D 487/04 | (2006.01) |
| A61K 31/437 | (2006.01) |
| A61K 31/5377 | (2006.01) |

(52) U.S. Cl.
CPC .......... *A61K 31/519* (2013.01); *A61K 31/437* (2013.01); *A61K 31/5377* (2013.01); *C07D 487/04* (2013.01)

(58) Field of Classification Search
CPC ............... A61K 31/519; A61K 31/437; A61K 31/5377; C07D 487/04
See application file for complete search history.

(56) References Cited

U.S. PATENT DOCUMENTS

| 2009/0318468 | A1 | 12/2009 | Buttar et al. |
| 2012/0101064 | A1 | 4/2012 | Howard et al. |
| 2013/0061403 | A1 | 3/2013 | Bringewatt et al. |
| 2013/0158000 | A1 | 6/2013 | Brohm et al. |
| 2014/0005185 | A1 | 1/2014 | Nakamura et al. |
| 2014/0343035 | A1 | 11/2014 | Sagara et al. |
| 2015/0031676 | A1 | 1/2015 | Lobell et al. |
| 2015/0164909 | A1 | 6/2015 | Ichikawa et al. |
| 2015/0166544 | A1 | 6/2015 | Zhang et al. |
| 2016/0102366 | A1 | 4/2016 | Abe et al. |
| 2016/0136168 | A1 | 5/2016 | Sootome |
| 2016/0193210 | A1 | 7/2016 | Ochiiwa et al. |
| 2016/0287699 | A1 | 10/2016 | Karkera et al. |
| 2017/0035773 | A1 | 2/2017 | Tomimatsu et al. |
| 2017/0112894 | A1 | 4/2017 | Kawabe |
| 2017/0252317 | A1 | 9/2017 | Lyssikatos et al. |
| 2018/0030067 | A1 | 2/2018 | Hashimoto |
| 2018/0177788 | A1 | 6/2018 | Pachter et al. |

FOREIGN PATENT DOCUMENTS

| CN | 105859721 A | 8/2016 |
| EA | 201101566 A1 | 5/2012 |
| EP | 3138842 A1 | 3/2017 |
| EP | 3279202 A1 | 2/2018 |
| JP | 2011-524888 A | 9/2011 |
| JP | 2015500307 A | 1/2015 |
| JP | 2015508087 A | 3/2015 |
| JP | 2015-527339 A | 9/2015 |
| JP | 2016-104762 A | 6/2016 |
| JP | 2017-518276 A | 7/2017 |
| JP | 2018511611 A | 4/2018 |
| JP | 2018519327 A | 7/2018 |
| JP | 2018537420 A | 12/2018 |
| RU | 20098127883 A | 7/2009 |
| RU | 2428421 C2 | 12/2009 |
| WO | 2007/041712 A1 | 4/2007 |
| WO | 2007/087395 A2 | 8/2007 |
| WO | 2008077557 A1 | 7/2008 |
| WO | 2008/121742 A2 | 10/2008 |
| WO | 2010/043865 A1 | 4/2010 |
| WO | 2011/093672 A2 | 8/2011 |

(Continued)

OTHER PUBLICATIONS

Li et al. (Bioorg. Med. Chem. Lett. 21 (2011) 3637-3640, S1-527).*
Kubinyi (3D QSAR in Drug Design: Ligand-Protein Interactions and Molecular Similarity, vol. 2-3, Springer, 1998, 800 pages) pp. 243-244 provided.*
Wermuth, The Practice of Medicinal Chemsitry, 2d ed. (2003), 768 pages. Chs. 9-10 provided.*
Decision of Refusal for the corresponding JP patent application No. 2017-149671, dated May 2018.
Lectures of Experimental Chemistry (continued) 2 Separation and purification, 1967, pp. 159-162, 184-193.
Handbook of Solvents, 1985, pp. 47-51.
Version 4 Lectures on experimental chemistry 1 Basic operation I, 1990, pp. 184-189.
Impurities: Guideline for Residual Solvents, 1998, No. 307, pp. 1-11.

(Continued)

*Primary Examiner* — Robert H Havlin
(74) *Attorney, Agent, or Firm* — Rothwell, Figg, Ernst & Manbeck, P.C.

(57) ABSTRACT

The problems to be solved by the present invention are to provide a novel FGFR inhibitor that is potent and highly selective, and to provide an antitumor agent with which side effects such as an elevated blood phosphorus concentration are alleviated while maintaining the antitumor effect of the FGFR inhibitor. The present invention provides an antitumor agent comprising a 3,5-di-substituted benzene alkynyl compound represented by general formula (I) or salt thereof, which is used by administering the 3,5-di-substituted benzene alkynyl compound or salt thereof according to an administration schedule of two or more times/week at an administration interval of at least one day between doses.

18 Claims, 6 Drawing Sheets

(56) References Cited

FOREIGN PATENT DOCUMENTS

| WO | 2011/115937 A1 | 9/2011 |
|---|---|---|
| WO | 2011/153514 A2 | 12/2011 |
| WO | 2012/137870 A1 | 10/2012 |
| WO | 2013/108809 A1 | 7/2013 |
| WO | 2014007217 A1 | 1/2014 |
| WO | 2014/138364 A2 | 9/2014 |
| WO | 2014/172644 A2 | 10/2014 |
| WO | 2014203959 A1 | 12/2014 |
| WO | 2015/008839 A1 | 1/2015 |
| WO | 2015/008844 A1 | 1/2015 |
| WO | 2016136928 A1 | 9/2016 |
| WO | 2016/159327 A1 | 10/2016 |
| WO | 2017/150725 A1 | 9/2017 |

OTHER PUBLICATIONS

Office Action dated Apr. 24, 2017 for the corresponding RU patent application No. 2017134584, 15 pages.

Jonker et al., (Annals of Oncology 22: 1413-1419, 2011).

Gangjee et al., "Synthesis of 5,7-disubstituted-4-methyl-7H-pyrrolo[2,3-d]pyrimidin-2-amines as microtubule inhibitors", Bioorganic Medical Chemistry, 2013, vol. 21, No. 5, pp. 1180-1189.

Nakatsuru et al., "Significant in vivo Antitumor Activity by a Highly Potent, irreversible FGFR inhibitor, TAS-2985", European Journal of Cancer, 2012, vol. 48, Suppl.6, p. 117, 383.

Hernandez et al., "Prospective Study of FGFR3 Mutations as a Prognostic Factor in Nonmuscle invasive Urothelial Bladder Carcinomas", Journal of Clinical Oncology, 2006, vol. 24, No. 22, pp. 3664-3671.

Gelsi-Boyer et al., "Comprehensive Profiling of 8p11-12 Amplification in Breast Cancer", Molecular Cancer Research, 2005, vol. 3, No. 12, pp. 655-667.

Turner et al., "FGFR1 Amplification Drives Endocrine Therapy Resistance and is a Therapeutic Target in Breast Cancer", Cancer Research, 2010, vol. 70, No. 5, pp. 2085-2094.

Fukumoto et al., "FGF23 is a hormone-regulating phosphate metabolism—Unique biological characteristics of FGF23", Bone, 2007, vol. 40, pp. 1190-1195.

Shimada et al., "Targeted ablation of FgF23 demonstrates an essential physiological role of FGF23 in phosphate and vitamin D metabolism", Journal of Clinical Investigation., 2004, vol. 113, No. 4, pp. 561-568.

Razzaque et al., "FGF-23, vitamin D and calcification: the unholy triad", Nephrol. Dial. Transplant., 2005, vol. 20, pp. 2032-2035.

Office Action for the corresponding RU patent application No. 2016105133, dated Feb. 27, 2018.

Folkman, "Angiogenesis in cancer, vascular, rheumatoid and other diseases", Nature Medicine, 1995, vol. 1, No. 1, pp. 27-31.

Lieu et al., "Beyond VEGF: Inhibition of the fibroblast growth factor pathway and antiangiogenesis", Clinical Cancer Research, 2011, vol. 17, No. 19, pp. 6130-6139.

Gong et al., "A novel 3-arylethynyl-substituted pyrido[2,3-b]pyrazine derivatives and pharmacophore model as Wnt2/β-catenin pathway inhibitors in a non-small-cell lung cancer cell lines", Bioorganic &Medicinal Chemistry, vol. 19, 2011, pp. 5639-5647.

Yuki Kagobutsu Kessho Sakusei Handbook—Genri to Know-how-, Maruzen Co., Ltd., 2008, pp. 57-84 (See RU Office Action for a concise explanation).

Office Action for the JP patent application No. 2016-566309, dated Feb. 2, 2017.

Byrn et al., "Pharmaceutical Solids: A Strategic Approach to Regulatory Considerations", Pharmaceutical Research, 1995, 12(7), pp. 945-954.

Keiko Toyo Seizai no Sekkei to Hyoka, Kabushiki Kaisha Yakugyo Jihosha, 1995, pp. 76-79, 171-172 (See RU Office Action for a concise explanation).

Wilson et al., "Widespread potential for growth-factor-driven resistance to anticancer kinase inhibitors", Nature, 2012, 487(7408): 505-509.

Xie et al., "FGFR2 Gene Amplification in Gastric Cancer Predicts Sensitivity to the Selective FGFR Inhibitor AZD4547", Clinical Cancer Research, 2013, vol. 19, No. 9 pp. 2572-2583.

Chang et al., "Multiple receptor tyrosine kinase activation attenuates therapeutic efficacy of the fibroblast growth factor receptor 2 inhibitor AZD4547 in FGFR2 amplified gastric cancer", Oncotarget, vol. 6, No. 4, 2014, pp. 2009-2022.

Kleespies et al., "Tyrosine kinase inhibitors and gemcitabine: New treatment options in pancreatic cancer?", Drug Resistance Updates, (9) 2006, pp. 1-18.

Byron et al., "Fibroblast growth factor receptor inhibition synergizes with paclitaxel and doxorubicin in endometrial cancer cells", International Journal of Gynecological Cancer, 2012, vol. 22, No. 9, pp. 1517-1526.

Bavin et al., "Polymorphism in Process Development", Chemistry & Industry, 1989, (16), pp. 527-529.

Sootome et al., "Indentification and Biological Characterization of a Highly Potent, Irreversible Inhibitor of FGFR, TAS-2985", European Journal of Cancer, 48:116, Nov. 2012.

Nakatsuru et al., "Significant in Vivo Antitumor Activity by a Highly Potent, Irreversible FGFR Inhibitor, TAS-2985", European Journal of Cancer, Nov. 2012, vol. 48, Suppl. 6, pp. 117.

Machine Translation of WO2013108809 (published Jul. 25, 2013).

Pharmacodia (http:/en.pharmacodia.com/web/drug1_1258.html, retrieved Jun. 10, 2017).

Cayman (https://www.caymachem.com/product/21136, retrieved Jun. 10, 2017).

Byron et al., "The N550K/H Mutations in FGFR2 Confer Differential Resistance to PD173074, Dovitinib, and Ponatinib ATP-Competitive Inhibitors", Neoplasia, vol. 15, No. 8, pp. 975-988, 2013.

Konecny et al., "Activity of the Fibroblast Growth Factor Receptor Inhibitors Dovitinib (TK1258) and NVP-BGJ398 in Human Endometrial Cancer Cells", Molecular Cancer Therapeutics, 12(5), pp. 632-642, 2013.

Office Action dated Jun. 26, 2019 cited in U.S. Appl. No. 16/149,522, 19 pages.

Formisano et al., "Association of FGFR1 with Eralpha Maintains ligands—Independent ER Transcription and Mediates Resistance to Estrogen Deprevation in ER+ Breast Cancer", Clinical Cancer Research, 2017, vol. 23, Issue 20, pp. 3138-6150.

Sobhani et al., "Current Status of Fibroblast Growth Factor Receptor-Targeted Therapies in Breast Cancer", cells. 2018, vol. 7, Issue 7, Art. No. 76, pp. 1-14.

Andre, "Rationale for targeting fibroblast growth factor receptor signaling in breast cancer", Breast Cancer Research end Treatment, 2015, vol. 150, Issue 1, pp. 1-8.

Chae, "Inhibition of the fibroblast growth factor receptor (FGFR) pathway: the current landscape and barriers to clinical application", Oncotarget, 2017, vol. 8, No. 9, pp. 16052-16074.

Perez-Garcia et al., "Targeting FGFR pathway in breast cancer", The Breast, 2018, vol. 37, pp. 126-133.

Musolino et al., "Phase II, randomized placebo-controlled study of dovitinib in combination with fulvestrant in postmenopausal patients with HR+, HER2-breast cancer that had progressed during or after prior endocrine therapy", Breast Cancer Research, 2017, vol. 19, Art. No. 18, pp. 1-14.

Patani et al., "Landscape of activating cancer mutations in FGFR kinases and their differential responses to inhibitors in clinical use", Oncotarget, 2016, vol. 7, No. 17, pp. 24252-24268.

Singh et al., "Transforming Fusions of FGFR and TACC Genes in Human Glioblastoma", Science, 2012, vol. 337, pp. 1231-1235.

Brown et al., "Maximising the potential of AKT inhibitors as anti-cancer treatments", Pharmacology & Therapeutics, 2017, vol. 172, pp. 101-115.

Yunokawa et al., "First-in-human phase I study of TAS-117, an allosteric AKT inhibitor, in patients with advanced solid tumours", Annals of Oncology, 2019, vol. 30, Suppl. 5, p. v169.

(56) References Cited

OTHER PUBLICATIONS

Borad et al., "Fibroblast growth factor receptor 2 fusions as a target for treating cholangiocarcinoma", Curr Opin Gastroenterol, 2015, vol. 31(3), pp. 264-268.
Official Action of RU Pat. Appln. No. 2018134777, dated Jun. 1, 2020, 22 pages.
Caira M R, "Crystalline Polymorphism of Organic Compounds", Topics in Current Chemistry, 1998, vol. 198, pp. 163-208.
Office Action dated Feb. 5, 2019 for the corresponding MX patent application No. MX/a/2017/012568, 9 pages.

\* cited by examiner

→×— Control
→●— 15 mg/kg/day daily administration (Days 1-14)
→■— 30 mg/kg/day daily administration (Days 1-8)
→▲— 30 mg/kg/day intermittent administration (Days 1, 3, 5, 7, 9, 11, 13)
→◆— 100 mg/kg/day intermittent administration (Days 1, 4, 8, 11)

→×— Control
→◆— 15 mg/kg/day daily administration (Days 1-14)
→■— 30 mg/kg/day daily administration (Days 1-8)
→▲— 30 mg/kg/day intermittent administration (Days 1, 3, 5, 7, 9, 11, 13)
→◇— 30 mg/kg/day intermittent administration (Days 1, 4, 8, 11)
→◆— 100 mg/kg/day intermittent administration (Days 1, 4, 8, 11)

→×— Control
→●— 3 mg/kg/day daily administration (Days 1-14)
→▲— 30 mg/kg/day intermittent administration (Days 1, 3, 5, 7, 9, 11, 13)
→◆— 100 mg/kg/day intermittent administration (Days 1, 5, 8, 12)

─✕─ Control
─●─ 100 mg/kg/day daily administration (Days 1-14)
─▲─ 350 mg/kg/day intermittent administration (Days 1, 4, 8, 11)
─◆─ 700 mg/kg/day intermittent administration (Days 1, 8)

ANTITUMOR DRUG FOR INTERMITTENT ADMINISTRATION OF FGFR INHIBITOR

CROSS-REFERENCE TO RELATED APPLICATION

This application is continuation of U.S. Ser. No. 14/905,420 filed Jan. 15, 2016, which is a 35 U.S.C. 371 National Phase Entry application from PCT/JP2014/069086, filed Jul. 17, 2014, which claims the benefit of Japanese Patent Application No. 2013-149963 filed on Jul. 18, 2013, the entire contents of which are incorporated herein by reference.

TECHNICAL FIELD

The present invention relates to an antitumor agent comprising an FGFR inhibitor as an active ingredient and being intermittently administered.

BACKGROUND ART

Various types of cancer show aberrant signaling (overexpression, gene amplification, mutation, and translocation) of fibroblast growth factors (FGFs)/fibroblast growth factor receptors (FGFRs). Many reports have been made about the contribution of aberrant FGF/FGFR signaling to the growth, development, and prognosis of cancer (e.g., NPL 1, NPL 2, or NPL 3). Therefore, inhibition of this signaling pathway is considered to lead to suppression of the growth of cancer, and to contribute to provision of an effective and novel therapy for cancer patients. Meanwhile, it is reported that in the kidney, Klotho/FGFR1 and its ligand FGF23 play an important role in the control of serum phosphate level (NPL 4). It is suggested that due to dysfunction of Klotho/FGFR1-FGF23, the reabsorption of phosphorus in the kidney increases, resulting in an increase in blood phosphorus levels, and subsequent calcification caused thereby (NPL 5 or NPL 6).

CITATION LIST

Non-Patent Literature

NPL 1: J. Clin. Oncol. 24, 3664-3671 (2006)
NPL 2: Mol. Cancer Res. 3, 655-667 (2005)
NPL 3: Cancer Res. 70, 2085-2094 (2010)
NPL 4: Bone. 40, 1190-1195 (2007)
NPL 5: J Clin Invest. 113, 561-568 (2004)
NPL 6: Nephrol Dial Transplant. 20, 2032-2035 (2005)

SUMMARY OF INVENTION

Technical Problem

The problem to be solved by the present invention is to provide a potent and highly selective novel FGFR inhibitor, and an antitumor agent having reduced side effects, such as weight loss and increased blood phosphorus levels, while maintaining the antitumor effect of the FGFR inhibitor.

Solution to Problem

The present inventors conducted extensive studies, and consequently found that an increase in blood phosphorus levels can be significantly suppressed when a specific 3,5-disubstituted benzene alkynyl compound or a salt thereof is intermittently administered on an administration schedule of a dosing interval of at least one day. The present invention is based on this novel finding.

Therefore, the present invention provides the following items:

Item 1. An antitumor agent comprising a 3,5-disubstituted benzene alkynyl compound or a salt thereof that is used so that the 3,5-disubstituted benzene alkynyl compound or a salt thereof is administered on an administration schedule of at least twice a week and a dosing interval of at least one day, the 3,5-disubstituted benzene alkynyl compound being represented by Formula (I):

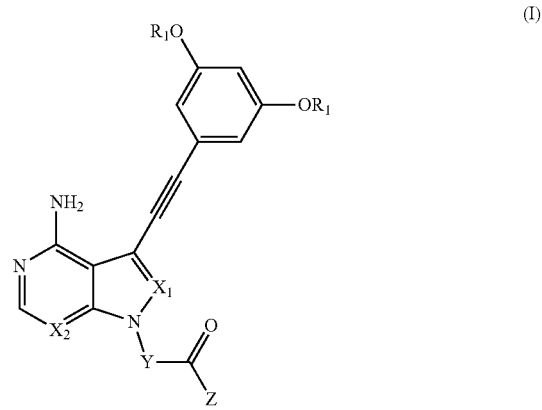

(I)

wherein $R_1$ is the same or different, and each represents $C_1$-$C_6$ alkyl;
$X_1$ and $X_2$ independently represent N or CH;
Y is a group represented by Formula (A):

(A)

wherein the divalent moiety represented by

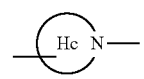

is a nitrogen-containing $C_3$-$C_{10}$ heterocycloalkylene group, a group represented by Formula (B):

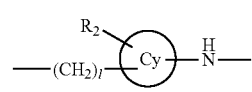

(B)

wherein the divalent moiety represented by

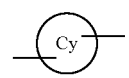

is a $C_3$-$C_{10}$ cycloalkylene group, or a group represented by Formula (C):

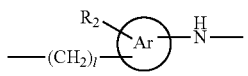

wherein the divalent moiety represented by

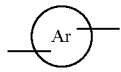

is a $C_6$-$C_{12}$ arylene group;

$R_2$ is hydrogen, $C_2$-$C_6$ alkynyl, —C(=O)$OR_x$, —C(=O)N($R_x$)($R_y$), hydroxy-$C_1$-$C_6$ alkyl, di($C_1$-$C_6$ alkyl)amino-$C_1$-$C_6$ alkyl, or $C_2$-$C_9$ heteroaryl optionally having $R_3$; and $R_3$ is $C_1$-$C_6$ alkyl or di($C_1$-$C_6$ alkyl)amino-$C_1$-$C_6$ alkyl;

Z is —C($R_4$)=C($R_5$)($R_6$) or —C≡C—$R_7$;

$R_4$, $R_5$, and $R_6$ are the same or different, and each represents hydrogen, halogen, $C_1$-$C_6$ alkyl optionally having $R_8$, or a group represented by Formula (D):

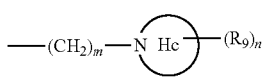

wherein the monovalent moiety represented by

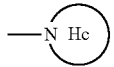

is a nitrogen-containing $C_3$-$C_{10}$ heterocycloalkyl group, $R_7$ is hydrogen, $C_1$-$C_6$ alkyl, or hydroxy-$C_1$-$C_6$ alkyl;

$R_8$ is —$OR_x$ or —N($R_x$)($R_y$);

$R_9$ is $C_1$-$C_6$ alkyl, halogen, or —$OR_x$;

$R_x$ and $R_y$ are the same or different, and each represents hydrogen, $C_1$-$C_6$ alkyl, $C_3$-$C_{10}$ cycloalkyl, di($C_1$-$C_6$ alkyl)amino-$C_1$-$C_6$ alkyl, or $C_1$-$C_6$ alkoxy-$C_1$-$C_6$ alkyl;

l is an integer of 0 to 3;

m is an integer of 1 to 3; and n is an integer of 0 to 2.

Item 2. A method for treating a cancer patient, the method comprising administering a 3,5-disubstituted benzene alkynyl compound represented by Formula (I) above, wherein $R_1$, $X_1$, $X_2$, Y, and Z are as defined above, or a salt thereof on an administration schedule of at least twice a week and a dosing interval of at least one day.

Item 3. A 3,5-disubstituted benzene alkynyl compound represented by Formula (I) above, wherein $R_1$, $X_1$, $X_2$, Y, and Z are as defined above, or a salt thereof for treatment of a cancer patient administered on an administration schedule of at least twice a week and a dosing interval of at least one day.

Item 4. Use of a 3,5-disubstituted benzene alkynyl compound represented by Formula (I) above, wherein $R_1$, $X_1$, $X_2$, Y, and Z are as defined above, or a salt thereof for producing an antitumor agent that is used so that the 3,5-disubstituted benzene alkynyl compound or a salt thereof is administered on an administration schedule of at least twice a week and a dosing interval of at least one day.

Item 5. The antitumor agent according to item 1, the method according to item 2, the compound or a salt thereof according to item 3, or the use according to item 4, wherein in Formula (I), (1) when $X_2$ is N, $X_1$ is N or CH, and (2) when $X_2$ is CH, $X_1$ is CH.

Item 6. The antitumor agent, method, compound or a salt thereof, or use according to any one of items 1 to 5, wherein in Formula (I), l is 0 or 1.

Item 7. The antitumor agent, method, compound or a salt thereof, or use according to any one of items 1 to 6, wherein in Formula (I), (1) when Y is a group represented by Formula (A), the group represented by

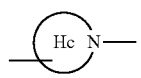

is azetidinylene, pyrrolidinylene, piperidinylene, piperazinylene, or morpholinylene, (2) when Y is a group represented by Formula (B), the group represented by

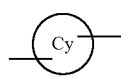

is cyclopropylene or cyclobutylene, and (3) when Y is a group represented by Formula (C), the group represented by

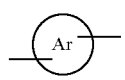

is phenylene.

Item 8. The antitumor agent, method, compound or a salt thereof, or use according to any one of items 1 to 7, wherein in Formula (I), (1) when Y is a group represented by Formula (A), Z is —C($R_4$)=C($R_5$)($R_6$) or —C≡C—$R_7$, and (2) when Y is a group represented by Formula (B) or (C), Z is —C($R_4$)=C($R_5$)($R_6$).

Item 9. The antitumor agent, method, compound or a salt thereof, or use according to any one of items 1 to 8, wherein in Formula (I), $R_1$ is methyl or ethyl.

Item 10. The antitumor agent, method, compound or a salt thereof, or use according to any one of items 1 to 9, wherein in Formula (I), $R_2$ is $C_2$-$C_6$ alkynyl, —C(=O)$OR_x$, hydroxy-$C_1$-$C_4$ alkyl, or $C_2$-$C_9$ heteroaryl optionally having $R_3$.

Item 11. The antitumor agent, method, compound or a salt thereof, or use according to any one of items 1 to 10, wherein the 3,5-disubstituted benzene alkynyl compound is selected from the following group of compounds:

(1) (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one, (2) (S)-1-(3-(4-amino-3-((3,5-dimethoxyphenyl)ethynyl)-1H-pyrazolo[3,4-d]pyrimidin-1-yl)pyrrolidin-1-yl)prop-2-yn-1-one, (3) (S)-1-(3-(4-amino-3-((3,5-diethoxyphenyl)ethynyl)-1H-pyrazolo[3,4-d]pyrimidin-1-yl)pyrrolidin-1-yl)prop-2-en-1-one, (4) 1-(3-(4-amino-3-((3,5-dimethoxyphenyl)ethynyl)-1H-pyrazolo[3,4-d]pyrimidin-1-yl)azetidin-1-yl)prop-2-en-1-one, (5) 1-(3-(4-amino-3-((3,5-dimethoxyphenyl)ethynyl)-1H-pyrazolo[3,4-d]pyrimidin-1-yl)azetidin-1-yl)-4-hydroxybut-2-yn-1-one,
(6) 1-(3-(4-amino-3-((3,5-dimethoxyphenyl)ethynyl)-1H-pyrazolo[3,4-d]pyrimidin-1-yl)azetidin-1-yl)-4-(dimethylamino)but-2-en-1-one,
(7) 1-(3-(4-amino-3-((3,5-dimethoxyphenyl)ethynyl)-1H-pyrazolo[3,4-d]pyrimidin-1-yl)azetidin-1-yl)-4-(cyclopropylamino)but-2-en-1-one,
(8) 1-(3-(4-amino-3-((3,5-dimethoxyphenyl)ethynyl)-1H-pyrazolo[3,4-d]pyrimidin-1-yl)azetidin-1-yl)-4-(isopropylamino)but-2-en-1-one,
(9) 1-(3-(4-amino-3-((3,5-dimethoxyphenyl)ethynyl)-1H-pyrazolo[3,4-d]pyrimidin-1-yl)azetidin-1-yl)-4-(ethyl(methyl)amino)but-2-en-1-one,
(10) 1-(3-(4-amino-3-((3,5-dimethoxyphenyl)ethynyl)-1H-pyrazolo[3,4-d]pyrimidin-1-yl)azetidin-1-yl)-4-(cyclobutylamino)but-2-en-1-one,
(11) 1-(3-(4-amino-3-((3,5-dimethoxyphenyl)ethynyl)-1H-pyrazolo[3,4-d]pyrimidin-1-yl)azetidin-1-yl)-4-(diethylamino)but-2-en-1-one,
(12) 1-(3-(4-amino-3-((3,5-dimethoxyphenyl)ethynyl)-1H-pyrazolo[3,4-d]pyrimidin-1-yl)azetidin-1-yl)-4-(tert-butylamino)but-2-en-1-one,
(13) 1-(3-(4-amino-3-((3,5-dimethoxyphenyl)ethynyl)-1H-pyrazolo[3,4-d]pyrimidin-1-yl)azetidin-1-yl)-4-(isopropyl(methyl)amino)but-2-en-1-one,
(14) 1-(3-(4-amino-3-((3,5-dimethoxyphenyl)ethynyl)-1H-pyrazolo[3,4-d]pyrimidin-1-yl)azetidin-1-yl)-4-(piperidin-1-yl)but-2-en-1-one,
(15) (S)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one,
(16) (R)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one,
(17) 1-((2S,4S)-4-(4-amino-3-((3,5-dimethoxyphenyl)ethynyl)-1H-pyrazolo[3,4-d]pyrimidin-1-yl)-2-(hydroxymethyl)pyrrolidin-1-yl)prop-2-en-1-one,
(18) 1-(2S,4S)-4-(4-amino-3-((3,5-dimethoxyphenyl)ethynyl)-1H-pyrazolo[3,4-d]pyrimidin-1-yl)-2-ethynylpyrrolidin-1-yl)prop-2-en-1-one,
(19) (S)-1-(3-(4-amino-5-((3,5-dimethoxyphenyl)ethynyl)-7H-pyrrolo[2,3-d]pyrimidin-7-yl)pyrrolidin-1-yl)-4-(dimethylamino)but-2-en-1-one,
(20) (S)-1-(3-(4-amino-5-((3,5-dimethoxyphenyl)ethynyl)-7H-pyrrolo[2,3-d]pyrimidin-7-yl)pyrrolidin-1-yl)prop-2-en-1-one,
(21) (S)-1-(3-(4-amino-5-((3,5-dimethoxyphenyl)ethynyl)-7H-pyrrolo[2,3-d]pyrimidin-7-yl)pyrrolidin-1-yl)-4-(pyrrolidin-1-yl)but-2-en-1-one,
(22) (S)-1-(3-(4-amino-5-((3,5-dimethoxyphenyl)ethynyl)-7H-pyrrolo[2,3-d]pyrimidin-7-yl)pyrrolidin-1-yl)-4-(4-hydroxypiperidin-1-yl)but-2-en-1-one,
(23) (S)-1-(3-(4-amino-5-((3,5-dimethoxyphenyl)ethynyl)-7H-pyrrolo[2,3-d]pyrimidin-7-yl)pyrrolidin-1-yl)but-2-yn-1-one,
(24) (S)-1-(3-(4-amino-5-((3,5-dimethoxyphenyl)ethynyl)-7H-pyrrolo[2,3-d]pyrimidin-7-yl)pyrrolidin-1-yl)-4-hydroxy-4-methylpent-2-yn-1-one,
(25) 1-((S)-3-(4-amino-5-((3,5-dimethoxyphenyl)ethynyl)-7H-pyrrolo[2,3-d]pyrimidin-7-yl)pyrrolidin-1-yl)-4-((S)-3-fluoropyrrolidin-1-yl)but-2-en-1-one,
(26) (S)-1-(3-(4-amino-5-((3,5-dimethoxyphenyl)ethynyl)-7H-pyrrolo[2,3-d]pyrimidin-7-yl)pyrrolidin-1-yl)-4-(piperidin-1-yl)but-2-en-1-one,
(27) 1-(3-(4-amino-5-((3,5-dimethoxyphenyl)ethynyl)-7H-pyrrolo[2,3-d]pyrimidin-7-yl)azetidin-1-yl)prop-2-en-1-one,
(28) 1-(3-(4-amino-5-((3,5-dimethoxyphenyl)ethynyl)-7H-pyrrolo[2,3-d]pyrimidin-7-yl)azetidin-1-yl)-4-(dimethylamino)but-2-en-1-one,
(29) 1-(3-(4-amino-5-((3,5-dimethoxyphenyl)ethynyl)-7H-pyrrolo[2,3-d]pyrimidin-7-yl)azetidin-1-yl)-4-(pyrrolidin-1-yl)but-2-en-1-one,
(30) 1-(3-(4-amino-5-((3,5-dimethoxyphenyl)ethynyl)-7H-pyrrolo[2,3-d]pyrimidin-7-yl)azetidin-1-yl)-4-(azetidin-1-yl)but-2-en-1-one,
(31) 1-(3-(4-amino-5-((3,5-dimethoxyphenyl)ethynyl)-7H-pyrrolo[2,3-d]pyrimidin-7-yl)azetidin-1-yl)-4-(ethyl(methyl)amino)but-2-en-1-one,
(32) 1-(3-(4-amino-5-((3,5-dimethoxyphenyl)ethynyl)-7H-pyrrolo[2,3-d]pyrimidin-7-yl)azetidin-1-yl)-4-(isopropylamino)but-2-en-1-one,
(33) 1-(3-(4-amino-5-((3,5-dimethoxyphenyl)ethynyl)-7H-pyrrolo[2,3-d]pyrimidin-7-yl)azetidin-1-yl)-4-(diethylamino)but-2-en-1-one,
(34) 1-(3-(4-amino-5-((3,5-dimethoxyphenyl)ethynyl)-7H-pyrrolo[2,3-d]pyrimidin-7-yl)azetidin-1-yl)-4-((2-methoxyethyl)(methyl)amino)but-2-en-1-one,
(35) 1-(3-(4-amino-5-((3,5-dimethoxyphenyl)ethynyl)-7H-pyrrolo[2,3-d]pyrimidin-7-yl)azetidin-1-yl)-4-(4-hydroxypiperidin-1-yl)but-2-en-1-one,
(36) (S)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one,
(37) (R)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one,
(38) (2S,4S)-methyl-1-acryloyl-4-(4-amino-5-((3,5-dimethoxyphenyl)ethynyl)-7H-pyrrolo[2,3-d]pyrimidin-7-yl)pyrrolidine-2-carboxylate,
(39) 1-((2S,4S)-4-(4-amino-5-((3,5-dimethoxyphenyl)ethynyl)-7H-pyrrolo[2,3-d]pyrimidin-7-yl)-2-(1,3,4-oxadiazol-2-yl)pyrrolidin-1-yl)prop-2-en-1-one, and
(40) (S)-1-(3-(4-amino-3-((3,5-dimethoxyphenyl)ethynyl)-1H-pyrrolo[3,2-c]pyridin-1-yl)pyrrolidin-1-yl)prop-2-en-1-one.

Item 12. The antitumor agent, method, compound or a salt thereof, or use according to any one of items 1 to 11, wherein the 3,5-disubstituted benzene alkynyl compound is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one.

Item 13. The antitumor agent, method, compound or a salt thereof, or use according to any one of items 1 to 12, wherein the administration schedule is based on a 1-week cycle, in which the 3,5-disubstituted benzene alkynyl compound or a salt thereof is administered at least twice every one to three days per cycle, and this cycle is performed once or repeated twice or more.

Item 14. The antitumor agent, method, compound or a salt thereof, or use according to any one of items 1 to 13, wherein the administration schedule is based on a 14-day cycle, in which the 3,5-disubstituted benzene alkynyl compound or a salt thereof is administered 4 to 7 times every one to three days per cycle, and this cycle is performed once or repeated twice or more.

Item 15. The antitumor agent, method, compound or a salt thereof, or use according to any one of items 1 to 14, wherein the administration schedule is based on a 14-day cycle, in which among 14 days contained in one cycle, (S)-1-(3-(4-amino-3-((3,5-dimethoxyphenyl)ethynyl)-1H-pyrazolo[3,4- d]pyrimidin-1-yl)pyrrolidin-1-yl)prop-2-en-1-one or a salt thereof is administered on Day 1, Day 4, Day 8, and Day 11.

Item 16. The antitumor agent, method, compound or a salt thereof, or use according to any one of items 1 to 14, wherein the administration schedule is based on a 14-day cycle, in which among 14 days contained in one cycle, (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one or a salt thereof is administered on Day 1, Day 3, Day 5, Day 7, Day 9, Day 11, and Day 13.

Advantageous Effects of Invention

The 3,5-disubstituted benzene alkynyl compound or a salt thereof, which is the active ingredient of the present invention, has excellent FGFR inhibitory activity and exhibits cancer cell growth inhibitory effects. Accordingly, the compound or a salt thereof is useful as a preventive and/or therapeutic agent for cancer. Furthermore, the present invention provides an effective method for administering Compound (I) that inhibits FGFR, for exhibiting antitumor effects while reducing systemic toxicity expressed by a continuous increase in blood phosphorus levels and suppression of body weight gain observed when FGFR is inhibited. The maintenance of the effect and reduction of toxicity development lead to enhancement of therapeutic effects, and contribute to the benefit for cancer patients.

The present invention suggests that, compared with daily administration, administration at appropriate intervals (intermittent administration) can further increase the balance between the effects and toxicity of the FGFR inhibitor, leading to an improvement in treatment methods.

DESCRIPTION OF EMBODIMENTS

Figure 1:
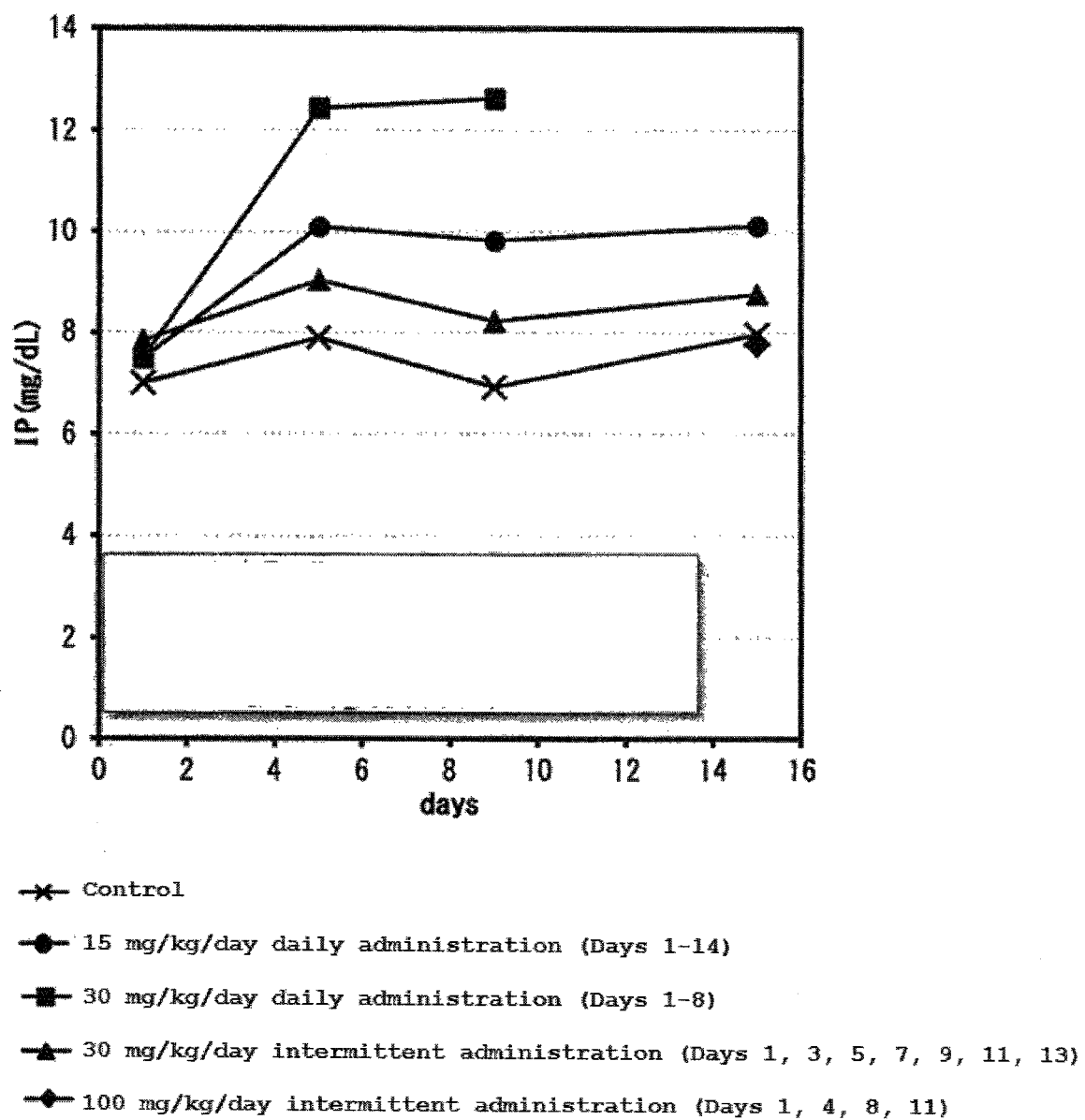
FIG. 1 shows the measurement results of blood phosphorus levels in Test Example 6.

The present invention provides an antitumor agent comprising a 3,5-disubstituted benzene alkynyl compound represented by Formula (I) above or a salt thereof that is used so that the 3,5-disubstituted benzene alkynyl compound or a salt thereof is administered on an administration schedule of at least twice a week and a dosing interval of at least one day. In the present specification, the compound represented by Formula (I), which is the active ingredient of the antitumor agent of the present invention, is also referred to simply as "Compound (I)."

The present invention exhibits an effect of reducing side effects, such as weight loss and increased blood phosphorus levels, while maintaining the antitumor effect, by using an administration schedule of at least twice a week and a dosing interval of at least one day.

In the present invention, the administration schedule is not particularly limited, as long as it satisfies the conditions of at least twice a week and a dosing interval of at least one day.

Examples of the administration schedule include:

an administration schedule based on a 1-week cycle, in which Compound (I) or a salt thereof is administered at least twice every one to three days per cycle, and this cycle is performed once or repeated twice or more;

an administration schedule based on a 14-day cycle, in which Compound (I) or a salt thereof is administered 4 to 7 times every one to three days per cycle, and this cycle is performed once or repeated twice or more;

an administration schedule based on a 14-day cycle, in which among 14 days contained in one cycle, Compound (I) or a salt thereof is administered on Day 1, Day 4, Day 8, and Day 11;

an administration schedule based on a 14-day cycle, in which among 14 days contained in one cycle, Compound (I) or a salt thereof is administered on Day 1, Day 3, Day 5, Day 7, Day 9, Day 11, and Day 13;

an administration schedule based on a 14-day cycle, in which among 14 days contained in one cycle, Compound (I) or a salt thereof is administered on Day 1, Day 3, Day 5, Day 8, Day 10, and Day 12;

and the like.

In the present invention, the administration "at least twice a week" means that the number of doses in each week is always two or more, rather than that the average number of doses per week obtained by dividing the total number of doses in the administration schedule by the whole period is two or more. For example, in a 4-week administration schedule, when administration is performed 3 times in the first week, 4 times in the second week, once in the third week, and once in the fourth week, administration is performed 9 times in four weeks. In this case, the average number of doses per week exceeds two; however, the number of doses in the third and fourth weeks is less than two. Therefore, this case does not satisfy the condition of the present invention, i.e., "administration at least twice a week" (except for a case where drug holidays, described below, are provided).

When the last week of the administration schedule does not include 7 days, the administration "at least twice a week" means that the number of doses in each week from the first week to the week before the last week is always two or more, and that the number of doses per week converted from the number of doses in the last week is two or more (e.g., one or more in two days, one or more in three days, two or more in four days, two or more in five days, and two or more in six days). When the last week includes only one day, the condition of the present invention, i.e., "at least twice a week," is satisfied as long as the number of doses in each week from the first week to the week before the last week is always two or more, regardless of whether administration is performed on the last day. Similarly, in the embodiment of an administration schedule based on a 14-day cycle, the last cycle does not necessarily include 14 days. In that case, it is sufficient that the number of doses for 14 days converted from the number of doses in the last cycle satisfies the condition of the present invention, as in the above case.

Moreover, in the administration schedule of the present invention, as long as the medication is continued on the schedule of at least twice a week and a dosing interval of at least one day for a certain period of time (e.g., 1 week or more, 10 days or more, or 14 days or more), the medication may be stopped thereafter, and the medication may be restarted after a certain period of drug holiday. Similarly, the administration schedule of the present invention includes a schedule having a plurality of drug holidays. In an embodiment having such a drug holiday, it is sufficient that the conditions "at least twice a week and a dosing interval of at least one day" are satisfied in the dosing period before the drug holiday and in the dosing period after the drug holiday. When two or more drug holidays are provided, it is sufficient that the conditions "at least twice a week and a dosing interval of at least one day" are satisfied in the dosing period before the first drug holiday, in the dosing period between the drug holidays, and in the dosing period after the second drug holiday. The period of drug holiday is not particularly limited, and can be suitably set according to the patient's state, etc. The period of drug holiday can be suitably set, for example, within the range of 1 to 35 days, preferably 1 to 14 days, and more preferably 1 to 7 days.

The compound represented by the above Formula (I), which is particularly preferable as the active ingredient of the antitumor agent of the present invention, is a 3,5-disubstituted benzene alkynyl compound containing a condensed heteroaryl group substituted for an α,β-unsaturated amide via a spacer moiety.

In the present specification, the term "$C_1$-$C_6$ alkyl" refers to a straight or branched alkyl group having 1 to 6 carbon atoms. Specific examples thereof include methyl, ethyl, n-propyl, isopropyl, n-butyl, isobutyl, sec-butyl, tert-butyl, pentyl, hexyl, and the like. The $C_1$-$C_6$ alkyl is preferably a straight or branched alkyl group having 1 to 4 carbon atoms (a $C_1$-$C_4$ alkyl group), and more preferably methyl, ethyl, isopropyl, and tert-butyl.

In this specification, the term "$C_3$-$C_{10}$ cycloalkyl" refers to a monocyclic or polycyclic cycloalkyl group having 3 to 10 carbon atoms, and is preferably a monocyclic cycloalkyl group having 3 to 6 carbon atoms (a $C_3$-$C_6$ cycloalkyl group). Specific examples thereof include cyclopropyl, cyclobutyl, cyclopentyl, cyclohexyl, cycloheptyl, decalyl, and the like. Cyclopropyl and cyclobutyl are preferable. In this specification, the divalent moiety represented by

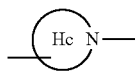

of the group represented by Formula (A)

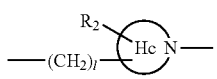

(A)

(wherein $R_2$ and l are as defined above)
is a $C_3$-$C_{10}$ divalent heterocycloalkylene group containing at least one nitrogen atom in the ring and further containing 0 to 2 same or different heteroatoms selected from oxygen and sulfur atoms in the ring (a nitrogen-containing $C_3$-$C_{10}$ heterocycloalkylene group), and is preferably a $C_3$-$C_5$ heterocycloalkylene group containing 1 to 3 nitrogen atoms in the ring and further containing 0 to 1 oxygen atom in the ring (a nitrogen-containing $C_3$-$C_5$ heterocycloalkylene group). Specific examples thereof include azetidinylene, pyrrolidinylene, piperidinylene, piperazinylene, morpholinylene, octahydroquinolinylene, octahydroindolylene, and the like. Among them, azetidinylene, pyrrolidinylene, piperidinylene, piperazinylene, and morpholinylene are preferable.

The group represented by Formula (A)

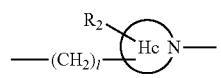

(A)

refers to a divalent nitrogen-containing $C_3$-$C_{10}$ heterocycloalkylene group represented by

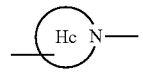

wherein the nitrogen atom has one arm and the other arm is connected to a substituent (—$(CH_2)_l$—), and a substituent $R_2$ is present on the ring.

In this specification, the divalent moiety represented by

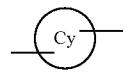

of the group represented by Formula (B)

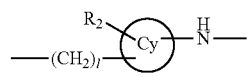

(B)

(wherein $R_2$ and l are as defined above)
refers to a monocyclic or polycyclic divalent cycloalkylene group having 3 to 10 carbon atoms (a $C_3$-$C_{10}$ cycloalkylene group), and preferably a monocyclic divalent cycloalkylene group having 3 to 6 carbon atoms (a $C_3$-$C_6$ cycloalkylene group). Specific examples thereof include cyclopropylene, cyclobutylene, cyclopentylene, cyclohexylene, cycloheptylene, decalylene, and the like. Cyclopropylene and (1,2- or 1,3-)cyclobutylene are preferable.

Formula (B)

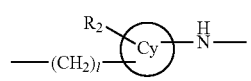

(B)

refers to a divalent $C_3$-$C_{10}$ cycloalkylene group represented by

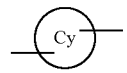

wherein one arm is connected to an adjacent amino group (NH) and the other arm is connected to a substituent (—$(CH_2)_l$—), and a substituent $R_2$ is present on the ring.

In the present specification, the divalent moiety represented by

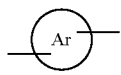

of the group represented by Formula (C)

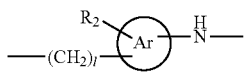

(wherein $R_2$ and $l$ are as defined above)
refers to a divalent arylene group having 6 to 12 carbon atoms (a $C_6$-$C_{12}$ arylene group). Specific examples thereof include phenylene, naphthylene, biphenylene, and the like. Phenylene is preferable.

Formula (C)

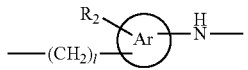

refers to a divalent $C_6$-$C_{12}$ arylene group represented by

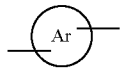

wherein one arm is connected to an adjacent amino group (NH) and the other arm is connected to a substituent (—$(CH_2)_l$—), and a substituent $R_2$ is present on the ring.

In this specification, the monovalent moiety represented by

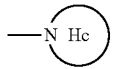

of the group represented by Formula (D)

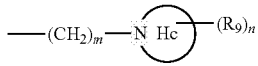

(wherein $R_9$, m, and n are as defined above)
refers to a $C_3$-$C_{10}$ heterocycloalkyl group containing at least one nitrogen atom in the ring and further containing 0 to 2 same or different heteroatoms selected from oxygen and sulfur atoms in the ring (a nitrogen-containing $C_3$-$C_{10}$ heterocycloalkyl group), and is preferably a $C_3$-$C_5$ heterocycloalkyl group containing 1 to 3 nitrogen atoms in the ring and further containing 0 to 1 oxygen atom in the ring (a nitrogen-containing $C_3$-$C_5$ heterocycloalkyl group). Specific examples thereof include azetidinyl, pyrrolidinyl, piperidinyl, piperazinyl, morpholinyl, octahydroquinolinyl, octahydroindolyl, and the like. Azetidinyl, pyrrolidinyl, piperidinyl, piperazinyl, and morpholinyl are preferable.

Formula (D)

denotes a nitrogen-containing $C_3$-$C_{10}$ heterocycloalkyl group represented by

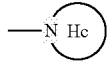

wherein the nitrogen atom is bound to a substituent (—$(CH_2)_m$—), and n substituents (—$(R_9)_n$) are present on the ring.

In this specification, the "$C_2$-$C_9$ heteroaryl" refers to a monocyclic or bicyclic $C_2$-$C_9$ heteroaryl group containing 1 to 3 same or different heteroatoms selected from nitrogen, oxygen, and sulfur atoms; and is preferably a monocyclic $C_2$-$C_5$ heteroaryl group containing 1 to 3 same or different heteroatoms selected from nitrogen, oxygen, and sulfur atoms (a $C_2$-$C_5$ heteroaryl group). Specific examples thereof include thienyl, furyl, pyrrolyl, triazolyl, imidazolyl, pyrazolyl, oxadiazolyl, isothiazolyl, isoxazolyl, pyridyl, pyrazinyl, pyrimidinyl, pyridazinyl, isobenzofuryl, indolizinyl, isoindolyl, indolyl, indazolyl, quinolyl, isoquinolyl, phthalazinyl, naphthyridinyl, and the like. 1,3,4-Oxadiazolyl is preferable.

In this specification, the term "$C_2$-$C_6$ alkynyl" refers to a straight or branched $C_2$-$C_6$ alkynyl group having at least one carbon-carbon triple bond. Specific examples thereof include ethynyl, 2-propynyl, 2-hexynyl, and the like. Ethynyl is preferable.

In this specification, the term "hydroxy-$C_1$-$C_6$ alkyl" refers to a straight or branched $C_1$-$C_6$ alkyl group having one hydroxy group. Specific examples thereof include hydroxymethyl, hydroxyethyl, hydroxypropyl, hydroxybutyl, hydroxypentyl, hydroxyhexyl, and the like. Among them, hydroxymethyl, 2-hydroxyethyl, 2-hydroxypropyl, and 2-hydroxybutyl are preferable.

In this specification, the term "di($C_1$-$C_6$ alkyl)amino-$C_1$-$C_6$ alkyl" refers to a straight or branched $C_1$-$C_6$ alkyl group having an amino group having two straight or branched $C_1$-$C_6$ alkyl groups. A straight or branched $C_1$-$C_4$ alkyl group having an amino group having two straight or branched $C_1$-$C_4$ alkyl groups (a di($C_1$-$C_4$ alkyl)amino-$C_1$-$C_4$ alkyl group) is preferable. Specific examples thereof include dimethylaminomethyl, dimethylaminoethyl, dimethylaminopropyl, dimethylaminobutyl, dimethylaminopentyl, dimethylaminohexyl, diethylaminomethyl, diethylaminoethyl, diethylaminopropyl, diethylaminobutyl, diethylaminopentyl, diethylaminohexyl, dipropylaminomethyl, dibutylaminomethyl, dipentylaminomethyl, dihexylaminomethyl, ethyl(methyl)aminomethyl, and the like. Dimethylaminomethyl and diethylaminomethyl are preferable.

In this specification, the term "$C_1$-$C_6$ alkoxy-$C_1$-$C_6$ alkyl" refers to a straight or branched $C_1$-$C_6$ alkyl group having a straight or branched $C_1$-$C_6$ alkoxy group. It is preferably a straight or branched $C_1$-$C_4$ alkyl group having a straight or branched $C_1$-$C_4$ alkoxy group (a $C_1$-$C_4$ alkoxy-$C_1$-$C_4$ alkyl group). Specific examples of such groups include methoxymethyl, methoxyethyl, methoxypropyl, methoxybutyl, methoxypentyl, methoxyhexyl, ethoxymethyl, ethoxyethyl, ethoxypropyl, ethoxybutyl, ethoxypentyl, ethoxyhexyl, propoxymethyl, butoxymethyl, pentyloxymethyl, hexyloxymethyl, and the like. Among them, 2-methoxyethyl is preferable.

In this specification, examples of the "halogen" include chlorine, bromine, fluorine, and iodine. Fluorine is preferable.

In Formula (I), the following combinations of $X_1$ and $X_2$ are preferable. (1) When $X_2$ is N, $X_1$ is N or CH. (2) When $X_2$ is CH, $X_1$ is CH.

In Formula (I), l is preferably 0 or 1.

In Formula (I), Y is preferably a group represented by Formula (A)

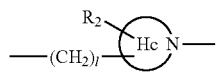
(A)

(wherein $R_2$ and l are as defined above) or a group represented by Formula (C)

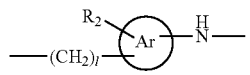
(C)

(wherein $R_2$ and l are as defined above). More preferably, the divalent moiety represented by

of a group represented by Formula (A) is pyrrolidinylene, azetidinylene, or piperidinylene, or the divalent moiety represented by

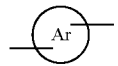

of a group represented by Formula (C) is phenylene.

In Formula (I), the following combinations of Y and Z are preferable. When Y is a group represented by Formula (A)

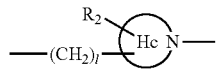
(A)

(wherein $R_2$ and l are as defined above), Z is —C($R_4$)═C($R_5$)($R_6$) or —C≡C—$R_7$. When Y is a group represented by Formula (B) or (C):

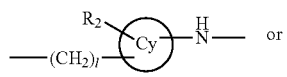
(B)

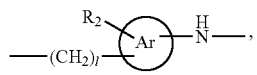
(C)

(wherein $R_2$ and l are as defined above), Z is —C($R_4$)═C($R_5$)($R_6$). In Formula (I), $R_1$ is preferably $C_1$-$C_4$ alkyl, and more preferably methyl or ethyl.

In Formula (I), $R_2$ is preferably hydrogen, $C_2$-$C_6$ alkynyl, —C(═O)O$R_x$, hydroxy-$C_1$-$C_4$ alkyl, or $C_2$-$C_9$ heteroaryl optionally having $R_3$, and more preferably ethynyl, methoxycarbonyl, hydroxymethyl, or 1,3,4-oxadiazolyl optionally having $R_3$.

In Formula (I), $R_3$ is preferably $C_1$-$C_4$ alkyl or di-($C_1$-$C_4$ alkyl)amino-$C_1$-$C_4$ alkyl, and more preferably methyl or dimethylaminomethyl.

In Formula (I), $R_4$ is preferably hydrogen or halogen, more preferably hydrogen or fluorine, and even more preferably hydrogen.

In Formula (I), $R_5$ and $R_6$ are preferably hydrogen, $C_1$-$C_4$ alkyl group optionally having $R_8$, or a group represented by Formula (D)

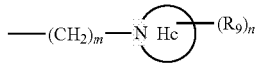
(D)

(wherein $R_9$, m and n are as defined above), and more preferably hydrogen, methyl having $R_8$, or a group represented by Formula (D)

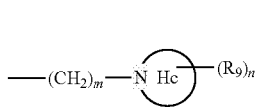
(D)

(wherein $R_9$, m, and n are as defined above).

In Formula (I), m is preferably 1.

In Formula (I), $R_9$ is preferably $C_1$-$C_4$ alkyl, fluorine, or hydroxy, and more preferably methyl, fluorine, or hydroxy.

In Formula (I), n is preferably 0 or 1.

In Formula (I), $R_7$ is preferably hydrogen, $C_1$-$C_4$ alkyl, or hydroxy-$C_1$-$C_4$ alkyl, and more preferably hydrogen, hydroxymethyl, methyl, or 2-hydroxy-2-methyl-ethyl.

In Formula (I), $R_8$ is preferably hydroxy or —N($R_x$)($R_y$). In this formula, $R_x$ and $R_y$ are preferably hydrogen, $C_1$-$C_4$ alkyl, $C_3$-$C_{10}$ cycloalkyl, or $C_1$-$C_4$ alkoxy-$C_1$-$C_4$ alkyl, and more preferably hydrogen, methyl, ethyl, tert-butyl, isopropyl, cyclopropyl, cyclobutyl, or 2-methoxyethyl.

Preferable Compounds (I) are compounds represented by Formula (I) wherein $R_1$ is $C_1$-$C_4$ alkyl; $X_1$ and $X_2$ are independently N or CH; Y is a group represented by Formula (A) or (C):

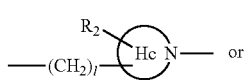
(A)

or

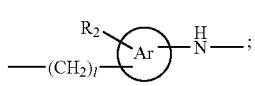
(C)

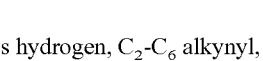

$R_2$ is hydrogen, $C_2$-$C_6$ alkynyl, —C(═O)O$R_x$, hydroxy-$C_1$-$C_4$ alkyl, or $C_2$-$C_9$ heteroaryl optionally having $R_3$; $R_3$ is $C_1$-$C_4$ alkyl or di($C_1$-$C_4$ alkyl)amino-$C_1$-$C_4$ alkyl; Z is —C($R_4$)═C($R_5$)($R_6$) or —C≡C—$R_7$; $R_4$ is hydrogen or halogen; $R_5$ and $R_6$ are the same or different, and each represents hydrogen, $C_1$-$C_4$ alkyl optionally having $R_8$, or a group represented by Formula (D)

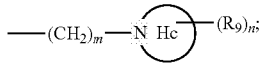
(D)

$R_7$ is hydrogen, $C_1$-$C_4$ alkyl, or hydroxy-$C_1$-$C_4$ alkyl; $R_8$ is hydroxy or —N($R_x$)($R_y$); $R_9$ is $C_1$-$C_4$ alkyl, fluorine, or hydroxy; $R_x$ and $R_y$ are the same or different, and each represents hydrogen, $C_1$-$C_4$ alkyl, $C_3$-$C_{10}$ cycloalkyl, or $C_1$-$C_4$ alkoxy-$C_1$-$C_4$ alkyl; and l is 0 or 1, m is 1, and n is 0 or 1.

More preferable Compounds (I) are compounds represented by Formula (I) wherein $R_1$ is $C_1$-$C_4$ alkyl; $X_1$ and $X_2$ are such that (1) when $X_2$ is N, $X_1$ is N or CH, and (2) when $X_2$ is CH, $X_1$ is CH; in Y, the divalent moiety represented by

of the group represented by Formula (A)

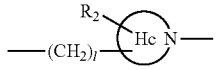
(A)

is pyrrolidinylene, azetidinylene, or piperidinylene, or the divalent moiety represented by

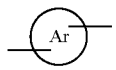

of the group represented by Formula (C)

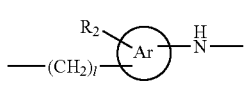
(C)

is phenylene;
(a) when Y is a group represented by Formula (A)

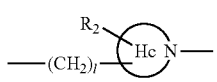
(A)

(wherein $R_2$ is hydrogen, ethynyl, methoxycarbonyl, hydroxymethyl, or 1,3,4-oxadiazolyl optionally having $R_3$; $R_3$ is $C_1$-$C_4$ alkyl; and l is 0 or 1), Z is —C($R_4$)=C($R_5$)($R_6$) or —C≡C—$R_7$, (b) when Y is a group represented by Formula (C)

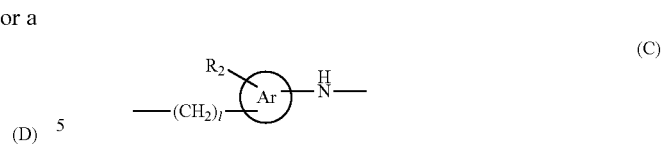
(C)

(wherein $R_2$ is hydrogen; and l is 0 or 1), Z is —C($R_4$)=C($R_5$)($R_6$);
$R_4$ is hydrogen or fluorine; $R_5$ and $R_6$ are the same or different, and each represents hydrogen, $C_1$-$C_4$ alkyl optionally having $R_8$, or a group represented by Formula (D)

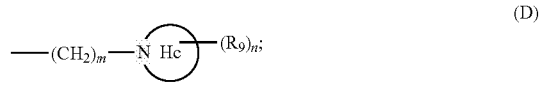
(D)

$R_7$ is hydrogen, hydroxymethyl, methyl, or 2-hydroxy-2-methyl-ethyl; $R_8$ is —N($R_x$)($R_y$); $R_9$ is $C_1$-$C_4$ alkyl, fluorine, or hydroxy; $R_x$ and $R_y$ are the same or different, and each represents hydrogen, $C_1$-$C_4$ alkyl, $C_3$-$C_{10}$ cycloalkyl, or $C_1$-$C_4$ alkoxy-$C_1$-$C_4$ alkyl, m is 1, and n is 0 or 1.

Even more preferable Compounds (I) are compounds represented by Formula (I) wherein $R_1$ is methyl or ethyl; $X_1$ and $X_2$ are such that (1) when $X_2$ is N, $X_1$ is N or CH, and (2) when $X_2$ is CH, $X_1$ is CH; in Y, the divalent moiety represented by

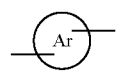

is pyrrolidinylene, azetidinylene, piperidinylene, or the divalent moiety represented by

is phenylene;
(a) when Y is a group represented by Formula (A)

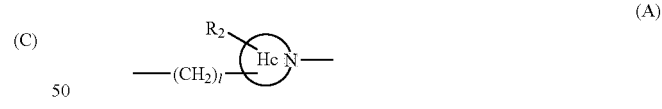
(A)

(wherein $R_2$ is hydrogen, ethynyl, methoxycarbonyl, hydroxymethyl, or 1,3,4-oxadiazolyl optionally having methyl; and l is 0 or 1), Z is —C($R_4$)=C($R_5$)($R_6$) or —C≡C—$R_7$, (b) when Y is a group represented by Formula (C)

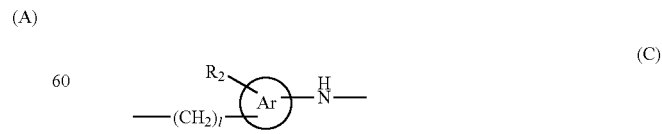
(C)

(wherein $R_2$ is hydrogen; and l is 1), Z is —C($R_4$)=C($R_5$)($R_6$); $R_4$ is hydrogen; $R_5$ and $R_6$ are the same or different, and each represents hydrogen, methyl having $R_8$, or the monovalent moiety represented by

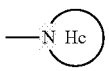

of the group represented by Formula (D)

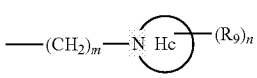

is pyrrolidinyl, piperidinyl, azetidinyl, piperazinyl, or morpholinyl; $R_7$ is hydrogen, hydroxymethyl, methyl, or 2-hydroxy-2-methyl-ethyl; $R_8$ is —$N(R_x)(R_y)$; $R_9$ is methyl, fluorine, or hydroxy and; $R_x$ and $R_y$ are the same or different, and each represents hydrogen, methyl, ethyl, tert-butyl, isopropyl, cyclopropyl, cyclobutyl, or 2-methoxyethyl; and m is 1, and n is 0 or 1.

Specific examples of preferable Compounds (I) include the following:

(1) (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one
(Compound of Example 2), (2) (S)-1-(3-(4-amino-3-((3,5-dimethoxyphenyl)ethynyl)-1H-pyrazolo[3,4-d]pyrimidin-1-yl)pyrrolidin-1-yl)prop-2-yn-1-one (Compound of Example 5), (3) (S)-1-(3-(4-amino-3-((3,5-diethoxyphenyl)ethynyl)-1H-pyrazolo[3,4-d]pyrimidin-1-yl)pyrrolidin-1-yl)prop-2-en-1-one (Compound of Example 8), (4) 1-(3-(4-amino-3-((3,5-dimethoxyphenyl)ethynyl)-1H-pyrazolo[3,4-d]pyrimidin-1-yl)azetidin-1-yl)prop-2-en-1-one (Compound of Example 9), (5) 1-(3-(4-amino-3-((3,5-dimethoxyphenyl)ethynyl)-1H-pyrazolo[3,4-d]pyrimidin-1-yl)azetidin-1-yl)-4-hydroxybut-2-yn-1-one (Compound of Example 10), (6) 1-(3-(4-amino-3-((3,5-dimethoxyphenyl)ethynyl)-1H-pyrazolo[3,4-d]pyrimidin-1-yl)azetidin-1-yl)-4-(dimethylamino)but-2-en-1-one (Compound of Example 12), (7) 1-(3-(4-amino-3-((3,5-dimethoxyphenyl)ethynyl)-1H-pyrazolo[3,4-d]pyrimidin-1-yl)azetidin-1-yl)-4-(cyclopropylamino)but-2-en-1-one (Compound of Example 13), (8) 1-(3-(4-amino-3-((3,5-dimethoxyphenyl)ethynyl)-1H-pyrazolo[3,4-d]pyrimidin-1-yl)azetidin-1-yl)-4-(isopropylamino)but-2-en-1-one (Compound of Example 14), (9) 1-(3-(4-amino-3-((3,5-dimethoxyphenyl)ethynyl)-1H-pyrazolo[3,4-d]pyrimidin-1-yl)azetidin-1-yl)-4-(ethyl(methyl)amino)but-2-en-1-one (Compound of Example 15),

(10) 1-(3-(4-amino-3-((3,5-dimethoxyphenyl)ethynyl)-1H-pyrazolo[3,4-d]pyrimidin-1-yl)azetidin-1-yl)-4-(cyclobutylamino)but-2-en-1-one (Compound of Example 16),

(11) 1-(3-(4-amino-3-((3,5-dimethoxyphenyl)ethynyl)-1H-pyrazolo[3,4-d]pyrimidin-1-yl)azetidin-1-yl)-4-(diethylamino)but-2-en-1-one (Compound of Example 17),

(12) 1-(3-(4-amino-3-((3,5-dimethoxyphenyl)ethynyl)-1H-pyrazolo[3,4-d]pyrimidin-1-yl)azetidin-1-yl)-4-(tert-butylamino)but-2-en-1-one (Compound of Example 18),

(13) 1-(3-(4-amino-3-((3,5-dimethoxyphenyl)ethynyl)-1H-pyrazolo[3,4-d]pyrimidin-1-yl)azetidin-1-yl)-4-(isopropyl(methyl)amino)but-2-en-1-one (Compound of Example 19),

(14) 1-(3-(4-amino-3-((3,5-dimethoxyphenyl)ethynyl)-1H-pyrazolo[3,4-d]pyrimidin-1-yl)azetidin-1-yl)-4-(piperidin-1-yl)but-2-en-1-one (Compound of Example 20),

(15) (S)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one (Compound of Example 22),

(16) (R)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one (Compound of Example 23),

(17) 1-((2S,4S)-4-(4-amino-3-((3,5-dimethoxyphenyl)ethynyl)-1H-pyrazolo[3,4-d]pyrimidin-1-yl)-2-(hydroxymethyl)pyrrolidin-1-yl)prop-2-en-1-one (Compound of Example 28),

(18) 1-(2S,4S)-4-(4-amino-3-((3,5-dimethoxyphenyl)ethynyl)-1H-pyrazolo[3,4-d]pyrimidin-1-yl)-2-ethynylpyrrolidin-1-yl)prop-2-en-1-one (Compound of Example 32),

(19) (S)-1-(3-(4-amino-5-((3,5-dimethoxyphenyl)ethynyl)-7H-pyrrolo[2,3-d]pyrimidin-7-yl)pyrrolidin-1-yl)-4-(dimethylamino)but-2-en-1-one (Compound of Example 38),

(20) (S)-1-(3-(4-amino-5-((3,5-dimethoxyphenyl)ethynyl)-7H-pyrrolo[2,3-d]pyrimidin-7-yl)pyrrolidin-1-yl)prop-2-en-1-one (Compound of Example 39),

(21) (S)-1-(3-(4-amino-5-((3,5-dimethoxyphenyl)ethynyl)-7H-pyrrolo[2,3-d]pyrimidin-7-yl)pyrrolidin-1-yl)-4-(pyrrolidin-1-yl)but-2-en-1-one (Compound of Example 40),

(22) (S)-1-(3-(4-amino-5-((3,5-dimethoxyphenyl)ethynyl)-7H-pyrrolo[2,3-d]pyrimidin-7-yl)pyrrolidin-1-yl)-4-(4-hydroxypiperidin-1-yl)but-2-en-1-one (Compound of Example 42),

(23) (S)-1-(3-(4-amino-5-((3,5-dimethoxyphenyl)ethynyl)-7H-pyrrolo[2,3-d]pyrimidin-7-yl)pyrrolidin-1-yl)but-2-yn-1-one
(Compound of Example 46),

(24) (S)-1-(3-(4-amino-5-((3,5-dimethoxyphenyl)ethynyl)-7H-pyrrolo[2,3-d]pyrimidin-7-yl)pyrrolidin-1-yl)-4-hydroxy-4-methylpent-2-yn-1-one (Compound of Example 47),

(25) 1-((S)-3-(4-amino-5-((3,5-dimethoxyphenyl)ethynyl)-7H-pyrrolo[2,3-d]pyrimidin-7-yl)pyrrolidin-1-yl)-4-((S)-3-fluoropyrrolidin-1-yl)but-2-en-1-one (Compound of Example 49),

(26) (S)-1-(3-(4-amino-5-((3,5-dimethoxyphenyl)ethynyl)-7H-pyrrolo[2,3-d]pyrimidin-7-yl)pyrrolidin-1-yl)-4-(piperidin-1-yl)but-2-en-1-one (Compound of Example 50),

(27) 1-(3-(4-amino-5-((3,5-dimethoxyphenyl)ethynyl)-7H-pyrrolo[2,3-d]pyrimidin-7-yl)azetidin-1-yl)prop-2-en-1-one
(Compound of Example 51),

(28) 1-(3-(4-amino-5-((3,5-dimethoxyphenyl)ethynyl)-7H-pyrrolo[2,3-d]pyrimidin-7-yl)azetidin-1-yl)-4-(dimethylamino)but-2-en-1-one (Compound of Example 52),

(29) 1-(3-(4-amino-5-((3,5-dimethoxyphenyl)ethynyl)-7H-pyrrolo[2,3-d]pyrimidin-7-yl)azetidin-1-yl)-4-(pyrrolidin-1-yl)but-2-en-1-one (Compound of Example 53),
(30) 1-(3-(4-amino-5-((3,5-dimethoxyphenyl)ethynyl)-7H-pyrrolo[2,3-d]pyrimidin-7-yl)azetidin-1-yl)-4-(azetidin-1-yl)but-2-en-1-one (Compound of Example 55),
(31) 1-(3-(4-amino-5-((3,5-dimethoxyphenyl)ethynyl)-7H-pyrrolo[2,3-d]pyrimidin-7-yl)azetidin-1-yl)-4-(ethyl(methyl)amino)but-2-en-1-one (Compound of Example 56),
(32) 1-(3-(4-amino-5-((3,5-dimethoxyphenyl)ethynyl)-7H-pyrrolo[2,3-d]pyrimidin-7-yl)azetidin-1-yl)-4-(isopropylamino)but-2-en-1-one (Compound of Example 57),
(33) 1-(3-(4-amino-5-((3,5-dimethoxyphenyl)ethynyl)-7H-pyrrolo[2,3-d]pyrimidin-7-yl)azetidin-1-yl)-4-(diethylamino)but-2-en-1-one (Compound of Example 59),
(34) 1-(3-(4-amino-5-((3,5-dimethoxyphenyl)ethynyl)-7H-pyrrolo[2,3-d]pyrimidin-7-yl)azetidin-1-yl)-4-((2-methoxyethyl)(methyl)amino)but-2-en-1-one (Compound of Example 60),
(35) 1-(3-(4-amino-5-((3,5-dimethoxyphenyl)ethynyl)-7H-pyrrolo[2,3-d]pyrimidin-7-yl)azetidin-1-yl)-4-(4-hydroxypiperidin-1-yl)but-2-en-1-one (Compound of Example 61),
(36) (S)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Compound of Example 62),
(37) (R)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Compound of Example 63),
(38) (2S,4S)-methyl-1-acryloyl-4-(4-amino-5-((3,5-dimethoxyphenyl)ethynyl)-7H-pyrrolo[2,3-d]pyrimidin-7-yl)pyrrolidine-2-carboxylate (Compound of Example 66),
(39) 1-((2S,4S)-4-(4-amino-5-((3,5-dimethoxyphenyl)ethynyl)-7H-pyrrolo[2,3-d]pyrimidin-7-yl)-2-(1,3,4-oxadiazol-2-yl)pyrrolidin-1-yl)prop-2-en-1-one (Compound of Example 68), and
(40) (S)-1-(3-(4-amino-3-((3,5-dimethoxyphenyl)ethynyl)-1H-pyrrolo[3,2-c]pyridin-1-yl)pyrrolidin-1-yl)prop-2-en-1-one (Compound of Example 73).

Next, the method for producing Compound (I), which is the active ingredient of the antitumor agent according to the present invention, will be explained. Compound (I) can be produced, for example, by the following production methods or by the methods described in Examples. However, the method for producing Compound (I) is not limited to these reaction examples.

Production method 1

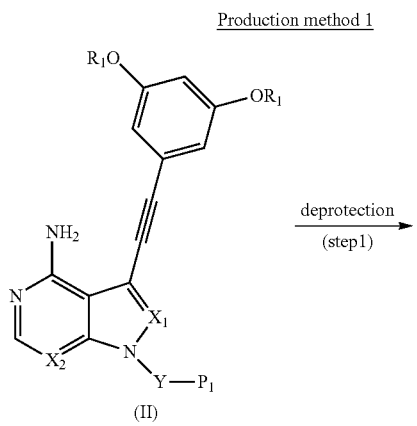

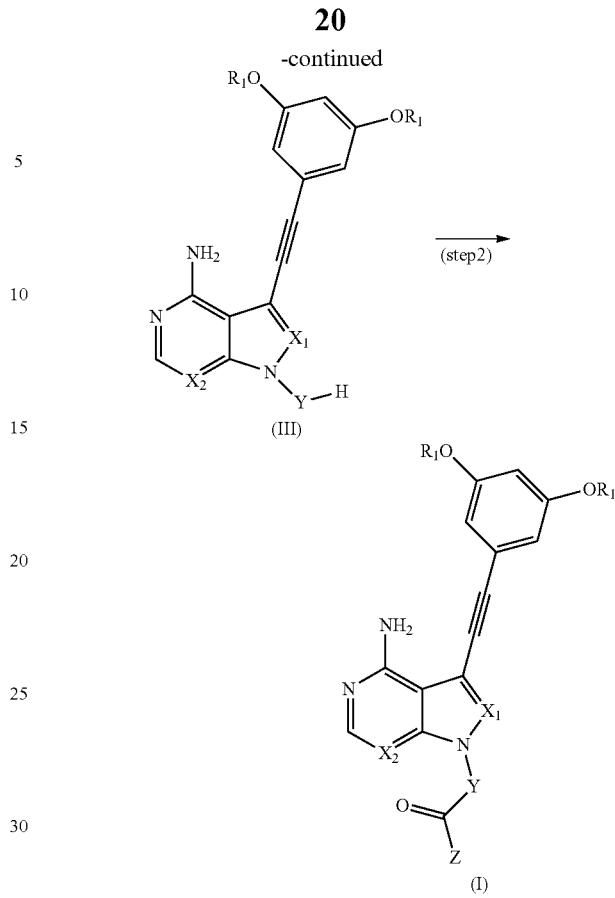

(wherein $P_1$ is a protecting group of the amino group contained in Y; and $R_1$, $X_1$, $X_2$, Y, and Z are as defined above.)

(Step 1) In this step, the protected amino group of the compound of Formula (II) is deprotected to produce the compound of Formula (III). The method for the deprotection can be performed according to a known method, such as the method described in Protective Groups in Organic Synthesis, T. W. Greene, John Wiley & Sons (1981); or methods similar thereto. An example of the protecting group is tert-butyloxycarbonyl. If a tert-butyloxycarbonyl group is used as a protecting group, the deprotection is preferably performed under acidic conditions. Examples of acids that can be used include hydrochloric acid, acetic acid, trifluoroacetic acid, sulfuric acid, methanesulfonic acid, tosic acid, and the like. Such an acid is preferably used in an amount of 1 to 100 moles per mole of Compound (II).

Any solvent that does not adversely affect the reaction can be used. Examples thereof include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane and tetrahydrofuran), aprotic polar solvents (e.g., N,N-dimethylformamide, dimethyl sulfoxide, and hexamethylphosphoramide), or a mixture thereof. The reaction time is 0.1 to 100 hours, and preferably 0.5 to 24 hours. The reaction temperature is 0 to 120° C., and preferably 0 to 90° C.

The thus-obtained compound of Formula (III) can be subjected to the subsequent step after or without isolation and purification by known separation and purification means, such as concentration, vacuum concentration, crystallization, solvent extraction, reprecipitation, and chromatography.

(Step 2) In this step, the compound of Formula (III) is amidated with a carboxylic acid represented by Z—COOH or with an acid halide represented by Z—C(═O)-L (wherein L is chlorine or bromine) to produce the compound of Formula (I).

When a carboxylic acid represented by Z—COOH is used as an amidation reagent, the reaction is performed by using the carboxylic acid in an amount of 0.5 to 10 moles, and preferably 1 to 3 moles, per mole of the compound of Formula (III) in the presence of a suitable condensing agent. The carboxylic acid may be a commercially available product, or can be produced according to a known method.

Any reaction solvent that does not adversely affect the reaction can be used. Examples of preferable solvents include isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, and mixed solvents thereof. The reaction temperature is usually −78 to 200° C., and preferably 0 to 50° C. The reaction time is typically 5 minutes to 3 days, and preferably 5 minutes to 10 hours.

Examples of the condensing agent include diphenylphosphoryl azide, N,N'-dicyclohexylcarbodiimide, benzotriazol-1-yloxy-trisdimethylaminophosphonium salts, 4-(4,6-dimethoxy-1,3,5-triazin-2-yl)-4-methylmopholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, O-(7-azabenzotriazo-1-yl)-N,N,N',N'-tetramethyluronium hexafluorophosphate, and the like.

A base can be optionally added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base is added in an amount of 1 to 100 moles, and preferably 1 to 10 moles, per mole of the compound of Formula (III).

When an acid halide represented by Z—C(═O)-L (wherein L is chlorine or bromine) is used as an amidation reagent, the acid halide is used in an amount of 0.5 to 5 moles, and preferably 0.9 to 1.1 moles, per mole of the compound of Formula (III). The acid halide may be a commercially available product, or can be produced according to a known method.

Any reaction solvent that does not adversely affect the reaction can be used. Examples of preferable solvents include toluene, benzene, methylene chloride, chloroform, tetrahydrofuran, 1,4-dioxane, dimethylformamide, dimethylacetamide, N-methylpyrrolidinone, and mixed solvents thereof. The reaction temperature is typically −78 to 200° C., and preferably −20 to 50° C. The reaction time is typically 5 minutes to 3 days, and preferably 5 minutes to 10 hours.

A base can be optionally added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base is added in an amount of 1 to 100 moles, preferably 1 to 10 moles, per mole of the compound of Formula (III).

The thus-obtained compound of Formula (I) can be isolated and purified by known separation and purification means, such as concentration, vacuum concentration, crystallization, solvent extraction, reprecipitation, and chromatography.

Among Compounds (I), compound of Formula (I') or (I") can also be produced by production method 2 using, for example, Compound (III) obtained in step 1 of production method 1 as a starting compound, and using a specific amine.

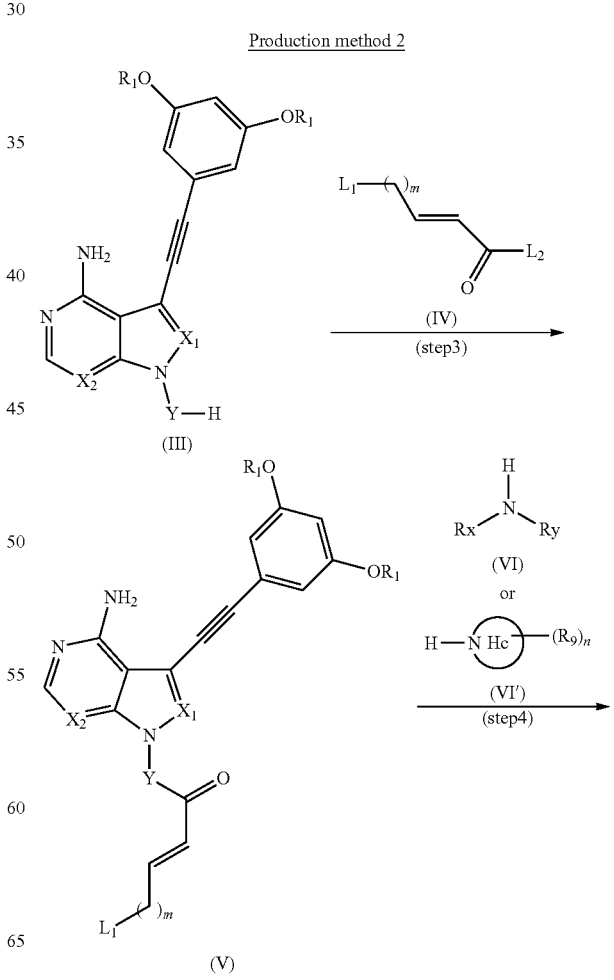

Production method 2

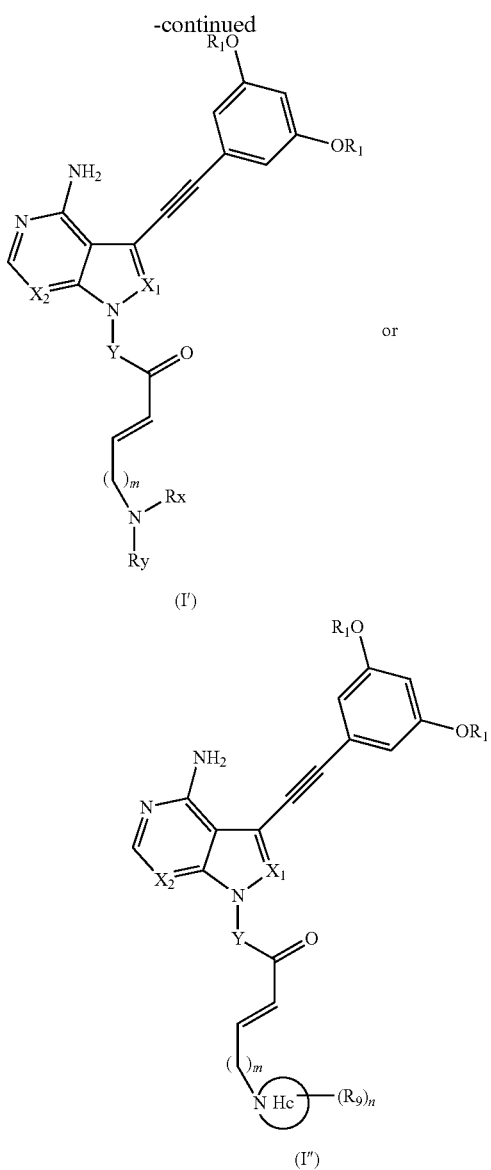

(wherein $L_1$ and $L_2$ are halogen; H of Y—H is hydrogen directly bound to a nitrogen atom; and $X_1$, $X_2$, Y, $R_x$, $R_y$, $R_1$,

m, and n are as defined above.)

(Step 3) In this step, the compound of Formula (III) is amidated with an acid halide represented by Formula (IV) to produce the compound of Formula (V).

Examples of halogen atoms represented by $L_1$ or $L_2$ in Formula (IV) include bromine and chlorine. The compound represented by Formula (IV) may be a commercially available product, or can be produced according to a known method.

The compound of Formula (IV) is used in an amount of 0.5 to 5 moles, and preferably 0.9 to 1.1 moles, per mole of Compound (III).

A base can be optionally added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 10 moles, per mole of the compound of Formula (III).

Any reaction solvent that does not adversely affect the reaction can be used. Examples of preferable reaction solvents include toluene, benzene, methylene chloride, chloroform, tetrahydrofuran, 1,4-dioxane, dimethylformamide, dimethylacetamide, N-methylpyrrolidinone, and mixed solvents thereof. The reaction temperature is typically −78 to 200° C., and preferably 0 to 50° C. The reaction time is typically 5 minutes to 3 days, and preferably 5 minutes to 10 hours.

The thus-obtained compound of Formula (V) can be subjected to the subsequent step after or without isolation and purification by known separation and purification means, such as concentration, vacuum concentration, crystallization, solvent extraction, reprecipitation, and chromatography.

(Step 4) In this step, the compound of Formula (V) is alkylated with an amine represented by Formula (VI) or (VI') to produce the compound of Formula (I') or (I").

The compound of Formula (VI) or (VI') can be used in an amount of 1 to 20 moles, and preferably 1 to 10 moles, per mole of the compound of Formula (V).

Further, a base can optionally be added for the reaction. Examples of such bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Such a base can be added in an amount of 1 to 100 moles, and preferably 1 to 20 moles, per mole of the compound of Formula (V).

Any reaction solvent that does not adversely affect the reaction can be used. For example, N,N-dimethylformamide, N,N-dimethylacetamide, dimethyl sulfoxide, tetrahydrofuran, 1,4-dioxane, N-methylpyrrolidin-2-one, acetonitrile, and the like can be used singly, or as a mixture. The reaction time is 0.1 to 100 hours, and preferably 0.5 to 24 hours. The reaction temperature is 0° C. to the boiling temperature of the solvent, and preferably 0 to 100° C.

The thus-obtained compound of Formula (I') or (I") can be isolated and purified by known separation and purification means, such as concentration, vacuum concentration, crystallization, solvent extraction, reprecipitation, and chromatography.

The compound of Formula (II) used for producing Compound (I) can be produced, for example, by production method 3 or 4.

Production method 3

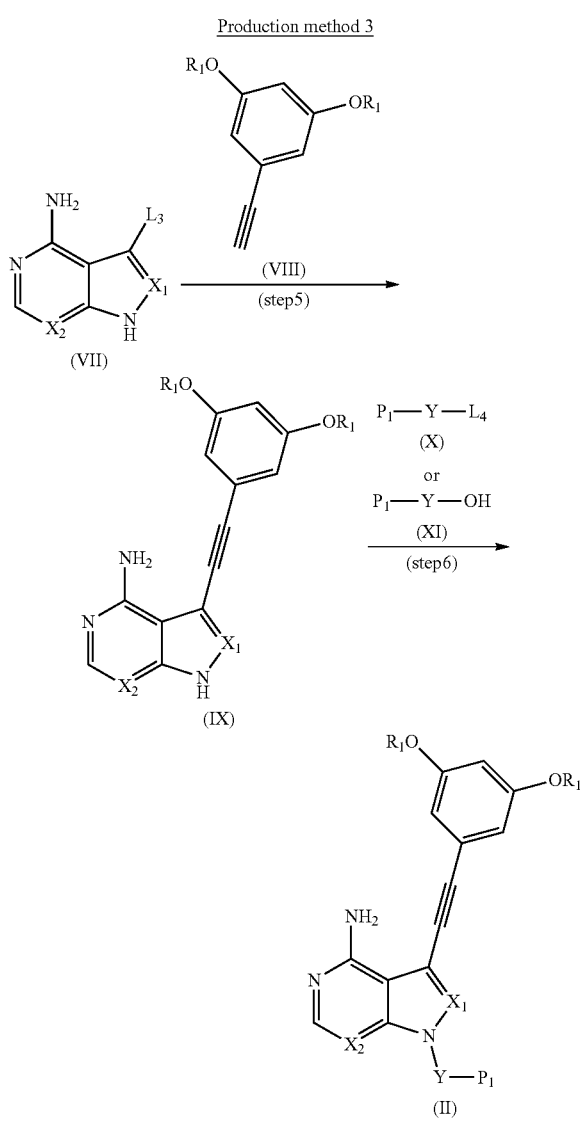

(wherein $L_3$ and $L_4$ are leaving groups; and $R_1$, $X_1$, $X_2$, Y, and $P_1$ are as defined above.)

(Step 5) In this step, the compound of Formula (VII) is subjected to a coupling (Sonogashira) reaction with the compound of Formula (VIII) to produce the compound of Formula (IX). This step can be performed according to a generally known method (see, for example, Chemical Reviews, vol. 107, p. 874, 2007), for example, in the presence of a transition metal catalyst and a base in a solvent that does not adversely affect the reaction.

In Formula (VII), the leaving group represented by $L_3$ is bromine or iodine. The compound of Formula (VII) may be a commercially available product, or can be produced by a known method.

In this step, the compound of Formula (VIII) can be used in an amount of 1 to 10 moles, and preferably 1 to 3 moles, per mole of the compound of Formula (VII).

Examples of transition metal catalysts that can be used in this step include palladium catalysts (e.g., palladium acetate, tris(dibenzylideneacetone)dipalladium, and 1,1f-bis(diphenylphosphino)ferrocene-palladium(II) dichloride dichloromethane complex). If necessary, a ligand (e.g., triphenylphosphine and tri-tert-butylphosphine) can be added and a copper reagent (e.g., copper iodide and copper acetate) can be used as a cocatalyst. The amount of the transition metal catalyst used may vary depending on the type of catalyst. The transition metal catalyst is typically used in an amount of 0.0001 to 1 mole, and preferably 0.01 to 0.5 moles, per mole of the compound of Formula (VII). The amount of the ligand used is typically 0.0001 to 4 moles, and preferably 0.01 to 2 moles, per mole of the compound of Formula (VII). The amount of the cocatalyst used is typically 0.0001 to 4 moles, and preferably 0.01 to 2 moles, per mole of the compound of Formula (VII).

A base may optionally be added for the reaction. Examples of usable bases include organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases such as sodium hydrogen carbonate, sodium carbonate, potassium carbonate, cesium carbonate, sodium hydroxide, and sodium hydride. Among them, organic bases such as triethylamine and diisopropylethylamine are preferable. The amount of the base used is typically 0.1 to 50 moles, preferably 1 to 20 moles, per mole of the compound of Formula (VII).

Any reaction solvent that does not adversely affect the reaction can be used. Examples of usable solvents include hydrocarbons (e.g., benzene, toluene, and xylene), nitriles (e.g., acetonitrile), ethers (e.g., dimethoxyethane, tetrahydrofuran, and 1,4-dioxane), alcohols (e.g., methanol and ethanol), aprotic polar solvents (e.g., dimethylformamide, dimethyl sulfoxide, and hexamethylphosphoramide), water, and mixtures thereof. The reaction time is 0.1 to 100 hours, and preferably 0.5 to 24 hours. The reaction temperature is 0° C. to the boiling temperature of the solvent, and preferably 0 to 150° C.

The thus-obtained compound of Formula (IX) can be subjected to the subsequent step after or without isolation and purification by known separation and purification means, such as concentration, vacuum concentration, crystallization, solvent extraction, reprecipitation, and chromatography.

(Step 6) In this step, the compound of Formula (IX) is used with the compound of Formula (X) or (XI) to produce the compound of Formula (II).

When the compound of Formula (X) is used as an alkylating reagent, the compound of Formula (II) can be produced in the presence of a base. In Formula (X), $L_4$ may be a leaving group, such as chlorine, bromine, iodine, a methanesulfonic acid ester, or a p-toluenesulfonic acid ester. The alkylating reagent may be a commercially available product, or can be produced according to a known method. The compound of Formula (X) can be used in an amount of 1 to 10 moles, preferably 1 to 5 moles, per mole of the compound of Formula (IX).

Examples of usable bases include inorganic bases such as sodium hydrogen carbonate, sodium carbonate, potassium carbonate, cesium carbonate, cesium hydroxide, sodium hydride, and potassium hydride; and organic amines such as trimethylamine, triethylamine, tripropylamine, diisopropylethylamine, N-methylmorpholine, pyridine, 4-(N,N-dimethylamino)pyridine, lutidine, and collidine. Such a base can be used in an amount of 1 to 100 moles, preferably 2 to 10 moles, per mole of the compound of Formula (IX).

As the solvent, N,N-dimethylformamide, N,N-dimethylacetamide, dimethyl sulfoxide, tetrahydrofuran, 1,4-dioxane, N-methylpyrrolidin-2-one, acetonitrile, and the like can be used singly, or as a mixture. The reaction time is 0.1 to 100 hours, and preferably 0.5 to 24 hours. The reaction temperature is 0° C. to the boiling temperature of the solvent, and preferably 0 to 100° C.

When the compound of Formula (XI) is used as an alkylating reagent, the compound of Formula (II) can be produced by using a Mitsunobu reaction. This step can be performed according to a generally known method (see, for example, Chemical Reviews, Vol. 109, p. 2551, 2009), for example, in the presence of Mitsunobu reagents and a phosphine reagent in a solvent that does not adversely affect the reaction. This step is performed using the compound of Formula (XI) in an amount of 1 to 10 moles per mole of the compound of Formula (IX).

Examples of Mitsunobu reagents include diethyl azodicarboxylate, diisopropyl azodicarboxylate, and the like. Such Mitsunobu reagents are used in an amount of 1 to 10 moles, and preferably 1 to 5 moles, per mole of the compound of Formula (IX).

Examples of phosphine reagents include triphenylphosphine, tributylphosphine, and the like. Such a phosphine reagent is used in an amount of 1 to 10 moles, and preferably 1 to 5 moles, per mole of the compound of Formula (IX).

Any reaction solvent that does not adversely affect the reaction can be used. Examples of preferable reaction solvents include toluene, benzenetetrahydrofuran, 1,4-dioxane, dimethylformamide, dimethylacetamide, N-methylpyrrolidinone, dimethyl sulfoxide, and mixed solvents thereof.

The reaction temperature is typically −78 to 200° C., and preferably 0 to 50° C. The reaction time is typically 5 minutes to 3 days, and preferably 10 minutes to 10 hours.

The thus-obtained compound of Formula (II) can be utilized after or without isolation and purification by known separation and purification means, such as concentration, vacuum concentration, crystallization, solvent extraction, reprecipitation, and chromatography, to produce Compound (I).

Production method 4

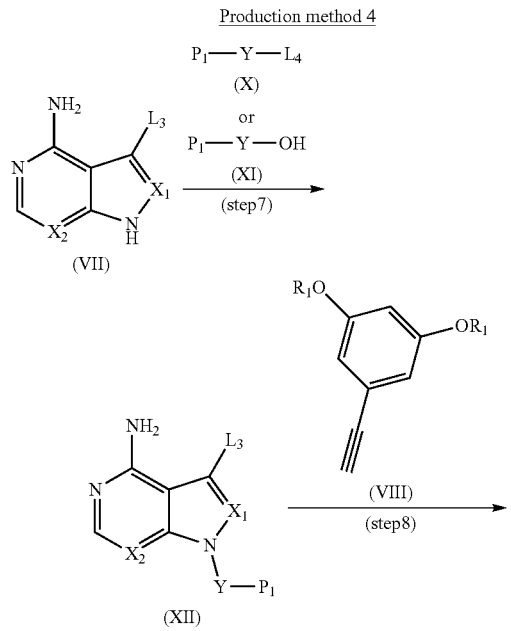

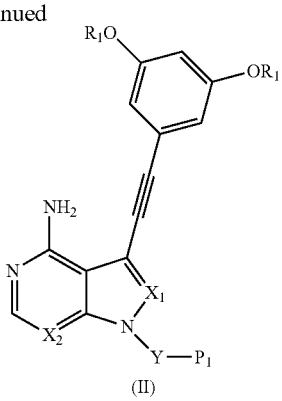

(wherein $L_3$, $L_4$, $R_1$, $X_1$, $X_2$, Y, and $P_1$ are as defined above.)

(Step 7) This step can be performed in a manner similar to step 6.

(Step 8) This step can be performed in a manner similar to step 5.

The compound of Formula (XII) used in the production of Compound (I) can also be produced, for example, by production method 5.

Production method 5

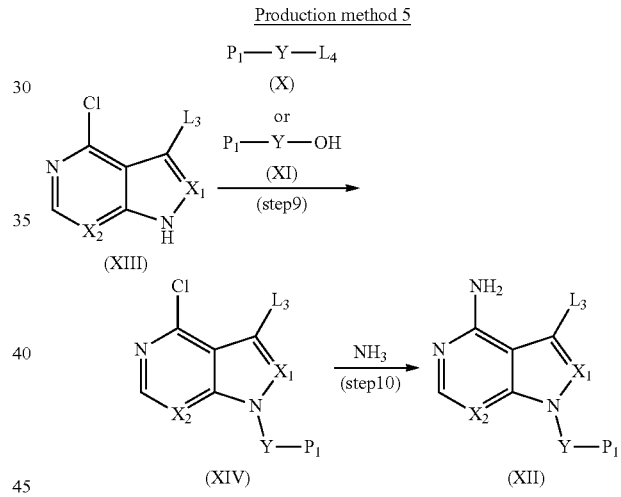

(wherein $L_3$, $L_4$, $X_1$, $X_2$, Y, and $P_1$ are as defined above.)

(Step 9) This step can be performed in a manner similar to step 6.

(Step 10) In this step, the compound of Formula (XIV) is reacted with ammonia or a salt thereof to produce the compound of Formula (XII).

The ammonia or a salt thereof is typically used in an equimolar to excessive molar amount per mole of the compound of Formula (XIII) in this step. Any reaction solvent that does not adversely affect the reaction can be used. Examples of preferable reaction solvents include water, methanol, ethanol, isopropanol, tert-butyl alcohol, tetrahydrofuran, 1,4-dioxane, dimethylformamide, N-methylpyrrolidone, dimethyl sulfoxide, and mixed solvents thereof.

The reaction temperature is typically 0 to 200° C., and preferably room temperature to 150° C. The reaction time is typically 5 minutes to 7 days, and preferably 30 minutes to 24 hours.

The thus-obtained compound of Formula (XIV) can be subjected to the subsequent step 8 after or without isolation and purification by known separation and purification means, such as concentration, vacuum concentration, crystallization, solvent extraction, reprecipitation, and chromatography.

The compound of Formula (IX) used in the production of Compound (I) can also be produced, for example, by production method 6.

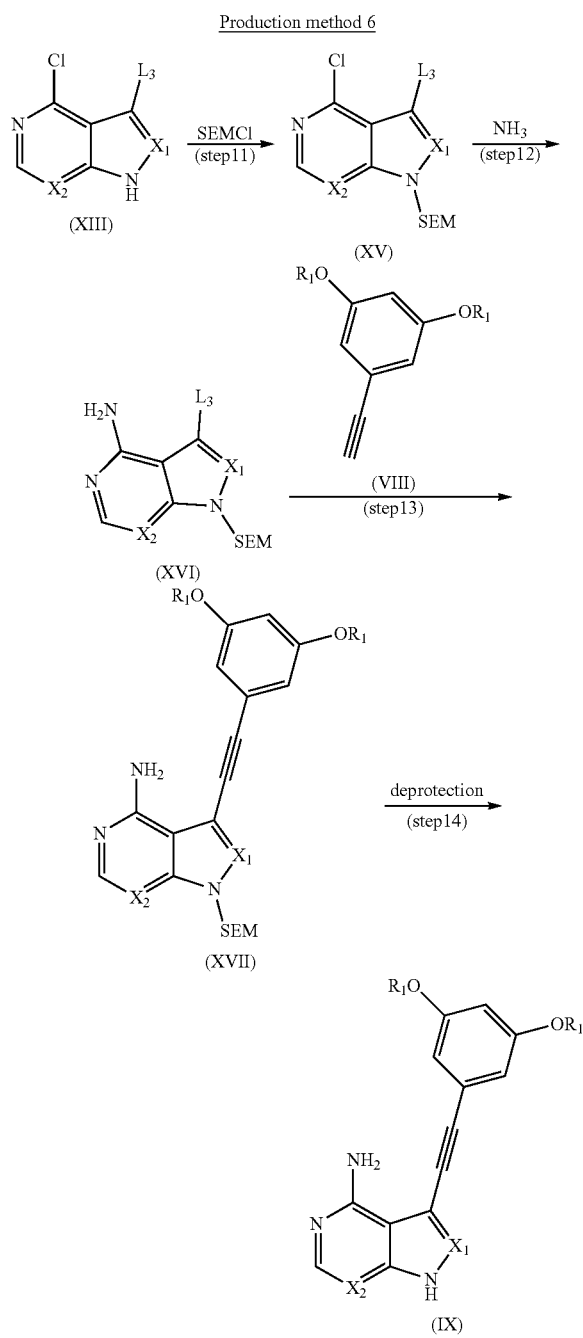

(wherein $L_3$, $X_1$, and $X_2$ are as defined above, and SEM is trimethylsilylethoxymethyl.)

(Step 11) In this step, the compound of Formula (XIII) is reacted with SEMCl (trimethylsilylethoxymethylchloride) in the presence of a base to produce the compound of Formula (XV). The compound of Formula (XIII) may be a commercially available product, or can be produced according to a known method.

SEMCl is typically used in an equimolar to excessive molar amount per mole of the compound of Formula (XIII) in this step. Any reaction solvent that does not adversely affect the reaction can be used. Examples of preferable reaction solvents include tetrahydrofuran, 1,4-dioxane, chloroform, methylene chloride, dimethylformamide, N-methylpyrrolidone, and mixed solvents thereof.

Examples of usable bases include organic bases such as triethylamine, diisopropylethylamine, pyridine, and 4-dimethylaminopyridine; and inorganic bases such as sodium hydrogen carbonate, sodium carbonate, potassium carbonate, cesium carbonate, sodium hydroxide, sodium hydride, and potassium tert-butyrate.

Such a base is typically used in an equimolar to excessive molar amount, and preferably 1 to 3 moles, per mole of the compound of Formula (XIII).

The reaction temperature is typically −78 to 50° C., and preferably 0° C. to room temperature. The reaction time is typically 5 minutes to 7 days, and preferably 10 minutes to 24 hours.

The thus-obtained compound of Formula (XV) can be subjected to the subsequent step after or without isolation and purification by known separation and purification means, such as concentration, vacuum concentration, crystallization, solvent extraction, reprecipitation, and chromatography.

(Step 12) This step can be performed in a manner similar to step 10.

The thus-obtained compound of Formula (XVI) can be subjected to the subsequent step after or without isolation and purification by known separation and purification means, such as concentration, vacuum concentration, crystallization, solvent extraction, reprecipitation, and chromatography.

(Step 13) This step can be performed in a manner similar to step 5.

(Step 14) In this step, the compound of Formula (XVII) is deprotected under acidic conditions to produce the compound of Formula (IX). The deprotection can be performed by a known method, such as the method described in Protective Groups in Organic Synthesis, T. W. Greene, John Wiley & Sons (1981); or a method similar thereto.

Examples of usable acids include hydrochloric acid, acetic acid, trifluoroacetic acid, sulfuric acid, methanesulfonic acid, tosic acid, and the like. Such an acid is used in an amount of 1 to 100 moles per mole of the compound of Formula (XVII).

Any solvent that does not adversely affect the reaction can be used. Examples of usable solvents include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., dimethoxyethane, tetrahydrofuran, and 1,4-dioxane), aprotic polar solvents (e.g., N,N-dimethylformamide, dimethyl sulfoxide, and hexamethylphosphoramide), and mixtures thereof. The reaction time is 0.1 to 100 hours, and preferably 0.5 to 24 hours. The reaction temperature is 0° C. to the boiling temperature of the solvent, and preferably 0 to 100° C.

The thus-obtained compound of Formula (IX) can be used in step 6 after or without isolation and purification by known separation and purification means, such as concentration, vacuum concentration, crystallization, solvent extraction, reprecipitation, and chromatography.

In the above production methods 1 to 6, for functional groups having an active proton, such as amino, imino, hydroxy, carboxy, and amide groups, and indole, protected reagents can be used or a protecting group is introduced into such a functional group according to a usual method, and then the protecting group can be removed in an appropriate step in each production method.

The "protecting group of an amino group or protecting group of an imino group" is not particularly limited insofar as it has a protecting function. Examples of such protecting groups include aralkyl groups such as benzyl, p-methoxybenzyl, 3,4-dimethoxybenzyl, o-nitrobenzyl, p-nitrobenzyl, benzhydryl, trityl, and cumyl; lower alkanoyl groups such as formyl, acetyl, propionyl, butyryl, pivaloyl, trifluoroacetyl, and trichloroacetyl; benzoyl; arylalkanoyl groups such as phenylacetyl and phenoxyacetyl; lower alkoxycarbonyl groups such as methoxycarbonyl, ethoxycarbonyl, propyloxycarbonyl, and tert-butoxycarbonyl; aralkyloxycarbonyl groups such as p-nitrobenzyloxycarbonyl and phenethyloxycarbonyl; lower alkylsilyl groups such as trimethylsilyl and tert-butyldimethylsilyl; tetrahydropyranyl; trimethylsilylethoxymethyl; lower alkylsulfonyl groups such as methylsulfonyl, ethylsulfonyl, and tert-butylsulfonyl; lower alkylsulfinyl groups such as tert-butylsulfinyl; arylsulfonyl groups such as benzenesulfonyl and toluenesulfonyl; and imido groups such as phthalimido. In particular, trifluoroacetyl, acetyl, tert-butoxycarbonyl, benzyloxycarbonyl, trimethylsilylethoxymethyl, cumyl, and the like are preferable.

The "protecting group of a hydroxy group" is not particularly limited insofar as it has a protecting function. Examples of such protecting groups include lower alkyl groups such as methyl, ethyl, propyl, isopropyl, and tert-butyl; lower alkylsilyl groups such as trimethylsilyl and tert-butyldimethylsilyl; lower alkoxymethyl groups such as methoxymethyl and 2-methoxyethoxymethyl; tetrahydropyranyl; trimethylsilylethoxymethyl; aralkyl groups such as benzyl, p-methoxybenzyl, 2,3-dimethoxybenzyl, o-nitrobenzyl, p-nitrobenzyl, and trityl; and acyl groups such as formyl, acetyl, and trifluoroacetyl. In particular, methyl, methoxymethyl, tetrahydropyranyl, trimethylsilylethoxymethyl, tert-butyldimethylsilyl, acetyl, and the like are preferable.

The "protecting group of a carboxy group" is not particularly limited insofar as it has a protecting function. Examples of such protecting groups include lower alkyl groups such as methyl, ethyl, propyl, isopropyl, and tert-butyl; halo-lower-alkyl groups such as 2,2,2-trichloroethyl; lower alkenyl groups such as allyl; trimethylsilylethoxymethyl; and aralkyl groups such as benzyl, p-methoxybenzyl, p-nitrobenzyl, benzhydryl, and trityl. In particular, methyl, ethyl, tert-butyl, allyl, benzyl, p-methoxybenzyl, trimethylsilylethoxymethyl, and the like are preferable.

The "protecting group of a carbonyl group" is not particularly limited insofar as it has a protecting function. Examples of such protecting groups include ketals and acetals, such as ethylene ketal, trimethylene ketal, dimethyl ketal, ethylene acetal, trimethylene acetal, and dimethyl acetal.

The method for removing such a protecting group may vary depending on the type of protecting group, stability of the desired compound (I), etc. For example, the following methods can be used: solvolysis using an acid or a base according to the method disclosed in a publication (Protective Groups in Organic Synthesis, third edition, T. W. Green, John Wiley & Sons (1999)) or a method similar thereto, i.e., a reaction method using, for example, 0.01 moles or a large excess of an acid, preferably trifluoroacetic acid, formic acid, or hydrochloric acid, or an equimolar amount to a large excess of a base, preferably potassium hydroxide or calcium hydroxide; chemical reduction using a metal hydride complex or the like; or catalytic reduction using a palladium-carbon catalyst, Raney nickel catalyst, or the like.

Compound (I) can easily be isolated and purified by usual isolation and purification means. Examples of such means include solvent extraction, recrystallization, preparative reversed-phase high-performance liquid chromatography, column chromatography, preparative thin-layer chromatography, and the like.

When Compound (I) has isomers such as optical isomers, stereoisomers, positional isomers, and rotational isomers, any of the isomers and mixtures thereof are included within the scope of Compound (I). For example, when Compound (I) has optical isomers, optical isomers separated from a racemic mixture are also included within the scope of Compound (I). Each of these isomers can be obtained as a single compound by known synthesis and separation means (e.g., concentration, solvent extraction, column chromatography, and recrystallization).

Compound (I) or a salt thereof may be crystalline. A single crystal form thereof and a polymorphic mixture thereof are both included within the scope of Compound (I) or a salt thereof. These crystals can be produced by crystallization according to a crystallization method known per se in the art. Compound (I) or a salt thereof may be a solvate (e.g., a hydrate) or a non-solvate. Any of such forms are included within the scope of Compound (I) or a salt thereof. Compounds labeled with an isotope (such as $^3H$, $^{14}C$, $^{35}S$, or $^{125}I$) are also included within the scope of Compound (I) or a salt thereof.

A prodrug of Compound (I) or a salt thereof refers to a compound that can be converted to Compound (I) or a salt thereof through a reaction with an enzyme, gastric acid, or the like under physiological conditions in vivo, i.e., a compound that can be converted to Compound (I) or a salt thereof by enzymatic oxidation, reduction, hydrolysis, or the like; or a compound that can be converted to Compound (I) or a salt thereof by hydrolysis with gastric acid or the like. Further, the prodrug of Compound (I) or a salt thereof may be compounds that can be converted to Compound (I) or a salt thereof under physiological conditions, such as those described in "*Iyakuhin no Kaihatsu* [Development of Pharmaceuticals]," Vol. 7, Molecular Design, published in 1990 by Hirokawa Shoten Co., pp. 163-198.

The salt of Compound (I) refers to a common salt used in the field of organic chemistry. Examples of such salts include base addition salts to carboxyl when the compound has carboxyl, and acid addition salts to an amino or basic heterocyclic group when the compound has an amino or basic heterocyclic group.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

Compound (I) or a salt thereof has excellent FGFR inhibitory activity, and is useful as an antitumor agent. Further, Compound (I) or a salt thereof has excellent selectivity toward FGFR, and has advantageously fewer side effects caused by other kinases. Although the target cancer is not particularly limited, examples thereof include head and neck cancer, esophagus cancer, gastric cancer, colon cancer, rectum cancer, liver cancer, gallbladder cancer, cholangiocarcinoma, biliary tract cancer, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, blood cancer, multiple myeloma, skin cancer, brain tumor, and mesothelioma. Preferably, the target cancer is blood cancers such as B-cell lymphoma, chronic lymphocytic leukemia, peripheral T-cell lymphoma, myelodysplastic syndrome, acute myeloid leukemia, and acute lymphocytic leukemia.

When Compound (I) or a salt thereof is used as a pharmaceutical preparation, a pharmaceutical carrier can be added, if required, thereby forming a suitable dosage form according to prevention and treatment purposes. Examples of the dosage form include oral preparations, injections, suppositories, ointments, patches, and the like. Of these, oral preparations are preferable. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations can be prepared as follows. An excipient, optionally together with a binder, disintegrant, lubricant, colorant, taste-masking or flavoring agent, etc., is added to Compound (I) or a salt thereof to produce tablets, coated tablets, granules, powders, capsules, or the like, using an ordinary method.

When an injection agent is prepared, a pH adjuster, buffer, stabilizer, isotonizing agent, local anesthetic, etc., may be added to Compound (I) or a salt thereof; and the mixture may be processed into a subcutaneous, intramuscular, or intravenous injection according to an ordinary method.

The amount of Compound (I) or a salt thereof to be contained in such a dosage unit form varies depending on the condition of the patient, the dosage form, etc. The desirable amount in dosage unit form is generally 0.05 to 1,000 mg in the case of an oral preparation, 0.01 to 500 mg in the case of an injection, and 1 to 1,000 mg in the case of a suppository.

Moreover, the daily dose of the medicine having the above-described dosage form may vary depending on the condition, body weight, age, and sex of a patient, etc., and cannot be generalized. For example, the daily dose as Compound (I) or a salt thereof is 0.05 to 1000 mg, preferably 4 to 1000 mg, and more preferably 100 to 500 mg, per adult (body weight: 50 kg) per day. Such a dose of the medicine is administered once a day.

Examples of mammals to which Compound (I) or a salt thereof is administered include humans, monkeys, mice, rats, rabbits, dogs, cats, cows, horses, pigs, sheep, and the like. Compound (I) or a salt thereof may be contained in a kit that is used so that Compound (I) or a salt thereof is administered on the above-mentioned administration schedule. The kit may also include an instrument (e.g., a syringe) for administering Compound (I) or a salt thereof, a document in which the above administration schedule is written, and the like.

EXAMPLES

The present invention is explained in more detail below with reference to Examples and Test Examples; however, the scope of the present invention is not limited to these Examples.

In the Examples, commercially available reagents were used, unless otherwise specified. Purif-Pack (registered trademark) SI, produced by Moritex Corp.; KP-Sil (registered trademark) Silica prepacked column, produced by Biotage; or HP-Sil (registered trademark) Silica prepacked column, produced by Biotage was used as the silica gel column chromatography. Purif-Pack (registered trademark) NH, produced by Moritex Corp; or KP-NH (registered trademark) prepacked column, produced by Biotage was used as the basic silica gel column chromatography. Kieselgel™ 60F 254, Art. 5744, produced by Merck, or $NH_2$ Silica Gel 60F254 Plate, produced by Wako, was used as the preparative thin-layer chromatography. NMR spectrum was measured by using AL400 (400 MHz; produced by JEOL), Mercury 400 (400 MHz; produced by Agilent Technologies, Inc.) spectrometer, or Inova 400 (400 MHz; produced by Agilent Technologies, Inc.) model spectrometer equipped with an OMNMR probe (produced by Protasis). When its deuterated solvent contains tetramethylsilane, the tetramethylsilane was used as the internal reference; and when tetramethylsilane is not contained, an NMR solvent was used as the reference. All the delta values are shown by ppm. The microwave reaction was performed using Discover S-class, produced by CEM Corporation.

The LCMS spectrum was measured using an Acquity SQD (quadrupole), produced by Waters Corporation, under the following conditions.

Column: YMC-Triart C18, 2.0×50 mm, 1.9 μm (produced by YMC)

MS detection: ESI positive

UV detection: 254 and 210 nm

Column flow rate: 0.5 mL/min

Mobile phase: Water/acetonitrile (0.1% formic acid)

Injection volume: 1 μL

TABLE 1

| Gradient | | |
| --- | --- | --- |
| Time (min) | Water | Acetonitrile |
| 0 | 95 | 5 |
| 0.1 | 95 | 5 |
| 2.1 | 5 | 95 |
| 3.0 | STOP | |

Preparative reversed-phase HPLC purification was performed using a preparative separation system available from Waters Corporation, under the following conditions.

Column: Connected YMC-Actus Triart C18, 20×50 mm, 5 μm (produced by YMC) and YMC-Actus Triart C18, 20×10 mm, 5 μm (produced by YMC).
UV detection: 254 nm
MS detection: ESI positive
Column flow rate: 25 mL/min
Mobile phase: Water/acetonitrile (0.1% formic acid)
Injection volume: 0.1 to 0.5 mL
Each symbol stands for the following.
s: Singlet
d: Doublet
t: Triplet
q: Quartet
dd: Double Doublet
dt: Double Triplet
td: Triple Doublet
tt: Triple Triplet
ddd: Double Double Doublet
ddt: Double Double Triplet
dtd: Double Triple Doublet
tdd: Triple Double Doublet
m: Multiplet
br: Broad
brs: Broad Singlet
DMSO-$d_6$: Deuterated dimethyl sulfoxide
CDCl$_3$: Deuterated chloroform
CD$_3$OD: Deuterated methanol
THF: Tetrahydrofuran
DMF: N,N-dimethylformamide
NMP: 1-Methyl-2-pyrrolidinone
DMSO: Dimethyl sulfoxide
TFA: Trifluoroacetic acid
SEMCl: 2-(Trimethylsilyl)ethoxymethyl chloride
PdCl$_2$ (dppf) CH$_2$Cl$_2$: 1,1'-bis(diphenylphosphino) ferrocene-palladium (II) dichloride-dichloromethane complex
WSC: 1-(3-Dimethylaminopropyl)-3-ethylcarbodiimide hydrochloride
HOBt: 1-Hydroxybenzotriazole monohydrate
HATU: O-(7-azabenzotriazol-1-yl)-N,N,N',N'-tetramethyluronium hexafluorophosphate
HBTU: O-benzotriazol-N,N,N',N'-tetramethyluronium hexafluorophosphate
DIAD: Diisopropyl azodicarboxylate
TBAF: Tetrabutylammoniumfluolide
DIPEA: Diisopropylethylamine
Boc$_2$O: Di-tert-butyl dicarbonate
DMAP: Dimethylaminopyridine Example 1

Synthesis of 1-(3-(4-amino-3-((3,5-dimethoxyphenyl)ethynyl)-1H-pyrazolo[3,4-d]pyrimidin-1-yl)pyrolidin-1-yl)prop-2-en-1-one (Compound of Example 1)

(Step 1) Synthesis of 3-((3,5-dimethoxyphenyl)ethynyl)-1H-pyrazolo[3,4-d]pyrimidin-4-amine PdCl$_2$ (dppf) CH$_2$Cl$_2$ (163 mg) was added to a mixture of 3-iodo-1H-pyrazolo[3,4-d]pyrimidin-4-amine (520 mg) synthesized by the method disclosed in WO 2007/126841, 1-ethynyl-3,5-dimethoxybenzene (504 mg), copper (I) iodide (57.3 mg), and triethylamine (0.56 ml) in DMF (10 ml). After nitrogen purging, the resulting mixture was stirred at 90° C. for 6 hours. Chloroform and water were added to the reaction mixture to separate the organic layer. After being washed with a saturated sodium chloride solution, the organic layer was dried over anhydrous sodium sulfate, and the solvent was then distilled off under reduced pressure. The resulting residue was purified by basic silica gel column chromatography (developing solvent: chloroform/methanol) to obtain the title compound as a dark-brown solid (120 mg). Physical properties: m/z[M+H]$^+$ 296.0

(Step 2) Synthesis of tert-butyl 3-(methylsulfonyloxy)pyrrolidine-1-carboxylate

N-Boc-3-pyrrolidinol (1000 mg) was dissolved in chloroform (20 ml). Triethylamine (1.15 ml) and methanesulfonyl chloride (498 μl) were added thereto at 0° C. After stirring at room temperature for 1.0 hour, ethyl acetate and water were added thereto to separate the organic layer. After being washed with a saturated aqueous sodium bicarbonate solution, a saturated aqueous ammonium chloride solution and water, the organic layer was dried over anhydrous sodium sulfate. The solvent was distilled off under reduced pressure to obtain the title compound as a colorless, oily compound (1.2 g). Physical properties: m/z[M+H]$^+$ 266.1

(Step 3) Synthesis of tert-butyl 3-(4-amino-3-((3,5-dimethoxyphenyl)ethynyl)-1H-pyrazolo[3,4-d]pyrimidin-1-yl)pyrrolidine-1-carboxylate A suspension of 3-((3,5-dimethoxyphenyl)ethynyl)-1H-pyrazolo[3,4-d]pyrimidin-4-amine (62 mg) obtained in Step 1, tert-butyl 3-(methylsulfonyloxy)pyrrolidine-1-carboxylate (217 mg) obtained in Step 2, and potassium carbonate (221 mg) in DMF (2.0 ml) was stirred at 70° C. for 1 hour. Ethyl acetate and water were added thereto to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a light-yellow, amorphous substance (36.2 mg). Physical properties: m/z[M+H]$^+$ 465.1

(Step 4) Synthesis of Compound of Example 1

4N-Hydrochloric acid/1,4-dioxane (4 ml) was added to the tert-butyl 3-(4-amino-3-((3,5-dimethoxyphenyl)ethynyl)-1H-pyrazolo[3,4-d]pyrimidin-1-yl)pyrrolidine-1-carboxylate (32 mg) obtained in Step 3, and the mixture was stirred at room temperature for 1.5 hours. After distilling the solvent of the resulting reaction mixture off under reduced pressure, toluene azeotropic distillation was subsequently performed to obtain a crude product of 3-((3,5-dimethoxyphenyl)ethynyl)-1-(pyrrolidin-3-yl)-1H-pyrazolo[3,4-d]pyrimidin-4-amine (32 mg). Chloroform (2.0 ml) and triethylamine (20 μl) were added to a portion of the resulting crude product (12 mg). After cooling to 0° C., acrylic chloride (2.3 μl) dissolved in chloroform (100 μl) was added thereto, and the mixture was stirred at room temperature for 10 minutes. After halting the reaction using a saturated aqueous sodium bicarbonate solution, the resulting product was extracted with ethyl acetate. After drying the result over anhydrous sodium sulfate, the solvent was distilled off under reduced pressure. The resulting residue was purified by silica gel column chromatography (developing solvent: ethyl acetate/methanol) to obtain the title compound as a white solid (6.5 mg). Table 1 shows the physical properties thereof.

Example 2

Synthesis of (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one (Compound of Example 2)

(Step 1) Synthesis of (R)-tert-butyl 3-(methylsulfonyloxy) pyrrolidine-1-carboxylate (R)—N-Boc-3-pyrrolidinol (935 mg) was dissolved in chloroform (15 ml), and triethylamine (1.04 ml) and methanesulfonyl chloride (467 µl) were added thereto at 0° C. After stirring at room temperature for 1.5 hours, ethyl acetate and water were added thereto to separate the organic layer. After being washed with a saturated aqueous sodium bicarbonate solution, a saturated aqueous ammonium chloride solution and water, the organic layer was dried over anhydrous sodium sulfate, and the solvent was distilled off under reduced pressure to obtain the title compound as a colorless, oily compound (1.1 g). Physical properties: m/z [M+H]$^+$ 266.1

(Step 2) Synthesis of (S)-tert-butyl 3-(4-amino-3-((3,5-dimethoxyphenyl)ethynyl)-1H-pyrazolo[3,4-d]pyrimidin-1-yl)pyrrolidine-1-carboxylate A suspension of 3-((3,5-dimethoxyphenyl)ethynyl)-1H-pyrazolo[3,4-d]pyrimidin-4-amine (334 mg) obtained in Example 1 (Step 1), (R)-tert-butyl 3-(methylsulfonyloxy) pyrrolidine-1-carboxylate (379 mg) obtained in (Step 1) above, and potassium carbonate (391 mg) in DMF (4.0 ml) was stirred at 70° C. for 3 hours. Ethyl acetate and water were added thereto to separate the organic layer. The organic layer was dried over anhydrous sodium sulfate, and the solvent was then distilled off under reduced pressure. The resulting residue was purified by basic silica gel column chromatography (developing solvent: hexane/ethyl acetate) to obtain the title compound as a light-yellow, amorphous substance (149 mg). Physical properties: m/z[M+H]$^+$ 465.1

(Step 3) Synthesis of Compound of Example 2

In accordance with Example 1 (Step 4), except that (S)-tert-butyl 3-(4-amino-3-((3,5-dimethoxyphenyl)ethynyl)-1H-pyrazolo[3,4-d]pyrimidin-1-yl)pyrrolidine-1-carboxylate obtained in (Step 2) above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of (S)-3-((3,5-dimethoxyphenyl)ethynyl)-1-(pyrrolidin-3-yl)-1H-pyrazolo[3,4-d]pyrimidin-4-amine was obtained by removing a Boc group under acidic conditions. Thereafter, amidation was conducted to obtain the title compound as a white solid. Table 1 shows the physical properties thereof.

Example 3

Synthesis of 1-(3-(4-amino-3-((3,5-dimethoxyphenyl)ethynyl)-1H-pyrazolo[3,4-d]pyrimidin-1-yl)pyrrolidin-1-yl)but-2-en-1-one (Compound of Example 3)

In accordance with Example 1 (Step 4), except that 2-butenoyl chloride was used in place of acrylic chloride, the title compound was obtained as a white solid. Table 1 shows the physical properties thereof.

Example 4

Synthesis of (S)-1-(3-(4-amino-3-((3,5-dimethoxyphenyl)ethynyl)-1H-pyrazolo[3,4-d]pyrimidin-1-yl)pyrrolidin-1-yl)-4-(dimethylamino)but-2-en-1-one (Compound of Example 4)

The crude product (5.6 mg) of (S)-3-((3,5-dimethoxyphenyl)ethynyl)-1-(pyrrolidin-3-yl)-1H-pyrazolo[3,4-d]pyrimidin-4-amine obtained in Example 2 as an intermediate, 4-(dimethylamino)but-2-enoic acid hydrochloride (6.3 mg), and HATU (15 mg) were dissolved in DMF (1.0 ml). DIPEA (50 µl) was added thereto, followed by stirring overnight. Chloroform and water were added to the reaction mixture to separate the organic layer. After being washed with a saturated sodium chloride solution, the organic layer was dried over anhydrous sodium sulfate, and the solvent was then distilled off under reduced pressure. The resulting residue was purified by preparative reversed-phase HPLC purification (water/acetonitrile (0.1% formic acid)) to obtain the title compound as a colorless, amorphous substance (2.3 mg). Table 1 shows the physical properties thereof.

Example 5

Synthesis of (S)-1-(3-(4-amino-3-((3,5-dimethoxyphenyl)ethynyl)-1H-pyrazolo[3,4-d]pyrimidin-1-yl)pyrrolidin-1-yl)prop-2-yn-1-one (Compound of Example 5)

The crude product (16 mg) of (S)-3-((3,5-dimethoxyphenyl)ethynyl)-1-(pyrrolidin-3-yl)-1H-pyrazolo[3,4-d]pyrimidin-4-amine obtained in Example 2 as an intermediate, 3-(trimethylsilyl)propionic acid (10 mg), HATU (28 mg) were dissolved in DMF (0.5 ml). DIPEA (31 µl) was added thereto, followed by stirring overnight. Ethyl acetate and a saturated aqueous sodium bicarbonate solution were added to the reaction mixture to separate the organic layer. After drying the organic layer over anhydrous sodium sulfate, the solvent was distilled off under reduced pressure. The resulting residue was purified by silica gel column chromatography (developing solvent: ethyl acetate/methanol) to obtain the title compound as a white solid (0.7 mg). Table 2 shows the physical properties thereof.

Example 6

Synthesis of (S)-1-(3-(4-amino-3-((3,5-dimethoxyphenyl)ethynyl)-1H-pyrazolo[3,4-d]pyrimidin-1-yl)pyrrolidin-1-yl)-2-fluoroprop-2-en-1-one (Compound of Example 6)

In accordance with Example 4, except that 2-fluoroacrylic acid was used in place of 4-(dimethylamino)but-2-enoic acid hydrochloride, the title compound was obtained as a colorless, amorphous substance. Table 2 shows the physical properties thereof.

Example 7

Synthesis of (S)-1-(3-(4-amino-3-((3,5-dimethoxyphenyl)ethynyl)-1H-pyrazolo[3,4-d]pyrimidin-1-yl)pyrrolidin-1-yl)-2-(pyrrolidin-1-ylmethyl)prop-2-en-1-one (Compound of Example 7)

In accordance with Example 4, except that 2-(pyrrolidin-1-ylmethyl)acetic acid (Synth. Commun. 1995, 641) was used in place of 4-(dimethylamino)but-2-enoic acid hydrochloride, the title compound was obtained as a colorless, amorphous substance. Table 2 shows the physical properties thereof.

Example 8

Synthesis of (S)-1-(3-(4-amino-3-((3,5-diethoxyphenyl)ethynyl)-1H-pyrazolo[3,4-d]pyrimidin-1-yl)pyrrolidin-1-yl)prop-2-en-1-one (Compound of Example 8)

(Step 1) Synthesis of 1,3-diethoxy-5-ethynylbenzene

Carbon tetrabromide (4.78 g) was dissolved in dichloroethane (14 mL), and triphenylphosphine (7.56 g) was added thereto at 0° C. After stirring at 0° C. for 5 minutes, a solution of 3,5-diethoxybenzaldehyde (1.40 g) in dichloromethane (7 mL) was added thereto, followed by stirring for 20 minutes. Without performing further treatment, the reaction mixture was purified by silica gel chromatography (developing solvent: hexane/ethyl acetate) to obtain 1-(2,2-dibromovinyl)-3,5-diethoxybenzene. The obtained compound was used for the subsequent reaction without further purification. The compound obtained above was dissolved in THF (30 mL). A 1.63 M n-butyllithium solution in hexane (10.5 mL) was added thereto at −78° C. The resulting mixture was stirred at −78° C. for 30 minutes. After adding a saturated aqueous ammonium chloride solution, the reaction mixture was subjected to extraction using ethyl acetate. The resulting organic layer was washed with a saturated sodium chloride solution, and the organic layer was then dried over anhydrous sodium sulfate. The solvent was concentrated under reduced pressure. The resulting residue was purified by silica gel column chromatography (developing solvent: hexane/ethyl acetate) to obtain the title compound as a colorless, oily substance (1.31 g). Physical properties: m/z[M+H]$^+$ 191.0

(Step 2) In accordance with Example 1, except that 1,3-diethoxy-5-ethynylbenzene obtained in Step 1 was used in place of 1-ethynyl-3,5-dimethoxybenzene, the title compound was obtained as a colorless, amorphous substance. Table 2 shows the physical properties thereof.

Example 9

Synthesis of 1-(3-(4-amino-3-((3,5-dimethoxyphenyl)ethynyl)-1H-pyrazolo[3,4-d]pyrimidin-1-yl)azetidin-1-yl)prop-2-en-1-one (Compound of Example 9)

(Step 1) Synthesis of tert-butyl 3-(methylsulfonyloxy)azetidine-1-carboxylate

N-Boc-3-hydroxyazetidine (1.73 g) was dissolved in chloroform (20 ml). Triethylamine (2.09 ml) and methanesulfonyl chloride (856 μl) were added thereto at 0° C. After stirring at room temperature for 0.5 hours, ethyl acetate and water were added thereto to separate the organic layer. After being washed with a saturated aqueous sodium bicarbonate solution, a saturated aqueous ammonium chloride solution, and water, the organic layer was dried over anhydrous sodium sulfate. The solvent was then distilled off under reduced pressure to obtain the title compound as a colorless, oily compound (2.32 g). Physical properties: m/z[M+H]$^+$ 252.0

(Step 2) Synthesis of tert-butyl 3-(4-amino-3-iodo-1H-pyrazolo[3,4-d]pyrimidin-1-yl)azetidine-1-carboxylate A suspension of tert-butyl 3-(methylsulfonyloxy)azetidine-1-carboxylate (1.32 g) obtained in Step 1 above, 3-iodo-1H-pyrazolo[3,4-d]pyrimidin-4-amine (1.37 g), and cesium carbonate (3.47 g) in DMF (10 ml) was stirred at 90° C. for 10 hours. Ethyl acetate and water were added thereto to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a light-yellow amorphous substance (482 mg). Physical properties: m/z[M+H]$^+$ 417.0

(Step 3) Synthesis of tert-butyl 3-(4-amino-3-((3,5-dimethoxyphenyl)ethynyl)-1H-pyrazolo[3,4-d]pyrimidin-1-yl)azetidine-1-carboxylate PdCl$_2$ (dppf) CH$_2$Cl$_2$ (39 mg) was added to a mixture of tert-butyl 3-(4-amino-3-iodo-1H-pyrazolo[3,4-d]pyrimidin-1-yl)azetidine-1-carboxylate (200 mg) obtained in Step 2 above, 1-ethynyl-3,5-dimethoxybenzene (117 mg), copper (I) iodide (14 mg), and triethylamine (0.5 ml) in THF (5 ml). After nitrogen purging, the resulting mixture was stirred at 80° C. for 1.5 hours. Ethyl acetate and water were added to the reaction mixture to separate the organic layer. After being washed with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (185 mg). Physical properties: m/z[M+H]$^+$ 451.1

(Step 4) Synthesis of Compound of Example 9

In accordance with Example 1 (Step 4), except that tert-butyl 3-(4-amino-3-iodo-1H-pyrazolo[3,4-d]pyrimidin-1-yl)azetidine-1-carboxylate obtained in Step 3 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of 1-(azetidin-3-y)-3-((3,5-dimethoxyphenyl)ethynyl)-1H-pyrazolo[3,4-d]pyrimidin-4-amine was obtained by removing a Boc group under acidic conditions. Thereafter, amidation was conducted to obtain the title compound as a white solid. Table 2 shows the physical properties thereof.

Example 10

Synthesis of 1-(3-(4-amino-3-((3,5-dimethoxyphenyl)ethynyl)-1H-pyrazolo[3,4-d]pyrimidin-1-yl)azetidin-1-yl)-4-hydroxybut-2-yn-1-one (Compound of Example 10)

A crude product (6.0 mg) of 1-(azetidin-3-yl)-3-((3,5-dimethoxyphenyl)ethynyl)-1H-pyrazolo[3,4-d]pyrimidin-4-amine obtained in Example 9 as an intermediate, 4-hydroxybut-2-ynoic acid (3.7 mg), and HATU (11 mg) were dissolved in DMF (1.0 ml). DIPEA (30 μl) was added thereto, followed by stirring overnight.

Chloroform and water were added to the reaction mixture to separate the organic layer. After being washed with a saturated sodium chloride solution, the organic layer was dried over anhydrous sodium sulfate, and the solvent was distilled off under reduced pressure. The resulting residue was purified by preparative reversed-phase HPLC purification (water/acetonitrile (0.1% formic acid)) to obtain the title compound as a colorless, amorphous substance (1.4 mg). Table 3 shows the physical properties thereof.

Example 11

Synthesis of 1-(3-(4-amino-3-((3,5-dimethoxyphenyl)ethynyl)-1H-pyrazolo[3,4-d]pyrimidin-1-yl)azetidin-1-yl)-4-hydroxy-4-methylpent-2-yn-1-one (Compound of Example 11)

In accordance with Example 10, except that 4-hydroxy-4-methylpent-2-ynoic acid was used in place of 4-hydroxybut-2-ynoic acid, the title compound was obtained as a colorless, amorphous substance. Table 3 shows the physical properties thereof.

Example 12

Synthesis of 1-(3-(4-amino-3-((3,5-dimethoxyphenyl)ethynyl)-1H-pyrazolo[3,4-d]pyrimidin-1-yl)azetidin-1-yl)-4-(dimethylamino)but-2-en-1-one (Compound of Example 12)

In accordance with Example 10, except that 4-(dimethylamino)but-2-enoic acid hydrochloride was used in place of 4-hydroxybut-2-ynoic acid, the title compound was obtained as a colorless, amorphous substance. Table 3 shows the physical properties thereof.

Example 13

Synthesis of 1-(3-(4-amino-3-((3,5-dimethoxyphenyl)ethynyl)-1H-pyrazolo[3,4-d]pyrimidin-1-yl)azetidin-1-yl)-4-(cyclopropylamino)but-2-en-1-one (compound of Example 13)

(Step 1) Synthesis of 4-bromobut-2-enoyl chloride

Thionyl chloride (3.0 ml) was added to 4-bromocrotonic acid (329 mg), and the mixture was stirred at 80° C. for 5 hours. The reaction mixture was concentrated under reduced pressure, and toluene azeotropic distillation was subsequently performed to obtain the title compound as a crude product (394 mg).

(Step 2) Synthesis of 1-(3-(4-amino-3-((3,5-dimethoxyphenyl)ethynyl)-1H-pyrazolo[3,4-d]pyrimidin-1-yl)azetidin-1-yl)-4-bromobut-2-en-1-one A crude product (140 mg) of 1-(azetidin-3-yl)-3-((3,5-dimethoxyphenyl)ethynyl)-1H-pyrazolo[3,4-d]pyrimidin-4-amine obtained in Example 9 as an intermediate was suspended in THF (4.5 ml), DIPEA (178 μl) was added thereto, and the mixture was cooled to 0° C. A solution of 4-bromobut-2-enoyl chloride (66 mg) obtained in Step 1 above in THF (0.5 ml) was added to the mixture dropwise and stirred at room temperature for 15 minutes. After halting the reaction using a saturated aqueous sodium bicarbonate solution, the resulting product was extracted with ethyl acetate. After drying the result over anhydrous sodium sulfate, the solvent was distilled off under reduced pressure to obtain the title compound as a crude product (160 mg). Physical properties: m/z[M+H]$^+$ 497.0, 499.0

(Step 3) Synthesis of Compound of Example 13

The crude product (12 mg) of 1-(3-(4-amino-3-((3,5-dimethoxyphenyl)ethynyl)-1H-pyrazolo[3,4-d]pyrimidin-1-yl)azetidin-1-yl)-4-bromobut-2-en-1-one obtained in Step 2 above was dissolved in DMF (0.5 ml). Cyclopropylamine (5 μl) and DIPEA (10 μl) were added thereto, and the mixture was stirred at room temperature for 1 hour. After concentrating under reduced pressure, the resulting residue was purified by preparative reversed-phase HPLC purification (water/acetonitrile (0.1% formic acid)) to obtain the title compound as a colorless, amorphous substance (3.4 mg). Table 3 shows the physical properties thereof.

Example 14

Synthesis of 1-(3-(4-amino-3-((3,5-dimethoxyphenyl)ethynyl)-1H-pyrazolo[3,4-d]pyrimidin-1-yl)azetidin-1-yl)-4-(isopropylamino)but-2-en-1-one (Compound of Example 14)

In accordance with Example 13 (Step 3), except that isopropylamine was used in place of cyclopropylamine, the title compound was obtained as a colorless, amorphous substance. Table 4 shows the physical properties thereof.

Example 15

Synthesis of 1-(3-(4-amino-3-((3,5-dimethoxyphenyl)ethynyl)-1H-pyrazolo[3,4-d]pyrimidin-1-yl)azetidin-1-yl)-4-(ethyl(methyl) amino)but-2-en-1-one (Compound of Example 15)

In accordance with Example 13 (Step 3), except that ethylmethylamine was used in place of cyclopropylamine, the title compound was obtained as a colorless, amorphous substance. Table 4 shows the physical properties thereof.

Example 16

Synthesis of 1-(3-(4-amino-3-((3,5-dimethoxyphenyl)ethynyl)-1H-pyrazolo[3,4-d]pyrimidin-1-yl)azetidin-1-yl)-4-(cyclobutylamino)but-2-en-1-one (Compound of Example 16)

In accordance with Example 13 (Step 3), except that cyclobutylamine was used in place of cyclopropylamine, the title compound was obtained as a colorless, amorphous substance. Table 4 shows the physical properties thereof.

Example 17

Synthesis of 1-(3-(4-amino-3-((3,5-dimethoxyphenyl)ethynyl)-1H-pyrazolo[3,4-d]pyrimidin-1-yl)azetidin-1-yl)-4-(diethylamino)but-2-en-1-one (Compound of Example 17)

In accordance with Example 13 (Step 3), except that diethylamine was used in place of cyclopropylamine, the title compound was obtained as a colorless, amorphous substance. Table 5 shows the physical properties thereof.

Example 18

Synthesis of 1-(3-(4-amino-3-((3,5-dimethoxyphenyl)ethynyl)-1H-pyrazolo[3,4-d]pyrimidin-1-yl)azetidin-1-yl)-4-(tert-butylamino)but-2-en-1-one (Compound of Example 18)

In accordance with Example 13 (Step 3), except that tert-butylamine was used in place of cyclopropylamine, the title compound was obtained as a colorless, amorphous substance. Table 5 shows the physical properties thereof.

Example 19

Synthesis of 1-(3-(4-amino-3-((3,5-dimethoxyphenyl)ethynyl)-1H-pyrazolo[3,4-d]pyrimidin-1-yl)azetidin-1-yl)-4-(isopropyl(methyl) amino)but-2-en-1-one (Compound of Example 19)

In accordance with Example 13 (Step 3), except that isopropylmethylamine was used in place of cyclopropylamine, the title compound was obtained as a colorless, amorphous substance. Table 5 shows the physical properties thereof.

Example 20

Synthesis of 1-(3-(4-amino-3-((3,5-dimethoxyphenyl)ethynyl)-1H-pyrazolo[3,4-d]pyrimidin-1-yl)azetidin-1-yl)-4-(piperidin-1-yl)but-2-en-1-one (Compound of Example 20)

In accordance with Example 13 (Step 3), except that piperidine was used in place of cyclopropylamine, the title compound was obtained as a colorless, amorphous substance. Table 5 shows the physical properties thereof.

Example 21

Synthesis of 1-(3-(4-amino-3-((3,5-dimethoxyphenyl)ethynyl)-1H-pyrazolo[3,4-d]pyrimidin-1-yl)azetidin-1-yl)-4-morpholinobut-2-en-1-one (Compound of Example 21)

In accordance with Example 13 (Step 3), except that morpholine was used in place of cyclopropylamine, the title compound was obtained as a colorless, amorphous substance. Table 6 shows the physical properties thereof.

Example 22

Synthesis of (S)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one In accordance with Example 13 (Step 3), except that (S)-3-fluoropyrrolidine was used in place of cyclopropylamine, the title compound was obtained as a colorless, amorphous substance. Table 6 shows the physical properties thereof.

Example 23

Synthesis of (R)-1-(3-(4-amino-3-((3,5-dimethoxyphenyl)ethynyl)-1H-pyrazolo[3,4-d]pyrimidin-1-yl)azetidin-1-yl)-4-(3-fluoropyrrolidin-1-yl)but-2-en-1-one In accordance with Example 13 (Step 3), except that (R)-3-fluoropyrrolidine was used in place of cyclopropylamine, the title compound was obtained as a colorless, amorphous substance. Table 6 shows the physical properties thereof.

Example 24

Synthesis of 1-(3-(4-amino-3-((3,5-diethoxyphenyl)ethynyl)-1H-pyrazolo[3,4-d]pyrimidin-1-yl)azetidin-1-yl)prop-2-en-1-one (Compound of Example 24)

In accordance with Example 9, except that 1,3-diethoxy-5-ethynylbenzene was used in place of 1-ethynyl-3,5-dimethoxybenzene, the title compound was obtained as a colorless, amorphous substance. Table 7 shows the physical properties thereof.

Example 25

Synthesis of 1-(3-(4-amino-3-((3,5-diethoxyphenyl)ethynyl)-1H-pyrazolo[3,4-d]pyrimidin-1-yl)azetidin-1-yl)-4-(dimethylamino)but-2-en-1-one (Compound of Example 25)

In accordance with Example 12, except that 1,3-diethoxy-5-ethynylbenzene was used in place of 1-ethynyl-3,5-dimethoxybenzene, the title compound was obtained as a colorless, amorphous substance. Table 7 shows the physical properties thereof.

Example 26

Synthesis of 1-(3-((4-amino-3-((3,5-dimethoxyphenyl)ethynyl)-1H-pyrazolo[3,4-d]pyrimidin-1-yl)methyl)pyrrolidin-1-yl)prop-2-en-1-one (Compound of Example 26)

(Step 1) Synthesis of tert-butyl 3-((4-amino-3-((3,5-dimethoxyphenyl)ethynyl)-1H-pyrazolo[3,4-d]pyrimidin-1-yl)methyl)pyrrolidine-1-carboxylate DIAD (197 μl) was added to a suspension of 3-((3,5-dimethoxyphenyl)ethynyl)-1H-pyrazolo[3,4-d]pyrimidin-4-amine (148 mg) obtained in Example 1 (Step 1), N-Boc-3-hydroxymethylpyrrolidine (154 mg), polymer supported triphenylphosphine (upto 3.0 mmol/g, 334 mg) in THF (5.0 ml), followed by stirring at room temperature for 3 hours. The insoluble matter was filtered out, and the solvent was distilled off under reduced pressure. The resulting residue was purified by basic silica gel column chromatography (developing solvent: hexane/ethyl acetate) to obtain the title compound as a colorless, amorphous substance (94.5 mg). Physical properties: m/z[M+H]$^+$ 479.1

(Step 2) Synthesis of Compound of Example 26

In accordance with Example 1 (Step 4), except that tert-butyl 3-((4-amino-3-((3,5-dimethoxyphenyl)ethynyl)-

1H-pyrazolo[3,4-d]pyrimidin-1-yl)methyl)pyrrolidine-1-carboxylate obtained in Step 1 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 7 shows the physical properties thereof.

Example 27

Synthesis of (S)-1-(3-(4-amino-3-((3,5-dimethoxyphenyl)ethynyl)-1H-pyrazolo[3,4-d]pyrimidin-1-yl)piperidin-1-yl)prop-2-en-1-one (Compound of Example 27)

In accordance with Example 26, except that (R)-1-Boc-3-hydroxypiperidine was used in place of N-Boc-3-hydroxymethylpyrrolidine, the title compound was obtained as a white solid. Table 7 shows the physical properties thereof.

Example 28

Synthesis of 1-((2S,4S)-4-(4-amino-3-((3,5-dimethoxyphenyl)ethynyl)-1H-pyrazolo[3,4-d]pyrimidin-1-yl)-2-(hydroxymethyl)pyrrolidin-1-yl)prop-2-en-1-one (Compound of Example 28)

(Step 1) Synthesis of (2S,4R)-tert-butyl 2-((tert-butyldiphenylsilyloxy)methyl)-4-hydroxypyrrolidine-1-carboxylate 1-N-Boc-(2S,4R)-4-hydroxy-2-(hydroxymethyl)-pyrrolidine (500 mg) was dissolved in DMF (4.0 ml), and imidazole (164 mg) was added to the dissolution. After cooling to 0° C., tert-butylchlorodiphenylsilane (616 µl) was added to the mixture, and stirred for 1 hour. Ethyl acetate and a saturated aqueous sodium bicarbonate solution were added to the reaction mixture to separate the organic layer. After being washed with a saturated sodium chloride solution, the organic layer was dried over anhydrous sodium sulfate, and the solvent was distilled off under reduced pressure. The resulting residue was purified by silica gel column chromatography (developing solvent: hexane/ethyl acetate) to obtain the title compound as a colorless, oily substance (655 mg). Physical properties: m/z[M+H]$^+$ 456.2

(Step 2) Synthesis of (2S,4S)-tert-butyl 2-((tert-butyldiphenylsilyloxy)methyl)-4-(methylsulfonyloxy)pyrrolidine-1-carboxylate (2S,4R)-tert-Butyl 2-((tert-butyldiphenylsilyloxy)methyl)-4-hydroxypyrrolidine-1-carboxylate (300 mg) obtained in Step 1 above was dissolved in chloroform (3.0 ml). Triethylamine (137 µl) and methanesulfonyl chloride (56 µl) were added to the solution at 0° C. After stirring at room temperature for 2.0 hours, chloroform and water were added thereto to separate the organic layer. The organic layer was dried over anhydrous magnesium sulfate, and the solvent was distilled off under reduced pressure to obtain the title compound as a colorless, oily compound (389 mg). Physical properties: m/z[M+H]$^+$ 534.1

(Step 3) Synthesis of (2S,4S)-tert-butyl 4-(4-amino-3-iodo-1H-pyrazolo[3,4-d]pyrimidin-1-yl)-2-((tert-butyldiphenylsilyloxy)methyl)pyrrolidine-1-carboxylate (2S,4S)-tert-butyl 2-((tert-butyldiphenylsilyloxy)methyl)-4-(methylsulfonyloxy)pyrrolidine-1-carboxylate (389 mg) obtained in Step 2 above, 3-iodo-1H-pyrazolo[3,4-d]pyrimidin-4-amine (188 mg), and potassium carbonate (363 mg) were suspended in DMF (4.0 ml), followed by stirring overnight at 80° C. Ethyl acetate and water were added thereto to separate the organic layer. The organic layer was dried over anhydrous magnesium sulfate, and the solvent was distilled off under reduced pressure. The resulting residue was purified by basic silica gel column chromatography (developing solvent: hexane/ethyl acetate) to obtain the title compound as a colorless, oily substance (191 mg). Physical properties: m/z[M+H]$^+$ 699.1

(Step 4) Synthesis of (2S,4S)-tert-butyl 4-(4-amino-3-((3,5-dimethoxyphenyl)ethynyl)-1H-pyrazolo[3,4-d]pyrimidin-1-yl)-2-((tert-butyldiphenylsilyloxy)methyl)pyrrolidine-1-carboxylate PdCl$_2$ (dppf) CH$_2$Cl$_2$ (13 mg) was added to a mixture of (2S,4S)-tert-butyl 4-(4-amino-3-iodo-1H-pyrazolo[3,4-d]pyrimidin-1-yl)-2-((tert-butyldiphenylsilyloxy)methyl)pyrrolidine-1-carboxylate (113 mg) obtained in Step 3 above, 1-ethynyl-3,5-dimethoxybenzene (52 mg), copper (I) iodide (6 mg), and triethylamine (0.4 ml) in THF (4 ml). After nitrogen purging, the mixture was stirred at 85° C. for 3 hours. Ethyl acetate and water were added to the reaction mixture to separate the organic layer. After washing with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (100 mg). Physical properties: m/z[M+H]$^+$ 733.3

(Step 5) Synthesis of (2S,4S)-tert-butyl 4-(4-amino-3-((3,5-dimethoxyphenyl)ethynyl)-1H-pyrazolo[3,4-d]pyrimidin-1-yl)-2-(hydroxymethyl)pyrrolidine-1-carboxylate (2S,4S)-tert-butyl 4-(4-amino-3-((3,5-dimethoxyphenyl)ethynyl)-1H-pyrazolo[3,4-d]pyrimidin-1-yl)-2-((tert-butyldiphenylsilyloxy)methyl)pyrrolidine-1-carboxylate (25 mg) obtained in Step 4 above was dissolved in THF (1.0 ml). Silica gel-supported tetrabutylammonium fluolide (upto 1.5 mmol/g, 34 mg) was added thereto, followed by stirring overnight. Silica gel-supported tetrabutylammonium fluolide (upto 1.5 mmol/g, 30 mg) was further added thereto, and the mixture was further stirred for 2 days. After filtering the reagent off, the solvent was distilled off under reduced pressure. The resulting residue was purified by basic silica gel column chromatography (developing solvent: hexane/ethyl acetate) to obtain the title compound as a colorless, amorphous substance (62 mg). Physical properties: m/z[M+H]$^+$ 495.1

(Step 6) Synthesis of Compound of Example 28

In accordance with Example 1 (Step 4), except that 4-(4-amino-3-((3,5-dimethoxyphenyl)ethynyl)-1H-pyrazolo[3,4-d]pyrimidin-1-yl)-2-(hydroxymethyl)pyrrolidine-1-carboxylate obtained in Step 5 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 8 shows the physical properties thereof.

Example 29

Synthesis of 1-(3-((4-amino-3-((3,5-dimethoxyphenyl)ethynyl)-1H-pyrazolo[3,4-d]pyrimidin-1-yl)methyl)azetidin-1-yl)prop-2-en-1-one (Compound of Example 29)

In accordance with Example 26, except that 1-Boc-3-hydroxymethylazetidine was used in place of N-Boc-3-hydroxymethylpyrrolidine, the title compound was obtained as a light-yellow, amorphous substance. Table 8 shows the physical properties thereof.

Example 30

Synthesis of N-(3-(4-amino-3-((3,5-dimethoxyphenyl)ethynyl)-1H-pyrazolo[3,4-d]pyrimidin-1-yl)cyclobutyl)acrylamide (Compound of Example 30)

In accordance with Example 1, except that tert-butyl 3-hydroxycyclobutylcarbamate was used in place of N-Boc-3-hydroxypyrrolidine, the title compound was obtained as a light-yellow, amorphous substance. Table 8 shows the physical properties thereof.

Example 31

Synthesis of 1-(4-(4-amino-3-((3,5-dimethoxyphenyl)ethynyl)-1H-pyrazolo[3,4-d]pyrimidin-1-yl)piperidin-1-yl)prop-2-en-1-one (Compound of Example 31)

In accordance with Example 1, except that tert-butyl 4-bromopiperidin-1-carboxylate was used in place of tert-butyl 3-(methylsulfonyloxy)pyrrolidine-1-carboxylate, the title compound was obtained as a white solid. Table 8 shows the physical properties thereof.

Example 32

Synthesis of 1-((2S,4S)-4-(4-amino-3-((3,5-dimethoxyphenyl)ethynyl)-1H-pyrazolo[3,4-d]pyrimidin-1-yl)-2-ethynylpyrrolidin-1-yl)prop-2-en-1-one (Compound of Example 32)

(Step 1) Synthesis of (2S,4S)-tert-butyl 4-(4-amino-3-((3,5-dimethoxyphenyl)ethynyl)-1H-pyrazolo[3,4-d]pyrimidin-1-yl)-2-ethynylpyrrolidine-1-carboxylate 3-((3,5-Dimethoxyphenyl)ethynyl)-1H-pyrazolo[3,4-d]pyrimidin-4-amine (14 mg) obtained in Example 1 (Step 1), (2S,4R)-tert-butyl 2-ethynyl-4-hydroxypyrrolidine-1-carboxylate (15 mg) synthesized by the method disclosed in WO2005/007083, and triphenylphosphine (23 mg) were suspended in THF (1.0 ml). DIAD (18 μl) was added to the suspension, and the mixture was stirred at room temperature for 1 hour. The reaction mixture was concentrated and dissolved in a solution of DMSO. The resulting solution was purified by preparative reversed-phase HPLC purification (water/acetonitrile (0.1% formic acid)) to obtain the title compound as a colorless, amorphous substance (5.0 mg). Physical properties: m/z[M+H]$^+$ 489.2

(Step 2) Synthesis of Compound of Example 32

In accordance with Example 1 (Step 4), except that (2S,4S)-tert-butyl 4-(4-amino-3-((3,5-dimethoxyphenyl)ethynyl)-1H-pyrazolo[3,4-d]pyrimidin-1-yl)-2-ethynylpyrrolidine-1-carboxylate obtained in Step 1 above was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 9 shows the physical properties thereof.

Example 33

Synthesis of 1-(4-((4-amino-3-((3,5-dimethoxyphenyl)ethynyl)-1H-pyrazolo[3,4-d]pyrimidin-1-yl)methyl)piperidin-1-yl)prop-2-en-1-one (Compound of Example 33)

In accordance with Example 26, except that 1-Boc-4-hydroxymethylpiperidine was used in place of N-Boc-3-hydroxymethylpyrrolidine, the title compound was obtained as a light-yellow, amorphous substance. Table 9 shows the physical properties thereof.

Example 34

Synthesis of N-(3-((4-amino-3-((3,5-dimethoxyphenyl)ethynyl)-1H-pyrazolo[3,4-d]pyrimidin-1-yl)methyl)phenyl)acrylamide (Compound of Example 34)

In accordance with Example 26, except that (3-aminophenyl)methanol was used in place of N-Boc-3-hydroxymethylpyrrolidine, the title compound was obtained as a colorless, amorphous substance. Table 9 shows the physical properties thereof.

Example 35

Synthesis of 1-(3-((4-amino-3-((3,5-dimethoxyphenyl)ethynyl)-1H-pyrazolo[3,4-d]pyrimidin-1-yl)methyl)azetidin-1-yl)-4-(dimethylamino)but-2-en-1-one (Compound of Example 35)

In accordance with Example 4, except that 1-(azetidin-3-ylmethyl)-3-((3,5-dimethoxyphenyl)ethynyl)-1H-pyrazolo[3,4-d]pyrimidin-4-amine (i.e., the intermediate obtained in Example 29) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 9 shows the physical properties thereof.

Example 36

Synthesis of 1-(4-(4-amino-3-((3,5-dimethoxyphenyl)ethynyl)-1H-pyrazolo[3,4-d]pyrimidin-1-yl)piperidin-1-yl)-4-(dimethylamino)but-2-en-1-one (Compound of Example 36)

In accordance with Example 4, except that 3-((3,5-dimethoxyphenyl)ethynyl)-1-(piperidin-4-yl)-1H-pyrazolo[3,4-d]pyrimidin-4-amine (i.e., the intermediate obtained in Example 31) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 9 shows the physical properties thereof.

Example 37

Synthesis of 1-(4-((4-amino-3-((3,5-dimethoxyphenyl)ethynyl)-1H-pyrazolo[3,4-d]pyrimidin-1-yl)methyl)piperidin-1-yl)-4-(dimethylamino)but-2-en-1-one (Compound of Example 37)

In accordance with Example 4, except that 3-((3,5-dimethoxyphenyl)ethynyl)-1-(piperidin-4-ylmethyl)-1H-pyrazolo[3,4-d]pyrimidin-4-amine (i.e., the intermediate obtained in Example 33) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 10 shows the physical properties thereof.

Example 38

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(dimethylamino)but-2-en-1-one (Compound of Example 38)

(Step 1) Synthesis of (S)-tert-butyl 3-(4-chloro-5-iodo-7H-pyrrolo[2,3-d]pyrimidin-7-yl)pyrrolidine-1-carboxylate DIAD (1.41 ml) was added to a solution of 4-chloro-5-iodo-7H-pyrrolo[2,3-d]pyrimidine (1.00 g), (R)—N-Boc-3-pyrrolidinol (1.01 g), and triphenylphosphine (1.88 g) in tetrahydrofuran (40 ml), and the reaction mixture was stirred for 1 hour. The reaction mixture was concentrated and washed with ethyl acetate to obtain the title compound as a white solid (1.04 g). Physical properties: m/z[M+H]$^+$ 448.9

(Step 2) Synthesis of (S)-tert-butyl 3-(4-amino-5-iodo-7H-pyrrolo[2,3-d]pyrimidin-7-yl)pyrrolidine-1-carboxylate Tetrahydrofuran (2.5 ml) and 28% aqueous ammonia (2.5 ml) were added to (S)-tert-butyl 3-(4-chloro-5-iodo-7H-pyrrolo[2,3-d]pyrimidin-7-yl)pyrrolidine-1-carboxylate (400 mg) obtained in Step 1 above. The reaction mixture was stirred at 100° C. for 1.5 hours using a microwave reactor. Chloroform and water were added thereto to separate the organic layer. The organic layer was dried over anhydrous sodium sulfate, and the solvent was distilled off under reduced pressure to obtain the title compound as a white, solid compound (382 mg). Physical properties: m/z[M+H]$^+$ 430.3

(Step 3) Synthesis of (S)-tert-butyl 3-(4-amino-5-((3,5-dimethoxyphenyl)ethynyl)-7H-pyrrolo[2,3-d]pyrimidin-7-yl)pyrrolidine-1-carboxylate PdCl$_2$(dppf)$_2$CH$_2$Cl$_2$ (122 mg) was added to a mixture of (S)-tert-butyl 3-(4-amino-5-iodo-7H-pyrrolo[2,3-d]pyrimidin-7-yl)pyrrolidine-1-carboxylate (660 mg) obtained in Step 2 above, 1-ethynyl-3,5-dimethoxybenzene (374 mg), copper (I) iodide (44 mg), and triethylamine (2.0 ml) in THF (15 ml). After nitrogen purging, the resulting mixture was stirred at 80° C. for 3.5 hours. Ethyl acetate and water were added to the reaction mixture to separate the organic layer. After washing with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (714 mg). Physical properties: m/z[M+H]$^+$ 464.1

(Step 4) Synthesis of Compound of Example 38

4N-Hydrochloric acid/1,4-dioxane (2 ml) was added to the (S)-tert-butyl 3-(4-amino-5-((3,5-dimethoxyphenyl)ethynyl)-7H-pyrrolo[2,3-d]pyrimidin-7-yl)pyrrolidine-1-carboxylate (30 mg) obtained in Step 3 above, and the mixture was stirred at room temperature for 1.5 hours. After distilling the solvent of the resulting reaction mixture off under reduced pressure, toluene azeotropic distillation was subsequently performed to obtain a crude product of (S)-5-((3,5-dimethoxyphenyl)ethynyl)-7-(pyrrolidin-3-yl)-7H-pyrrolo[2,3-d]pyrimidin-4-amine (30 mg). A portion of the resulting crude product (10 mg), 4-(dimethylamino)but-2-enoic acid hydrochloride (5.9 mg), and HATU (14 mg) were dissolved in DMF (1.0 ml). DIPEA (50 µl) was added thereto and stirred at room temperature for 5 minutes. Chloroform and water were added to the reaction mixture to separate the organic layer. After being washed with a saturated sodium chloride solution, the organic layer was dried over anhydrous sodium sulfate, and the solvent was distilled off under reduced pressure. The resulting residue was purified by preparative reversed-phase HPLC purification (water/acetonitrile (0.1% formic acid)) to obtain the title compound as a colorless, amorphous substance (3.9 mg). Table 10 shows the physical properties thereof.

Example 39

Synthesis of (S)-1-(3-(4-amino-5-((3,5-dimethoxyphenyl)ethynyl)-7H-pyrrolo[2,3-d]pyrimidin-7-yl)pyrrolidin-1-yl)prop-2-en-1-one (Compound of Example 39)

In accordance with Example 1 (Step 4), except that (S)-tert-butyl 3-(4-amino-5-((3,5-dimethoxyphenyl)ethynyl)-7H-pyrrolo[2,3-d]pyrimidin-7-yl)pyrrolidine-1-carboxylate obtained in Example 38 (Step 3) was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of (S)-5-((3,5-dimethoxyphenyl)ethynyl)-7-(pyrrolidin-3-yl)-7H-pyrrolo[2,3-d]pyrimidin-4-amine was obtained by removing a Boc group under acidic conditions. Thereafter, amidation was conducted to obtain the title compound as a white solid. Table 10 shows the physical properties thereof.

Example 40

Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-(pyrrolidin-1-yl)but-2-en-1-one (Compound of Example 40)

(Step 1) Synthesis of 4-(pyrrolidin-1-yl)but-2-enoic acid hydrochloride

Methyl 4-bromocrotonate (1.79 g) was dissolved in tetrahydrofuran (40 ml), pyrrolidine (1.67 ml) was added thereto at 0° C., and the mixture was stirred at room temperature for 1 hour. Diethyl ether and water were added to the reaction mixture to separate the organic layer. After being washed with a saturated sodium chloride solution, the organic layer was dried over anhydrous sodium sulfate, and the solvent was distilled off under reduced pressure. 3N Hydrochloric acid (40 ml) was added to the resulting product, and the mixture was heated under reflux at 100° C. for 1 hour. The reaction mixture was concentrated under reduced pressure, and then the resulting residue was washed with a mixed solvent of isopropanol and ethyl acetate to obtain the title compound as a white solid (939 mg). Physical properties: m/z[M+H]$^+$ 156.0

(Step 2) Synthesis of Compound of Example 40

In accordance with Example 4 (Step 1), except that (5)-5-((3,5-dimethoxyphenyl)ethynyl)-7-(pyrrolidin-3-yl)-7H-pyrrolo[2,3-d]pyrimidin-4-amine (the intermediate obtained in Example 38 (Step 4)) and 4-(pyrrolidin-1-yl)but-2-enoic acid hydrochloride obtained in Step 1 above were used, the title compound was obtained as a colorless, amorphous substance. Table 10 shows the physical properties thereof.

Example 41

Synthesis of (S)-1-(3-(4-amino-5-((3,5-dimethoxyphenyl)ethynyl)-7H-pyrrolo[2,3-d]pyrimidin-7-yl) pyrrolidin-1-yl)-4-(4-methylpiperazin-1-yl)but-2-en-1-one (Compound of Example 41)

(Step 1) Synthesis of (S)-1-(3-(4-amino-5-((3,5-dimethoxyphenyl)ethynyl)-7H-pyrrolo[2,3-d]pyrimidin-7-yl)pyrrolidin-1-yl)-4-bromobut-2-en-1-one The crude product (100 mg) of (S)-5-((3,5-dimethoxyphenyl)ethynyl)-7-(pyrrolidin-3-yl)-7H-pyrrolo[2,3-d]pyrimidin-4-amine (i.e., the intermediate obtained in Example 38 (Step 4)) was suspended in chloroform (3.0 ml). DIPEA (117 μl) was added to the suspension, and the mixture was cooled to 0° C. A solution of 4-bromobut-2-enoyl chloride (46 mg) obtained in Example 16 (Step 1) in chloroform (0.3 ml) was added thereto dropwise, and the resulting mixture was stirred at room temperature for 15 minutes. After halting the reaction using a saturated aqueous sodium bicarbonate solution, the resulting product was extracted with ethyl acetate. The organic layer was dried over anhydrous sodium sulfate, and the solvent was distilled off under reduced pressure to obtain the title compound as a crude product (140 mg). Physical properties: m/z[M+H]$^+$ 509.9, 511.9

(Step 2) Synthesis of Compound of Example 41

The crude product (12 mg) of (S)-1-(3-(4-amino-5-((3,5-dimethoxyphenyl)ethynyl)-7H-pyrrolo[2,3-d]pyrimidin-7-yl)pyrrolidin-1-yl)-4-bromobut-2-en-1-one obtained in Step 1 above was dissolved in DMF (0.5 ml). N-methylpiperazine (4 mg) and DIPEA (10 μl) were added thereto, followed by stirring at room temperature overnight. After concentrating under reduced pressure, the resulting residue was purified by preparative reversed-phase HPLC purification (water/acetonitrile (0.1% formic acid)) to obtain the title compound as a colorless, amorphous substance (3.0 mg). Table 11 shows the physical properties thereof.

Example 42

Synthesis of (S)-1-(3-(4-amino-5-((3,5-dimethoxyphenyl)ethynyl)-7H-pyrrolo[2,3-d]pyrimidin-7-yl) pyrrolidin-1-yl)-4-(4-hydroxypiperidin-1-yl)but-2-en-1-one (Compound of Example 42)

In accordance with Example 41 (Step 2), except that 4-hydroxypiperidine was used in place of N-methylpiperazine, the title compound was obtained as a colorless, amorphous substance. Table 11 shows the physical properties thereof.

Example 43

Synthesis of (S)-1-(3-(4-amino-5-((3,5-dimethoxyphenyl)ethynyl)-7H-pyrrolo[2,3-d]pyrimidin-7-yl) pyrrolidin-1-yl)-4-(4-fluoropiperidin-1-yl)but-2-en-1-one (Compound of Example 43)

In accordance with Example 41 (Step 2), except that 4-fluoropiperidine was used in place of N-methylpiperazine, the title compound was obtained as a colorless, amorphous substance. Table 11 shows the physical properties thereof.

Example 44

Synthesis of (S)-1-(3-(4-amino-5-((3,5-dimethoxyphenyl)ethynyl)-7H-pyrrolo[2,3-d]pyrimidin-7-yl) pyrrolidin-1-yl)-4-(3,3-difluoropyrrolidin-1-yl)but-2-en-1-one (Compound of Example 44)

In accordance with Example 41 (Step 2), except that 3,3-difluoropyrrolidine was used in place of N-methylpiperazine, the title compound was obtained as a colorless, amorphous substance. Table 12 shows the physical properties thereof.

Example 45

Synthesis of (S)-1-(3-(4-amino-5-((3,5-dimethoxyphenyl)ethynyl)-7H-pyrrolo[2,3-d]pyrimidin-7-yl) pyrrolidin-1-yl)-4-(4,4-difluoropiperidin-1-yl)but-2-en-1-one (Compound of Example 45)

In accordance with Example 41 (Step 2), except that 4,4-difluoropiperidine was used in place of N-methylpiperazine, the title compound was obtained as a colorless, amorphous substance. Table 12 shows the physical properties thereof.

Example 46

Synthesis of (S)-1-(3-(4-amino-5-((3,5-dimethoxyphenyl)ethynyl)-7H-pyrrolo[2,3-d]pyrimidin-7-yl) pyrrolidin-1-yl)but-2-yn-1-one (Compound of Example 46)

In accordance with Example 4 (Step 1), except that (5)-5-((3,5-dimethoxyphenyl)ethynyl)-7-(pyrrolidin-3-yl)-7H-pyrrolo[2,3-d]pyrimidin-4-amine (i.e., the intermediate obtained in Example 38 (Step 4)) and 2-butynoic acid were used, the title compound was obtained as a colorless, amorphous substance. Table 12 shows the physical properties thereof.

Example 47

Synthesis of (S)-1-(3-(4-amino-5-((3,5-dimethoxyphenyl)ethynyl)-7H-pyrrolo[2,3-d]pyrimidin-7-yl) pyrrolidin-1-yl)-4-hydroxy-4-methylpent-2-yn-1-one (Compound of Example 47)

In accordance with Example 4 (Step 1), except that (5)-5-((3,5-dimethoxyphenyl)ethynyl)-7-(pyrrolidin-3-yl)-7H-pyrrolo[2,3-d]pyrimidin-4-amine (i.e., the intermediate obtained in Example 38 (Step 4)) and 4-hydroxy-4-methyl-pent-2-ynoic acid were used, the title compound was obtained as a colorless, amorphous substance. Table 12 shows the physical properties thereof.

Example 48

Synthesis of 1-((S)-3-(4-amino-5-((3,5-dimethoxy-phenyl)ethynyl)-7H-pyrrolo[2,3-d]pyrimidin-7-yl)pyrrolidin-1-yl)-4-((R)-3-fluoropyrrolidin-1-yl)but-2-en-1-one (Compound of Example 48)

In accordance with Example 41 (Step 2), except that (R)-3-fluoropyrrolidine was used in place of N-methylpiperazine, the title compound was obtained as a colorless, amorphous substance. Table 13 shows the physical properties thereof.

Example 49

Synthesis of 1-((5)-3-(4-amino-5-((3,5-dimethoxy-phenyl)ethynyl)-7H-pyrrolo[2,3-d]pyrimidin-7-yl)pyrrolidin-1-yl)-4-((S)-3-fluoropyrrolidin-1-yl)but-2-en-1-one (Compound of Example 49)

In accordance with Example 41 (Step 2), except that (S)-3-fluoropyrrolidine was used in place of N-methylpiperazine, the title compound was obtained as a colorless, amorphous substance. Table 13 shows the physical properties thereof.

Example 50

Synthesis of (S)-1-(3-(4-amino-5-((3,5-dimethoxy-phenyl)ethynyl)-7H-pyrrolo[2,3-d]pyrimidin-7-yl)pyrrolidin-1-yl)-4-(piperidin-1-yl)but-2-en-1-one (Compound of Example 50)

In accordance with Example 41 (Step 2), except that piperidine was used in place of N-methylpiperazine, the title compound was obtained as a colorless, amorphous substance. Table 13 shows the physical properties thereof.

Example 51

Synthesis of 1-(3-(4-amino-5-((3,5-dimethoxyphenyl)ethynyl)-7H-pyrrolo[2,3-d]pyrimidin-7-yl)azetidin-1-yl)prop-2-en-1-one (Compound of Example 51)

(Step 1) Synthesis of tert-butyl 3-(4-chloro-5-iodo-7H-pyrrolo[2,3-d]pyrimidin-7-yl)azetidine-1-carboxylate DIAD (1.41 ml) was added to a solution of 4-chloro-5-iodo-7H-pyrrolo[2,3-d]pyrimidine (1.00 g), N-Boc-3-hydroxyazetidine (930 mg), and triphenylphosphine (1.85 g) in tetrahydrofuran (40 ml), and the reaction mixture was stirred for 1 hour. After concentrating, the reaction mixture was washed with ethyl acetate to obtain the title compound as a white solid (1.07 g). Physical properties: m/z[M+H]$^+$ 435.0

(Step 2) Synthesis of tert-butyl 3-(4-amino-5-iodo-7H-pyrrolo[2,3-d]pyrimidin-7-yl)azetidine-1-carboxylate Tetrahydrofuran (2.5 ml) and 28% aqueous ammonia (2.5 ml) were added to the tert-butyl 3-(4-chloro-5-iodo-7H-pyrrolo[2,3-d]pyrimidin-7-yl)azetidine-1-carboxylate (350 mg) obtained in Step 1 above. The reaction mixture was stirred at 100° C. for 1.5 hours using a microwave reactor. Chloroform and water were added thereto to separate the organic layer. The organic layer was dried over anhydrous sodium sulfate, and the solvent was distilled off under reduced pressure to obtain the title compound as a white solid (340 mg). Physical properties: m/z[M+H]$^+$ 416.0

(Step 3) Synthesis of tert-butyl 3-(4-amino-5-((3,5-dimethoxyphenyl)ethynyl)-7H-pyrrolo[2,3-d]pyrimidin-7-yl)azetidine-1-carboxylate PdCl$_2$(dppf)CH$_2$Cl$_2$ (122 mg) was added to a mixture of tert-butyl 3-(4-amino-5-iodo-7H-pyrrolo[2,3-d]pyrimidin-7-yl)azetidine-1-carboxylate (639 mg) obtained in Step 2 above, 1-ethynyl-3,5-dimethoxybenzene (374 mg), copper (I) iodide (44 mg), and triethylamine (2.0 ml) in THF (15 ml). After nitrogen purging, the resulting mixture was stirred at 80° C. for 3.5 hours. Ethyl acetate and water were added to the reaction mixture to separate the organic layer. After being washed with a saturated sodium chloride solution, the organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (704 mg). Physical properties: m/z[M+H]$^+$ 450.1

(Step 4) Synthesis of Compound of Example 51

In accordance with Example 1 (Step 4), except that tert-butyl 3-(4-amino-5-((3,5-dimethoxyphenyl)ethynyl)-7H-pyrrolo[2,3-d]pyrimidin-7-yl)azetidine-1-carboxylate obtained in Step 3 was used in place of tert-butyl 3-(4-amino-3-((3,5-dimethoxyphenyl)ethynyl)-1H-pyrazolo[3,4-d]pyrimidin-1-yl)pyrrolidine-1-carboxylate, a crude product of 7-(azetidin-3-y)-5-((3,5-)dimethoxyphenyl)ethynyl)-7H-pyrrolo[2,3-d]pyrimidin-4-amine was obtained by removing a Boc group under acidic conditions. Thereafter, amidation was conducted to obtain the title compound as a white solid. Table 13 shows the physical properties thereof.

Example 52

Synthesis of 1-(3-(4-amino-5-((3,5-dimethoxyphenyl)ethynyl)-7H-pyrrolo[2,3-d]pyrimidin-7-yl)azetidin-1-yl)-4-(dimethylamino)but-2-en-1-one (Example Compound 52)

In accordance with Example 4 (Step 1), except that the tert-butyl 3-(4-amino-5-((3,5-dimethoxyphenyl)ethynyl)-7H-pyrrolo[2,3-d]pyrimidin-7-yl)azetidine-1-carboxylate obtained in Example 51 (Step 3) was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a colorless, amorphous substance. Table 14 shows the physical properties thereof.

Example 53

Synthesis of 1-(3-(4-amino-5-((3,5-dimethoxyphenyl)ethynyl)-7H-pyrrolo[2,3-d]pyrimidin-7-yl)azetidin-1-yl)-4-(pyrrolidin-1-yl)but-2-en-1-one (Example Compound 53)

In accordance with Example 4 (Step 1), the 7-(azetidin-3-yl)-5-((3,5-)dimethoxyphenyl)ethynyl)-7H-pyrrolo[2,3-d]

pyrimidin-4-amine obtained in Example 51 (Step 4) as an intermediate, and the 4-(pyrrolidin-1-yl)but-2-enoic acid hydrochloride obtained in Example 40 (Step 1) were used to obtain the title compound as a colorless, amorphous substance. Table 14 shows the physical properties thereof.

Example 54

Synthesis of 1-(3-(4-amino-5-((3,5-dimethoxyphenyl)ethynyl)-7H-pyrrolo[2,3-d]pyrimidin-7-yl)azetidin-1-yl)but-2-yn-1-one (Example Compound 54)

In accordance with Example 4 (Step 1), the 7-(azetidin-3-yl)-5-((3,5-)dimethoxyphenyl)ethynyl)-7H-pyrrolo[2,3-d]pyrimidin-4-amine obtained as an intermediate in Example 51 (Step 4) and 2-butynoic acid were used to obtain the title compound as a colorless, amorphous substance. Table 14 shows the physical properties thereof.

Example 55

Synthesis of 1-(3-(4-amino-5-((3,5-dimethoxyphenyl)ethynyl)-7H-pyrrolo[2,3-d]pyrimidin-7-yl)azetidin-1-yl)-4-(azetidin-1-yl)but-2-en-1-one (Example Compound 55)

(Step 1) Synthesis of 1-(3-(4-amino-5-((3,5-dimethoxyphenyl)ethynyl)-7H-pyrrolo[2,3-d]pyrimidin-7-yl)azetidin-1-yl)-4-bromobut-2-en-1-one A crude product of 7-(azetidin-3-yl)-5-((3,5-dimethoxyphenyl)ethynyl)-7H-pyrrolo[2,3-d]pyrimidin-4-amine (160 mg) obtained in Example 52 (Step 4) as an intermediate was suspended in THF (3.0 ml). DIPEA (202 µl) was added thereto, and the mixture was cooled to 0° C. A solution of 4-bromobut-2-enoyl chloride (75 mg) obtained in Example 16 (Step 1) in THF (0.5 ml) was added to the mixture dropwise, and stirred at room temperature for 15 minutes. After halting the reaction using a saturated sodium bicarbonate solution, the resulting product was extracted with ethyl acetate. After drying the result over anhydrous sodium sulfate, the solvent was distilled off under reduced pressure to obtain the title compound as a crude product (204 mg). Physical properties: m/z[M+H]$^+$ 496.0, 498.0

(Step 2) Synthesis of Example Compound 55

The crude product of 1-(3-(4-amino-5-((3,5-dimethoxyphenyl)ethynyl)-7H-pyrrolo[2,3-d]pyrimidin-7-yl)azetidin-1-yl)-4-bromobut-2-en-1-one (10 mg) obtained in Step 1 above was suspended in THF (0.5 ml). Azetidine (7 µl) was added thereto, and the resulting mixture was stirred for 1 hour at room temperature. After concentrating under reduced pressure, the resulting residue was purified by reversed-phase HPLC purification (water/acetonitrile (0.1% formic acid)) to obtain the title compound as a colorless, amorphous substance (1.6 mg). Table 14 shows the physical properties thereof.

Example 56

Synthesis of 1-(3-(4-amino-5-((3,5-dimethoxyphenyl)ethynyl)-7H-pyrrolo[2,3-d]pyrimidin-7-yl)azetidin-1-yl)-4-(ethyl(methyl)amino)but-2-en-1-one (Example Compound 56)

In accordance with Example 55 (Step 2), except that ethylmethylamine was used in place of azetidine, the title compound was obtained as a colorless, amorphous substance. Table 15 shows the physical properties thereof.

Example 57

Synthesis of 1-(3-(4-amino-5-((3,5-dimethoxyphenyl)ethynyl)-7H-pyrrolo[2,3-d]pyrimidin-7-yl)azetidin-1-yl)-4-(isopropylamino)but-2-en-1-one (Example Compound 57)

In accordance with Example 55 (Step 2), except that isopropylamine was used in place of azetidine, the title compound was obtained as a colorless, amorphous substance. Table 15 shows the physical properties thereof.

Example 58

Synthesis of 1-(3-(4-amino-5-((3,5-dimethoxyphenyl)ethynyl)-7H-pyrrolo[2,3-d]pyrimidin-7-yl)azetidin-1-yl)-4-(isopropyl(methyl)amino)but-2-en-1-one (Example Compound 58)

In accordance with Example 55 (Step 2), except that isopropylmethylamine was used in place of azetidine, the title compound was obtained as a colorless, amorphous substance. Table 15 shows the physical properties thereof.

Example 59

Synthesis of 1-(3-(4-amino-5-((3,5-dimethoxyphenyl)ethynyl)-7H-pyrrolo[2,3-d]pyrimidin-7-yl)azetidin-1-yl)-4-(diethylamino)but-2-en-1-one (Example Compound 59)

In accordance with Example 55 (Step 2), except that diethylamine was used in place of azetidine, the title compound was obtained as a colorless, amorphous substance. Table 16 shows the physical properties thereof.

Example 60

Synthesis of 1-(3-(4-amino-5-((3,5-dimethoxyphenyl)ethynyl)-7H-pyrrolo[2,3-d]pyrimidin-7-yl)azetidin-1-yl)-4-((2-methoxyethyl)(methyl)amino)but-2-en-1-one (Example Compound 60)

In accordance with Example 55 (Step 2), except that 2-methoxy-N-methylethanamine was used in place of azetidine, the title compound was obtained as a colorless, amorphous substance. Table 16 shows the physical properties thereof.

Example 61

Synthesis of 1-(3-(4-amino-5-((3,5-dimethoxyphenyl)ethynyl)-7H-pyrrolo[2,3-d]pyrimidin-7-yl)azetidin-1-yl)-4-(4-hydroxypiperidin-1-yl)but-2-en-1-one (Example Compound 61)

In accordance with Example 55 (Step 2), except that 4-hydroxypiperidin was used in place of azetidine, the title compound was obtained as a colorless, amorphous substance. Table 16 shows the physical properties thereof.

Example 62

Synthesis of (S)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Example Compound 62)

In accordance with Example 55 (Step 2), except that (S)-3-hydroxypyrrolidine was used in place of azetidine, the title compound was obtained as a colorless, amorphous substance. Table 17 shows the physical properties thereof.

Example 63

Synthesis of (R)-1-(3-(4-amino-5-((3,5-dimethoxyphenyl)ethynyl)-7H-pyrrolo[2,3-d]pyrimidin-7-yl)azetidin-1-yl)-4-(3-hydroxypyrrolidin-1-yl)but-2-en-1-one (Example Compound 63)

In accordance with Example 55 (Step 2), except that (R)-3-hydroxypyrrolidine was used in place of azetidine, the title compound was obtained as a colorless, amorphous substance. Table 17 shows the physical properties thereof.

Example 64

Synthesis of 1-(4-(4-amino-5-((3,5-dimethoxyphenyl)ethynyl)-7H-pyrrolo[2,3-d]pyrimidin-7-yl)piperidin-1-yl)prop-2-en-1-one (Example Compound 64)

In accordance with Example 39, except that N-Boc-4-piperidinol was used in place of (R)—N-Boc-3-pyrrolidinol, the title compound was obtained as a light-yellow, amorphous substance. Table 17 shows the physical properties thereof.

Example 65

Synthesis of 1-(4-(4-amino-5-((3,5-dimethoxyphenyl)ethynyl)-7H-pyrrolo[2,3-d]pyrimidin-7-yl)piperidin-1-yl)-4-(dimethylamino)but-2-en-1-one (Example Compound 65)

In accordance with Example 38, except that N-Boc-4-piperidinol was used in place of (R)—N-Boc-3-pyrrolidinol, the title compound was obtained as a light-yellow, amorphous substance. Table 17 shows the physical properties thereof.

Example 66

Synthesis of (2S,4S)-methyl 1-acryloyl-4-(4-amino-5-((3,5-dimethoxyphenyl)ethynyl)-7H-pyrrolo[2,3-d]pyrimidin-7-yl)pyrrolidine-2-carboxylate (Example Compound 66)

(Step 1) Synthesis of 4-chloro-5-iodo-7-((2-(trimethylsilyl)ethoxy)methyl)-7H-pyrrolo[2,3-d]pyrimidine 4-Chloro-5-iodo-7H-pyrrolo[2,3-d]pyrimidine (7.01 g) synthesized by the method disclosed in WO2005/042556 was dissolved in anhydrous THF (125 ml). After cooling to 0° C., 60% sodium hydride (4.02 g) was added to the result, and the resulting mixture was stirred for 20 minutes. Subsequently, SEMCl (13.3 ml) was added thereto, and the mixture was stirred at room temperature overnight. After cooling to 0° C. again, water was added to the mixture, and the reaction was halted. The resulting product was extracted with ethyl acetate, and the organic layer was washed with a saturated sodium chloride solution. After drying the result over anhydrous sodium sulfate, the solvent was distilled off under reduced pressure. The resulting residue was purified by silica gel column chromatography (developing solvent: hexane/ethyl acetate) to obtain the title compound as a white solid (7.28 g). Physical properties: m/z[M+H]$^+$ 410.0

(Step 2) Synthesis of 5-iodo-7-((2-(trimethylsilyl)ethoxy)methyl)-7H-pyrrolo[2,3-d]pyrimidin-4-amine The 4-chloro-5-iodo-7-((2-(trimethylsilyl)ethoxy)methyl)-7H-pyrrolo[2,3-d]pyrimidine (200 mg) obtained in Step 1 above was dissolved in THF (2.0 ml). 28% Aqueous ammonia (2 ml) was added thereto, and the reaction mixture was then stirred at 105° C. for 1.5 hours using a microwave reactor. The resulting product was extracted with ethyl acetate, and the organic layer was washed with a saturated sodium chloride solution. After drying the result over anhydrous sodium sulfate, the solvent was distilled off under reduced pressure to obtain the title compound as a white solid (192 mg). Physical properties: m/z[M+H]$^+$ 391.0

(Step 3) Synthesis of 5-((3,5-dimethoxyphenyl)ethynyl)-7-((2-(trimethylsilyl)ethoxy)methyl)-7H-pyrrolo[2,3-d]pyrimidin-4-amine In accordance with Example 1 (Step 1), except that the 5-iodo-7-((2-(trimethylsilyl)ethoxy)methyl)-7H-pyrrolo[2,3-d]pyrimidin-4-amine obtained in Step 2 above was used in place of 3-iodo-1H-pyrazolo[3,4-d]pyrimidin-4-amine, the title compound was obtained as a colorless solid. Physical properties: m/z[M+H]$^+$ 425.4

(Step 4) Synthesis of 5-((3,5-dimethoxyphenyl)ethynyl)-7H-pyrrolo[2,3-d]pyrimidin-4-amine A solution of 5-((3,5-dimethoxyphenyl)ethynyl)-7-((2-(trimethylsilyl)ethoxy)methyl)-7H-pyrrolo[2,3-d]pyrimidin-4-amine (4.27 g) obtained in Step 3 in methylene chloride (20 ml) was cooled to 0° C., and TFA (10 ml) was added thereto. The reaction mixture was stirred at room temperature for 5 hours, and the solvent was distilled off under reduced pressure. THF (50 ml) was added to the residue, and the mixture was cooled to 0° C. 4N aqueous sodium hydroxide (12.5 ml) was added thereto, and the mixture was stirred at room temperature overnight. The result was extracted with ethyl acetate, and dried over anhydrous magnesium sulfate. Subsequently, the solvent was distilled off under reduced pressure, and chloroform was added to the resulting residue. The mixture was subjected to filtration to obtain the title compound as a white solid (2.60 g). Physical properties: m/z[M+H]$^+$ 295.3

(Step 5) Synthesis of (2S,4R)-4-(methylsulfonyloxy)-pyrrolidine-1,2-dicarboxylic acid 1-tert-butylester-2-methylester In accordance with Example 1 (Step 2), except that (2S,4R)-4-hydroxy-pyrrolidine-1,2-dicarboxylic acid 1-tertbutylester-2-methylester was used in place of N-Boc-3-pyrrolidinol, the title compound was obtained as a colorless, amorphous substance.

(Step 6) Synthesis of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate In accordance with Example 1 (Step 3), except that the 5-((3,5-dimethoxyphenyl)ethynyl)-7H-pyrrolo[2,3-d]pyrimidin-4-amine obtained in Step 4, the (2S,4R)-4-(methylsulfonyloxy)-pyrrolidine-1,2-dicarboxylic acid 1-tert-butylester-2-methylester obtained in Step 5, sodium hydride, and NMP were individually used in place of 3-((3,5-dimethoxyphenyl)ethynyl)-1H-pyrazolo[3,4-d]pyrimidin-4-amine, tert-butyl 3-(methylsulfonyloxy)pyrrolidine-1-carboxylate, potassium carbonate, and DMF, the title compound was obtained as a colorless, amorphous substance. Physical properties: m/z[M+H]$^+$ 522.4

(Step 7) Synthesis of (2S,4S)-methyl 4-(4-amino-5-((3,5-dimethoxyphenyl)ethynyl)-7H-pyrrolo[2,3-d]pyrimidin-7-yl)pyrrolidine-2-carboxylate A solution of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate (24 mg) obtained in Step 6 above in methylene chloride (2.0 ml) and TFA (2.0 ml) was stirred at room temperature for 30 minutes. The solvent was distilled off under reduced pressure, and the resulting residue was purified by basic silica gel column chromatography (developing solvent: chloroform/methanol). The title compound was thus obtained as a light-yellow, amorphous substance (11.9 mg). Physical properties: m/z[M+H]$^+$ 422.1

(Step 8) Synthesis of Example Compound 66

Methylene chloride (2.0 ml) and triethylamine (16 μl) were added to the (2S,4S)-methyl 4-(4-amino-5-((3,5-dimethoxyphenyl)ethynyl)-7H-pyrrolo[2,3-d]pyrimidin-7-yl)pyrrolidine-2-carboxylate (12 mg) obtained in Step 7 above. After cooling to 0° C., chloroform (100 μl) in which acryloyl chloride (5 μl) was dissolved was added to the resulting mixture, and stirred at room temperature for 10 minutes. After halting the reaction using a saturated sodium bicarbonate solution, the resulting product was extracted with ethyl acetate. After drying the result over anhydrous sodium sulfate, the solvent was distilled off under reduced pressure. The resulting residue was purified by silica gel column chromatography (developing solvent: ethyl acetate/methanol) to obtain the title compound as a colorless, amorphous substance (4.2 mg). Table 18 shows the physical properties thereof.

Example 67

Synthesis of 1-((2S,4S)-4-(4-amino-5-((3,5-dimethoxyphenyl)ethynyl)-7H-pyrrolo[2,3-d]pyrimidin-7-yl)-2-((dimethylamino)methyl)pyrrolidin-1-yl)prop-2-en-1-one (Example Compound 67)

(Step 1) Synthesis of (2S,4S)-tert-butyl 2-((tert-butyldiphenylsilyloxy)methyl)-4-(4-chloro-5-iodo-7H-pyrrolo[2,3-d]pyrimidin-7-yl)pyrrolidine-1-carboxylate A solution of triphenylphosphine (443 mg) in THF (25 ml) was cooled to 0° C., and DIAD (340 μl) was added thereto dropwise. The reaction mixture was stirred at 0° C. for 1 hour. 4-Chloro-5-iodo-7H-pyrrolo[2,3-d]pyrimidine (363 mg) and the (2S,4R)-tert-butyl 2-((tert-butyldiphenylsilyloxy)methyl)-4-hydroxypyrrolidine-1-carboxylate (651.6 mg) obtained in Example 28 (Step 1) were added thereto, and stirred at room temperature overnight. Ethyl acetate and water were added to separate the organic layer. The organic layer was dried over anhydrous magnesium sulfate, and the solvent was distilled off under reduced pressure. The resulting residue was purified by silica gel column chromatography (developing solvent: hexane/ethyl acetate) to obtain the title compound as a light-yellow, amorphous substance (400 mg). m/z[M+H]$^+$ 718.5

(Step 2) Synthesis of (2S,4S)-tert-butyl 4-(4-amino-5-iodo-7H-pyrrolo[2,3-d]pyrimidin-7-yl)-2-((tert-butyldiphenylsilyloxy)methyl)pyrrolidine-1-carboxylate THF (10 ml) and an 8N ammonia methanol solution (5 ml) were added to the (2S,4S)-tert-butyl 2-((tert-butyldiphenylsilyloxy)methyl)-4-(4-chloro-5-iodo-7H-pyrrolo[2,3-d]pyrimidin-7-yl)pyrrolidine-1-carboxylate (400 mg) obtained in Step 1. The mixture was stirred at 120° C. for 2 hours under microwave irradiation, and the solvent was distilled off under reduced pressure. The resulting residue was purified by silica gel column chromatography (developing solvent: chloroform/ethanol) to obtain the title compound as a light-yellow solid (293 mg). Physical properties: m/z[M+H]$^+$ 698.5

(Step 3) Synthesis of (2S,4S)-tert-butyl 4-(4-(bis(tert-butoxycarbonyl)amino)-5-iodo-7H-pyrrolo[2,3-d]pyrimidin-7-yl)-2-((tert-butyldiphenylsilyloxy)methyl)pyrrolidine-1-carboxylate Boc$_2$O (188 mg) and DMAP (7 mg) were added to a solution of (2S,4S)-tert-butyl 4-(4-amino-5-iodo-7H-pyrrolo[2,3-d]pyrimidin-7-yl)-2-((tert-butyldiphenylsilyloxy)methyl)pyrrolidine-1-carboxylate (200 mg) obtained in Step 2 in THF (5 ml), and the resulting mixture was stirred at room temperature overnight. Ethyl acetate and water were added to the reaction mixture to separate the organic layer. The organic layer was dried over anhydrous magnesium sulfate, and the solvent was distilled off under reduced pressure. The resulting residue was purified by silica gel column chromatography (developing solvent: hexane/ethyl acetate) to obtain the title compound as a light-yellow, amorphous substance (238 mg). m/z[M+H]$^+$ 898.5

(Step 4) Synthesis of (2S,4S)-tert-butyl 4-(4-(bis(tert-butoxycarbonyl)amino)-5-iodo-7H-pyrrolo[2,3-d]pyrimidin-7-yl)-2-(hydroxymethyl)pyrrolidine-1-carboxylate Silica gel-carrying tetrabutyl ammonium fluoride (700 mg) (up to 1.5 mmol/g) was added to a solution of (2S,4S)-tert-butyl 4-(4-(bis(tert-butoxycarbonyl)amino)-5-iodo-7H-pyrrolo[2,3-d]pyrimidin-7-yl)-2-((tert-butyldiphenylsilyloxy)methyl)pyrrolidine-1-carboxylate (237.5 mg) obtained in Step 3 in THF (5 ml), and the resulting mixture was stirred at room temperature overnight. Silica gel was separated by filtration, and the solvent of the filtrate was distilled off under reduced pressure. The resulting residue was purified by silica gel column chromatography (developing solvent:

hexane/ethyl acetate) to obtain the title compound as a light-yellow, amorphous substance (185 mg). Physical properties: m/z [M+H]+ 660.2

(Step 5) Synthesis of (2S,4S)-tert-butyl 4-(4-(bis(tert-butoxycarbonyl)amino)-5-iodo-7H-pyrrolo[2,3-d]pyrimidin-7-yl)-2-formylpyrrolidine-1-carboxylate Dess-Martin periodinane (51 mg) was added to a solution of (2S,4S)-tert-butyl 4-(4-(bis(tert-butoxycarbonyl)amino)-5-iodo-7H-pyrrolo[2,3-d]pyrimidin-7-yl)-2-(hydroxymethyl)pyrrolidine-1-carboxylate (66 mg) obtained in Step in methylene chloride (2 ml), and the resulting mixture was stirred at room temperature for 1 hour. Dess-Martin periodinane (100 mg) was further added to the mixture, and stirred at room temperature for 1 hour. Dess-Martin periodinane (70 mg) was additionally added thereto, and the resulting mixture was stirred at room temperature for 1 hour. Water was added to the reaction mixture to separate the organic layer. The organic layer was washed with a sodium hydrogen carbonate aqueous solution and a 10% sodium thiosulfate aqueous solution, and dried over anhydrous sodium sulfate. The solvent was distilled off under reduced pressure to obtain the title compound as a light-yellow, amorphous substance (68 mg). Physical properties: m/z[M+H]+ 658.1

(Step 6) Synthesis of (2S,4S)-tert-butyl 4-(4-(bis(tert-butoxycarbonyl)amino)-5-iodo-7H-pyrrolo[2,3-d]pyrimidin-7-yl)-2-((dimethylamino)methyl)pyrrolidine-1-carboxylate A 1M dimethylamine THF solution (0.3 ml) and acetic acid (0.2 ml) were added to a solution of (2S,4S)-tert-butyl 4-(4-(bis(tert-butoxycarbonyl)amino)-5-iodo-7H-pyrrolo[2,3-d]pyrimidin-7-yl)-2-formylpyrrolidine-1-carboxylate (68 mg) obtained in Step 5 in methylene chloride (2 ml), and the resulting mixture was cooled to 0° C. Sodium triacetoxyborohydride (127 mg) was added to the reaction mixture, and stirred at 0° C. for 2 hours. The reaction mixture was neutralized using a sodium hydrogen carbonate aqueous solution, and the organic layer was dried over anhydrous sodium sulfate. The solvent was distilled off under reduced pressure to obtain the title compound as a light-yellow, amorphous substance (31.9 mg). Physical properties: m/z [M+H]+ 687.2

(Step 7) Synthesis of (2S,4S)-tert-butyl 4-(4-(bis(tert-butoxycarbonyl)amino)-5-((3,5-dimethoxyphenyl)ethynyl)-7H-pyrrolo[2,3-d]pyrimidin-7-yl)-2-((dimethylamino)methyl)pyrrolidine-1-carboxylate In accordance with Example 1 (Step 1), except that the (2S,4S)-tert-butyl 4-(4-(bis(tert-butoxycarbonyl)amino)-5-iodo-7H-pyrrolo[2,3-d]pyrimidin-7-yl)-2-((dimethylamino)methyl)pyrrolidine-1-carboxylate obtained in Step 6 was used in place of 3-iodo-1H-pyrazolo[3,4-d]pyrimidin-4-amine, the title compound was obtained as a light-yellow, amorphous substance. Physical properties: m/z[M+H]+ 721.5

(Step 8) Synthesis of 5-((3,5-dimethoxyphenyl)ethynyl)-7-((3S,5S)-5-((dimethylamino)methyl)pyrrolidin-3-yl)-7H-pyrrolo[2,3-d]pyrimidin-4-amine In accordance with Example 66 (Step 7), except that the (2S,4S)-tert-butyl 4-(4-(bis(tert-butoxycarbonyl)amino)-5-((3,5-dimethoxyphenyl)ethynyl)-7H-pyrrolo[2,3-d]pyrimidin-7-yl)-2-((dimethylamino)methyl)pyrrolidine-1-carboxylate obtained in Step 7 was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance. Physical properties: m/z[M+H]+ 421.1

(Step 9) Synthesis of Example Compound 67

In accordance with Example 66 (Step 8), except that the 5-((3,5-dimethoxyphenyl)ethynyl)-7-((3S,5S)-5-((dimethylamino)methyl)pyrrolidin-3-yl)-7H-pyrrolo[2,3-d]pyrimidin-4-amine obtained in Step 8 was used in place of (2S,4S)-methyl 4-(4-amino-5-((3,5-dimethoxyphenyl)ethynyl)-7H-pyrrolo[2,3-d]pyrimidin-7-yl)pyrrolidine-2-carboxylate, the title compound was obtained as a colorless, amorphous substance. Table 18 shows the physical properties thereof.

Example 68

Synthesis of 1-((2S,4S)-4-(4-amino-5-((3,5-dimethoxyphenyl)ethynyl)-7H-pyrrolo[2,3-d]pyrimidin-7-yl)-2-(1,3,4-oxadiazole-2-yl)pyrrolidin-1-yl)prop-2-en-1-one (Example Compound 68)

(Step 1) Synthesis of (2S,4S)-4-(4-amino-5-(3,5-dimethoxyphenyl)ethynyl)-7H-pyrrolo[2,3-d]pyrimidin-7-yl)-1-(tert-butoxycarbonyl)pyrrolidine-2-carboxylic acid The (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate (393.8 mg) obtained in Example 66 (Step 6) was dissolved in methanol (6 ml). After cooling to 0° C., 4N aqueous sodium hydroxide (3 ml) was added thereto. The reaction suspension was stirred at room temperature for 3 hours. 5N hydrochloric acid was added to the reaction mixture to a pH of 5, and ethyl acetate and water were added to separate the organic layer. The organic layer was dried over anhydrous magnesium sulfate, and the solvent was distilled off under reduced pressure to obtain the title compound as a light-yellow solid (280 mg). Physical properties: m/z[M+H]+ 508.3

(Step 2) Synthesis of (2S,4S)-tert-butyl 4-(4-amino-5-((3,5-dimethoxyphenyl)ethynyl)-7H-pyrrolo[2,3-d]pyrimidin-7-yl)-2-(hydrazine carbonyl)pyrrolidine-1-carboxylate DIPEA (73 μl) and hydrazine monohydrate (46 μl) were added to a solution of (2S,4S)-4-(4-amino-5-((3,5-dimethoxyphenyl)ethynyl)-7H-pyrrolo[2,3-d]pyrimidin-7-yl)-1-(tert-butoxycarbonyl)pyrrolidine-2-carboxylic acid (106 mg) obtained in Step 1 above and TBTU (100 mg) in DMF (2 ml), and the resulting mixture was stirred at room temperature for 10 minutes. Ethyl acetate and water were added to the reaction mixture to separate the organic layer, and the organic layer was dried over anhydrous magnesium sulfate. The solvent was distilled off under reduced pressure (Step 3) Synthesis of (2S,4S)-tert-butyl 4-(4-amino-5-((3,5-dimethoxyphenyl)ethynyl)-7H-pyrrolo[2,3-d]pyrimidin-7-yl)-2-(1,3,4-oxadiazole-2-yl)pyrrolidine-1-carboxylate Toluene (3 ml) and trimethyl orthoformate (79 μl) were added to the (2S,4S)-tert-butyl 4-(4-amino-5-((3,5-dimethoxyphenyl)ethynyl)-7H-pyrrolo[2,3-d]pyrimidin-7-yl)-2-(hydrazine carbonyl)pyrrolidine-1-carboxylate (93.6 mg) obtained in Step 2, and the resulting mixture was stirred at 110° C. overnight. Acetic acid (400 μl) was added to the reaction mixture, and stirred at 110° C. for 6 hours. Ethyl acetate and water were added to the reaction mixture to separate the organic layer. The organic layer was dried over anhydrous magnesium sulfate, and the solvent was distilled off under reduced pressure. The resulting residue was purified by silica gel column chromatography (developing solvent: chloroform/methanol) to obtain the title compound as a light-yellow, amorphous substance (50 mg). Physical properties: m/z [M+H]$^+$ 532.2

(Step 4) Synthesis of 7-((3S,5S)-5-(1,3,4-oxadiazole-2-yl)pyrrolidin-3-yl)-5-((3,5-dimethoxyphenyl)ethynyl)-7H-pyrrolo[2,3-d]pyrimidin-4-amine In accordance with Example 66 (Step 7), except that the (2S,4S)-tert-butyl 4-(4-amino-5-((3,5-dimethoxyphenyl)ethynyl)-7H-pyrrolo[2,3-d]pyrimidin-7-yl)-2-(1,3,4-oxadiazole-2-yl)pyrrolidine-1-carboxylate (50 mg) obtained in Step 3 was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance (30.3 mg). m/z[M+H]$^+$ 432.0

(Step 5) Synthesis of Example Compound 68

In accordance with Example 66 (Step 8), except that 7-((3S,5S)-5-(1,3,4-oxadiazole-2-yl)pyrrolidin-3-yl)-5-((3,5-dimethoxyphenyl)ethynyl)-7H-pyrrolo[2,3-d]pyrimidin-4-amine obtained in Step 4 was used in place of (2S,4S)-methyl 4-(4-amino-5-((3,5-dimethoxyphenyl)ethynyl)-7H-pyrrolo[2,3-d]pyrimidin-7-yl)pyrrolidine-2-carboxylate, the title compound was obtained as a light-yellow, amorphous substance. Table 18 shows the physical properties thereof.

Example 69

Synthesis of 1-((2S,4S)-4-(4-amino-5-((3,5-dimethoxyphenyl)ethynyl)-7H-pyrrolo[2,3-d]pyrimidin-7-yl)-2-(5-methyl-1,3,4-oxadiazole-2-yl)pyrrolidin-1-yl)prop-2-en-1-one (Example Compound 69)

(Step 1) Synthesis of (2S,4S)-tert-butyl 4-(4-amino-5-((3,5-dimethoxyphenyl)ethynyl)-7H-pyrrolo[2,3-d]pyrimidin-7-yl)-2-(5-methyl-1,3,4-oxadiazole-2-yl)pyrrolidine-1-carboxylate In accordance with Example 68 (Step 3), except that triethyl orthoacetate was used in place of trimethyl orthoformate, the title compound was obtained as a light-yellow, amorphous substance. Physical properties: m/z[M+H]$^+$ 546.5

(Step 2) Synthesis of 5-((3,5-dimethoxyphenyl)ethynyl)-7-((3S,5S)-5-(5-methyl-1,3,4-oxadiazole-2-yl)pyrrolidin-3-yl)-7H-pyrrolo[2,3-d]pyrimidin-4-amine In accordance with Example 66 (Step 7), except that the (2S,4S)-tert-butyl 4-(4-amino-5-((3,5-dimethoxyphenyl)ethynyl)-7H-pyrrolo[2,3-d]pyrimidin-7-yl)-2-(5-methyl-1,3,4-oxadiazole-2-yl)pyrrolidine-1-carboxylate obtained in Step 1 was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance. Physical properties: m/z[M+H]$^+$ 466.0

(Step 3) Synthesis of Example Compound 69

In accordance with Example 66 (Step 8), except that the 5-((3,5-dimethoxyphenyl)ethynyl)-7-((3S,5S)-5-(5-methyl-1,3,4-oxadiazole-2-yl)pyrrolidin-3-yl)-7H-pyrrolo[2,3-d]pyrimidin-4-amine obtained in Step 2 was used in place of (2S,4S)-methyl 4-(4-amino-5-((3,5-dimethoxyphenyl)ethynyl)-7H-pyrrolo[2,3-d]pyrimidin-7-yl)pyrrolidine-2-carboxylate, the title compound was obtained as a light-yellow, amorphous substance. Table 18 shows the physical properties thereof.

Example 70

Synthesis of 1-((2S,4S)-4-(4-amino-5-((3,5-dimethoxyphenyl)ethynyl)-7H-pyrrolo[2,3-d]pyrimidin-7-yl)-2-(5-((dimethylamino)methyl)-1,3,4-oxadiazole-2-yl)pyrrolidin-1-yl)prop-2-en-1-one (Example Compound 70)

(Step 1) Synthesis of (2S,4S)-tert-butyl 4-(4-amino-5-((3,5-dimethoxyphenyl)ethynyl)-7H-pyrrolo[2,3-d]pyrimidin-7-yl)-2-(2-(2-(dimethylamino)acetyl)hydrazine carbonyl)pyrrolidine-1-carboxylate In accordance with Example 68 (Step 2), except that 2-(dimethylamino)acetohydrazide was used in place of hydrazine monohydrate, the title compound was obtained as a light-yellow, amorphous substance. Physical properties: m/z[M+H]$^+$ 607.3

(Step 2) Synthesis of (2S,4S)-tert-butyl 4-(4-amino-5-((3,5-dimethoxyphenyl)ethynyl)-7H-pyrrolo[2,3-d]pyrimidin-7-yl)-2-(5-((dimethylamino)methyl)-1,3,4-oxadiazole-2-yl)pyrrolidine-1-carboxylate DIPEA (105 μl) and tosyl chloride (56 mg) were added to a solution of (2S,4S)-tert-butyl 4-(4-amino-5-((3,5-dimethoxyphenyl)ethynyl)-7H-pyrrolo[2,3-d]pyrimidin-7-yl)-2-(2-(2-(dimethylamino)acetyl)hydrazine carbonyl)pyrrolidine-1-carboxylate (100 mg) obtained in Step 1 in acetonitrile (3 ml), and the mixture was stirred at 40° C. for 1 hour. Ethyl acetate and water were added to the reaction mixture to separate the organic layer. The organic layer was dried over anhydrous magnesium sulfate, and the solvent was distilled off under reduced pressure. The resulting residue was purified by silica gel column chromatography (developing solvent: chloroform/methanol) to obtain the title compound as a light-yellow, amorphous substance (40.5 mg). Physical properties: m/z[M+H]$^+$ 589.2

Synthesis of (Step 3) 5-((3,5-dimethoxyphenyl)
ethynyl)-7-((3S,5S)-5-(5-((dimethylamino)methyl)-
1,3,4-oxadiazol-2-yl)pyrrolidin-3-yl)-7H-pyrrolo[2,
3-d]pyrimidin-4-amine In accordance with Example 66 (Step 7), except that the (2S,4S)-tert-butyl 4-(4-amino-5-((3,5-dimethoxyphenyl) ethynyl)-7H-pyrrolo[2,3-d]pyrimidin-7-yl)-2-(5-((dimethylamino)methyl)-1,3,4-oxadiazol-2-yl)pyrrolidine-1-carboxylate obtained in Step (2) was used in place of (2S,4S)-1-tert-butyl 2-methyl 4-(4-amino-5-((3,5-dimethoxyphenyl) ethynyl)-7H-pyrrolo[2,3-d]pyrimidin-7-yl)pyrrolidine-1,2-dicarboxylate, the title compound was obtained as a light-yellow, amorphous substance. Physical properties: m/z[M+H]$^+$ 489.2

(Step 4) Synthesis of Example Compound 70

In accordance with Example 66 (Step 8), except that the 5-((3,5-dimethoxyphenyl)ethynyl)-7-((3S,5S)-5-(5-((dimethylamino)methyl)-1,3,4-oxadiazol-2-yl)pyrrolidin-3-yl)-7H-pyrrolo[2,3-d]pyrimidin-4-amine obtained in Step 3 was used in place of (2S,4S)-methyl 4-(4-amino-5-((3,5-dimethoxyphenyl)ethynyl)-7H-pyrrolo[2,3-d]pyrimidin-7-yl) pyrrolidine-2-carboxylate, the title compound was obtained as a light-yellow, amorphous substance. Table 18 shows the physical properties thereof.

Example 71

Synthesis of (2S,4S)-1-acryloyl-4-(4-amino-5-((3,5-dimethoxyphenyl)ethynyl)-7H-pyrrolo[2,3-d]pyrimidin-7-yl)-N-(2-(dimethylamino)ethyl)-N-methylpyrrolidine-2-carboxamide (Example Compound 71)

(Step 1) Synthesis of (2S,4S)-tert-butyl 4-(4-amino-
5-((3,5-dimethoxyphenyl)ethynyl)-7H-pyrrolo[2,3-d]
pyrimidin-7-yl)-2-((2-(dimethylamino)ethyl)
(methyl)carbamoyl)pyrrolidine-1-carboxylate A solution of (2S,4S)-4-(4-amino-5-((3,5-dimethoxyphenyl)ethynyl)-7H-pyrrolo[2,3-d]pyrimidin-7-yl)-1-(tert-butoxycarbonyl)pyrrolidine-2-carboxylic acid (25.4 mg) obtained in Example 68 (Step 1), TBTU (17.7 mg), N,N,N'-trimethylethane-1,2-diamine (13 μl), and DIPEA (26 μl) in acetonitrile (3 ml) was stirred at room temperature for 1 hour. Ethyl acetate and water were added to separate the organic layer. The organic layer was dried over anhydrous sodium sulfate, and the solvent was distilled off under reduced pressure. The resulting residue was purified by basic silica gel column chromatography (developing solvent: chloroform/methanol) to obtain the title compound as a light-yellow, amorphous substance (3 mg). Physical properties: m/z[M+H]$^+$ 592.4

(Step 2) Synthesis of (2S,4S)-4-(4-amino-5-((3,5-
dimethoxyphenyl)ethynyl)-7H-pyrrolo[2,3-d]pyrimi-
din-7-yl)-N-(2-(dimethylamino)ethyl)-N-methylpyr-
rolidine-2-carboxamide In accordance with Example 66 (Step 7), except that the (2S,4S)-tert-butyl 4-(4-amino-5-((3,5-dimethoxyphenyl) ethynyl)-7H-pyrrolo[2,3-d]pyrimidin-7-yl)-2-((2-(dimethylamino)ethyl)(methyl)carbamoyl)pyrrolidine-1-carboxylate obtained in Step 1 above was used in place of (2S,4S)-1-tert-butyl 2-methyl 4-(4-amino-5-((3,5-dimethoxyphenyl) ethynyl)-7H-pyrrolo[2,3-d]pyrimidin-7-yl)pyrrolidine-1,2-dicarboxylate, the title compound was obtained as a colorless, amorphous substance. Physical properties: m/z [M+H]$^+$ 492.4

(Step 3) Synthesis of Example Compound 71

In accordance with Example 66 (Step 8), except that the (2S,4S)-4-(4-amino-5-((3,5-dimethoxyphenyl)ethynyl)-7H-pyrrolo[2,3-d]pyrimidin-7-yl)-N-(2-(dimethylamino)ethyl)-N-methylpyrrolidine-2-carboxamide obtained in Step 2 was used in place of (2S,4S)-methyl 4-(4-amino-5-((3,5-dimethoxyphenyl)ethynyl)-7H-pyrrolo[2,3-d]pyrimidin-7-yl) pyrrolidine-2-carboxylate, the title compound was obtained as a colorless, amorphous substance. Table 19 shows the physical properties thereof.

Example 72

Synthesis of 1-(4-((4-amino-5-((3,5-dimethoxyphe-
nyl)ethynyl)-7H-pyrrolo[2,3-d]pyrimidin-7-yl)
methyl)piperidin-1-yl)-4-(dimethylamino)but-2-en-
1-one (Example Compound 72)

In accordance with Example 38, except that N-Boc-4-hydroxymethylpiperidin was used in place of (R)—N-Boc-3-pyrrolidinol, the title compound was obtained as a light-yellow, amorphous substance. Table 19 shows the physical properties thereof.

Example 73

Synthesis of (S)-1-(3-(4-amino-3-((3,5-dimethoxy-
phenyl)ethynyl)-1H-pyrrolo[3,2-c] pyridin-1-yl)
pyrrolidin-1-yl)prop-2-en-1-one (Example Com-
pound 73)

(Step 1) Synthesis of 4-chloro-3-iodo-1H-pyrrolo[3,
2-c]pyridine

4-Chloro-1H-pyrrolo[3,2-c]pyridine (247 mg) synthesized by the method disclosed in WO2007/095223 was dissolved in DMF (7.0 ml). After cooling to 0° C., N-iodosuccinimide (382 mg) was added thereto. The resulting mixture was stirred at room temperature for 1 hour, and then chloroform and water were added thereto to separate the organic layer. After the organic layer was dried over anhydrous magnesium sulfate, the solvent was distilled off under reduced pressure. The resulting residue was purified by silica gel column chromatography (developing solvent: hexane/ethyl acetate) to obtain the title compound as a dark-brown solid (455 mg). Physical properties: m/z[M+H]$^+$ 279.1

(Step 2) Synthesis of (S)-tert-butyl 3-(4-chloro-3-
iodo-1H-pyrrolo[3,2-c]pyridin-1-yl)pyrrolidine-1-
carboxylate The 4-chloro-3-iodo-1H-pyrrolo[3,2-c]pyridine (225 mg) obtained in Step 1 was dissolved in DMF (3.0 ml). After cooling to 0° C., 60% sodium hydride (64.5 mg) was added thereto. The (R)-tert-butyl 3-(methylsulfonyloxy)pyrrolidine-1-carboxylate (322 mg) obtained in Example 2 (Step 1) was added to the reaction mixture using DMF (2.0 ml), and the mixture was stirred overnight. 60% Sodium hydride (64.5 mg) was additionally added, and the mixture was stirred at 85° C. overnight. Ethyl acetate and water were added to the reaction mixture to separate the organic layer.

The organic layer was dried over anhydrous magnesium sulfate, and the solvent was distilled off under reduced pressure. The resulting residue was purified by silica gel column chromatography (developing solvent: hexane/ethyl acetate) to obtain the title compound as a crude product (192 mg). Physical properties: m/z[M+H]$^+$ 448.3

(Step 3) Synthesis of (S)-tert-butyl 3-(4-chloro-3-((3,5-dimethoxyphenyl)ethynyl)-1H-pyrrolo[3,2-c]pyridin-1-yl)pyrrolidine-1-carboxylate PdCl$_2$(dppf)CH$_2$Cl$_2$ (33 mg) was added to a mixture of the crude product of (S)-tert-butyl 3-(4-chloro-3-iodo-1H-pyrrolo[3,2-c]pyridin-1-yl)pyrrolidine-1-carboxylate (180 mg) obtained in Step 2, 1-ethynyl 3,5-dimethoxybenzene (97 mg), copper (I) iodide (15 mg), and triethylamine (1.0 ml) in THF (4.0 ml). After nitrogen purging, the resulting mixture was stirred at 50° C. for 30 minutes. Ethyl acetate and water were added to the reaction mixture to separate the organic layer. After being washed with a saturated sodium chloride solution, the organic layer was dried over anhydrous sodium sulfate, and the solvent was then distilled off under reduced pressure. The resulting residue was purified by silica gel column chromatography (developing solvent: hexane/ethyl acetate) to obtain the title compound as a colorless, amorphous substance (133 mg). Physical properties: m/z [M+H]$^+$482.4

(Step 4) Synthesis of (S)-tert-butyl 3-(4-amino-3-((3,5-dimethoxyphenyl)ethynyl)-1H-pyrrolo[3,2-c]pyridin-1-yl)pyrrolidine-1-carboxylate Under a nitrogen atmosphere, the (S)-tert-butyl 3-(4-chloro-3-((3,5-dimethoxyphenyl)ethynyl)-1H-pyrrolo[3,2-c]pyridin-1-yl)pyrrolidine-1-carboxylate (120 mg) obtained in Step 3, 2,2'-bis(diphenylphosphino)-1,1'-binaphthalene (BINAP) (26 mg), sodium tert-butoxide (72 mg), benzophenone imine (92 mg), and tris (dibenzylideneacetone)dipalladium (36 mg) were suspended in toluene (10 ml), and the result was stirred at 115° C. for 90 minutes. After dilution with ethyl acetate, celite filtration was performed. The solvent was distilled off under reduced pressure. Hydroxyaminehydrochloride (366 mg), sodium bicarbonate (442 mg), methanol (16 ml), and water (4 ml) were added to the resulting residue, and the resulting mixture was stirred at room temperature for 2 hours. The solvent was distilled off under reduced pressure. Thereafter, ethyl acetate and a saturated sodium chloride solution were added to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a colorless, amorphous substance (35 mg). Physical properties: m/z[M+H]$^+$ 463.4

(Step 5) Synthesis of Example Compound 73

In accordance with Example 1 (Step 4), except that the (S)-tert-butyl 3-(4-amino-3-((3,5-dimethoxyphenyl)ethynyl)-1H-pyrrolo[3,2-c]pyridin-1-yl)pyrrolidine-1-carboxylate obtained in Step (3) was used in place of tert-butyl 3-(4-amino-3-((3,5-dimethoxyphenyl)ethynyl)-1H-pyrazolo[3,4-d]pyrimidin-1-yl)pyrrolidine-1-carboxylate, the title compound was obtained as a white solid. Table 19 shows the physical properties thereof.

Reference Example 1

Synthesis of (R)-1-(3-(4-amino-3-(4-phenoxyphenyl)-1H-pyrazolo[3,4-d]pyrimidin-1-yl)piperidin-1-yl)prop-2-en-1-one (Reference Example Compound 1)

The compound was synthesized according to the method disclosed in WO2008/121742. Table 20 shows the physical properties thereof.

Reference Example 2

Synthesis of 3-cyclobutyl-1-(phenylethynyl)imidazo[1,5-a]pyrazin-8-amine (Reference Example Compound 2)

The compound was synthesized according to the method disclosed in WO2007/087395. Table 20 shows the physical properties thereof.

Reference Example 3

Synthesis of (S)-1-(3-(4-amino-3-((3,5-dimethoxyphenyl)ethynyl)-1H-pyrazolo[3,4-d]pyrimidin-1-yl)pyrrolidin-1-yl)propan-1-one (Reference Example Compound 3)

In accordance with Example 1, (S)-3-((3,5-dimethoxyphenyl)ethynyl)-1-(pyrrolidin-3-yl)-1H-pyrazolo[3,4-d]pyrimidin-4-amine and propionyl chloride were used to obtain the title compound as a white solid. Table 20 shows the physical properties thereof.

Reference Example 4

Synthesis of (S)-1-(3-(4-amino-3-((3,5-diisopropylphenyl)ethynyl)-1H-pyrazolo[3,4-d]pyrimidin-1-yl)pyrrolidin-1-yl)-4-(dimethylamino)but-2-en-1-one (Reference Example Compound 4)

(Step 1) Synthesis of 1-ethynyl-3,5-diisopropylbenzene

PdCl$_2$(dppf)CH$_2$Cl$_2$ (163 mg) was added to a mixture of trimethylsilylacetylene (589 mg), 1-bromo-3,5-diisopropylbenzene (480 mg), copper (I) iodide (76 mg), and triethylamine (0.11 ml) in THF (4 ml). After nitrogen purging, the resulting mixture was stirred at 80° C. for 4 hours. Ethyl acetate and water were added to the reaction mixture to separate the organic layer. After drying the result over anhydrous sodium sulfate, the solvent was distilled off under reduced pressure. A 2% potassium hydroxide methanol solution (10 ml) was added to the resulting residue, and the result was stirred at room temperature overnight. Chloroform and water were added to the reaction mixture to separate the organic layer. After drying the result over anhydrous sodium sulfate, the solvent was distilled off under reduced pressure. The resulting residue was purified by silica gel column chromatography (developing solvent: hexane) to obtain the title compound as a yellow, oily substance (181 mg).

(Step 2) Synthesis of (S)-tert-butyl 3-(4-amino-3-iodo-1H-pyrazolo[3,4-d]pyrimidin-1-yl)pyrrolidine-1-carboxylate A suspension of 3-iodo-1H-pyrazolo[3,4-d]pyrimidin-4-amine (446 mg), (R)-tert-butyl 3-(methylsulfonyloxy)pyrrolidine-1-carboxylate (450 mg), potassium carbonate (692 mg) in DMF (5.0 ml) was stirred at 85° C. for 6 hours. Ethyl acetate and water were added thereto to separate the organic layer. The organic layer was dried over anhydrous sodium sulfate, and the solvent was distilled off under reduced pressure. The resulting residue was purified by basic silica gel column chromatography (developing solvent: hexane/ethyl acetate) to obtain the title compound as a light-yellow, amorphous substance (354 mg). Physical properties: m/z [M+H]$^+$ 431.1

(Step 3) Synthesis of (S)-tert-butyl 3-(4-amino-3-((3,5-diisopropylphenyl)ethynyl)-1H-pyrazolo[3,4-d]pyrimidin-1-yl)pyrrolidine-1-carboxylate PdCl$_2$(dppf)CH$_2$Cl$_2$ (8.2 mg) was added to a mixture of 1-ethynyl-3,5-diisopropylbenzene (56 mg) obtained in Step 1, (S)-tert-butyl 3-(4-amino-3-iodo-1H-pyrazolo[3,4-d]pyrimidin-1-yl)pyrrolidine-1-carboxylate (43 mg) obtained in Step 2, copper (I) iodide (3.8 mg), and triethylamine (0.2 ml) in THF (2.0 ml). After nitrogen purging, the resulting mixture was stirred at 80° C. for 1.5 hours. Ethyl acetate and water were added to the reaction mixture to separate the organic layer. The organic layer was washed with a saturated sodium chloride solution. After drying the result over anhydrous sodium sulfate, the solvent was distilled off under reduced pressure. The resulting residue was purified by basic silica gel column chromatography (developing solvent: hexane/ethyl acetate) to obtain the title compound as a colorless, amorphous substance (42 mg). Physical properties: m/z[M+H]$^+$ 489.2

(Step 4) Synthesis of (S)-3-((3,5-diisopropylphenyl)ethynyl)-1-(pyrrolidin-3-yl)-1H-pyrazolo[3,4-d]pyrimidin-4-amine In accordance with Example 66 (Step 7), except that the (S)-tert-butyl 3-(4-amino-3-((3,5-diisopropylphenyl)ethynyl)-1H-pyrazolo[3,4-d]pyrimidin-1-yl)pyrrolidine-1-carboxylate obtained in Step (3) was used in place of (2S,4S)-1-tert-butyl 2-methyl 4-(4-amino-5-((3,5-dimethoxyphenyl)ethynyl)-7H-pyrrolo[2,3-d]pyrimidin-7-yl)pyrrolidine-1,2-dicarboxylate, the title compound was obtained as a light-yellow, amorphous substance.

(Step 5) Synthesis of Reference Example Compound 4

In accordance with Example 4, except that the (S)-3-((3,5-diisopropylphenyl)ethynyl)-1-(pyrrolidin-3-yl)-1H-pyrazolo[3,4-d]pyrimidin-4-amine obtained in Step (4) was used in place of (S)-3-((3,5-dimethoxyphenyl)ethynyl)-1-(pyrrolidin-3-yl)-1H-pyrazolo[3,4-d]pyrimidin-4-amine, the title compound was obtained as a light-yellow, amorphous substance. Table 20 shows the physical properties thereof.

Reference Example 5

Synthesis of (S)-1-(3-(4-amino-3-((3-methoxyphenyl)ethynyl)-1H-pyrazolo[3,4-d]pyrimidin-1-yl)pyrrolidin-1-yl)-4-(dimethylamino)but-2-en-1-one (Reference Example Compound 5)

(Step 1) Synthesis of (S)-1-(3-(4-amino-3-iodo-1H-pyrazolo[3,4-d]pyrimidin-1-yl)pyrrolidin-1-yl)-4-(dimethylamino)but-2-en-1-one 4N-Hydrochloric acid/1,4-dioxane (4 ml) was added to the (S)-tert-butyl 3-(4-amino-3-iodo-1H-pyrazolo[3,4-d]pyrimidin-1-yl)pyrrolidine-1-carboxylate (488 mg) obtained in Reference Example 4 (Step 2), and the resulting mixture was stirred for 1 hour. The solvent was distilled off under reduced pressure. A solution of 4-(dimethylamino)but-2-enoic-acid hydrochloride (281 mg) and HATU (647 mg) in DMF (5.0 ml) was added to the resulting residue. Further, DIPEA (0.78 ml) was added thereto, and the mixture was stirred overnight. The reaction mixture was concentrated under reduced pressure, and chloroform (50 ml) and ethanol (50 ml) were added to the resulting residue. The insoluble matter was removed by filtration, and the filtrate was concentrated under reduced pressure. The resulting residue was washed with ethyl acetate (5.0 ml) and dried to obtain the crude product of the title compound (458 mg). Physical properties: m/z[M+H]$^+$ 442.0

(Step 2) Synthesis of Reference Example Compound 5

PdCl$_2$(dppf)CH$_2$Cl$_2$ (1.3 mg) was added to a mixture of (S)-1-(3-(4-amino-3-iodo-1H-pyrazolo[3,4-d]pyrimidin-1-yl)pyrrolidin-1-yl)-4-(dimethylamino)but-2-en-1-one (8.0 mg) obtained in Step 1, 1-ethynyl-3-methoxybenzene (4.0 mg), copper (I) iodide (0.6 mg), and triethylamine (8.6 µl) in THF (1.0 ml). After nitrogen purging, the resulting mixture was stirred at 80° C. overnight. The reaction mixture was diluted with ethyl acetate and methanol. The resulting diluted solution was treated with basic silica gel, and then concentrated. The resulting residue was purified by reversed-phase HPLC purification (water/acetonitrile (0.1% formic acid)) to obtain the title compound as a colorless, amorphous substance (1.4 mg). Table 20 shows the physical properties thereof.

Reference Example 6

Synthesis of (S)—N-(3-((4-amino-1-(1-(4-(dimethylamino)but-2-enoyl)pyrrolidin-3-yl)-1H-pyrazolo[3,4-d]pyrimidin-3-yl)ethynyl)phenyl)acetamide (Reference Example Compound 6)

In accordance with Reference Example 5, except that N-(3-ethynylphenyl)acetamide was used in place of 1-ethynyl-3-methoxybenzene, the title compound was obtained as a colorless, amorphous substance. Table 20 shows the physical properties thereof.

Reference Example 7

Synthesis of (S)-1-(3-(4-amino-3-(pyridin-3-ylethynyl)-1H-pyrazolo[3,4-d]pyrimidin-1-yl)pyrrolidin-1-yl)-4-(dimethylamino)but-2-en-1-one (Reference Example Compound 7)

In accordance with Reference Example 5, 3-ethynyl pyridine was used in place of 1-ethynyl-3-methoxybenzene, the title compound was obtained as a colorless, amorphous substance. Table 20 shows the physical properties thereof.

TABLE 1
| Ex Comp | Structural formula | Physical properties |
|---|---|---|
| 1 | 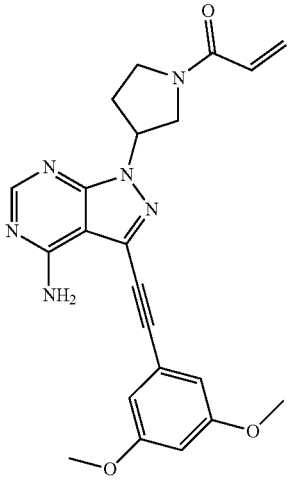 [SMILES: C=CC(=O)N1CCC(n2nc(C#Cc3cc(OC)cc(OC)c3)c3c(N)ncnc32)C1] | 1H-NMR (DMS0-d 6) δ: 2.29-2.50 (2H, m), 3.55-4.10 (4H, m), 3.77 (6H, s), 5.40-5.55 (1H, m), 5.62-5.72 (1H, m), 6.10-6.20 (1H, m), 6.50-6.70 (1H, m), 6.64 (1H, d, J = 2.3 Hz), 6.90 (2H, d, J = 2.3 Hz), 8.26 (1H, s).<br>m/z [M + H]$^+$ 419.0 |
| 2 | 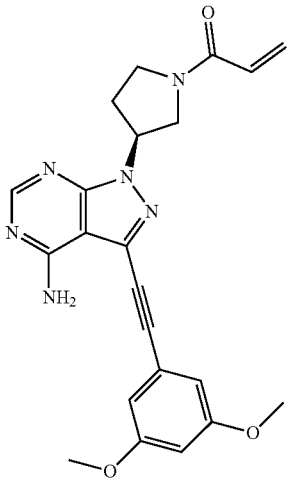 [SMILES: C=CC(=O)N1CC[C@H](n2nc(C#Cc3cc(OC)cc(OC)c3)c3c(N)ncnc32)C1] | 1H-NMR (DMS0-d6) δ: 2.29-2.50 (2H, m), 3.55-4.10 (4H, m), 3.77 (6H, s), 5.40-5.55 (1H, m), 5.62-5.72 (1H, m), 6.10-6.20 (1H, m), 6.50-6.70 (1H, m), 6.64 (1H, d, J = 2.3 Hz), 6.90 (2H, d, J = 2.3 Hz), 8.26 (1H, s).<br>m/z [M + H]$^+$ 419.0 |
| 3 | 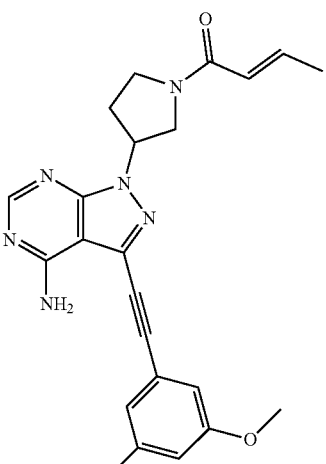 | 1H-NMR (DMS0-d6) δ: 1.81 (1.5H, dd, J = 6.8, 1.6 Hz), 1.85 (1.5H, dd, J = 6.8, 1.6 Hz), 2.29-2.50 (2H, m), 3.56-3.92 (3.5H, m), 3.77 (6H, s), 4.02-4.10 (0.5H, m), 5.42-5.53 (1H, m), 6.26 (0.5H, dd, J = 15.1, 1.6 Hz), 6.34 (0.5H, dd, J = 15.1, 1.6 Hz), 6.60 (1H, t, J = 2.4 Hz), 6.64-6.74 (1H, m), 6.91 (2H, d, J = 2.4 Hz), 8.26 (0.5H, S), 8.27 (0.5H, S).<br>m/z [M + H]$^+$ 433.1 |

TABLE 1-continued

| Ex Comp | Structural formula | Physical properties |
|---|---|---|
| 4 | (structure) | 1H-NMR (DMSO-d6) δ: 2.06 (3H, s), 2.09 (3H, s), 2.20-2.45 (2H, m), 2.95 (1H, d, J = 5.9 Hz), 2.99 (1H, d, J = 5.9 Hz), 3.30-4.10 (4H, m), 5.30-5.50 (1H, m), 6.29 (0.5H, d, J = 15.0 Hz), 6.38 (0.5H, d, J = 15.0 Hz) 6.53-6.65 (3H, m), 6.84 (2H, s), 8.12 (1H, s). m/z [M + H]$^+$ 476.1 |

TABLE 2

| | | |
|---|---|---|
| 5 | (structure) | m/z [M + H]$^+$ 417.0 |
| 6 | (structure) | 1H-NMR (CDCl3) δ: 2.37-2.68 (2H, m), 3.74-3.82 (2H, m), 3.82 (6H, s), 4.07-4.21 (2H, m), 5.11-5.19 (1H, m), 5.50-5.56 (1H, m), 5.58 (1H, t, J = 46.8, 2.0 Hz), 5.85 (2H, s), 6.54 (1H, t, J = 2.0 Hz), 6.74 (2H, d, J = 2.4 Hz), 8.37 (1H, s) m/z [M + H]$^+$ 437.2 |

TABLE 2-continued
| 7 | 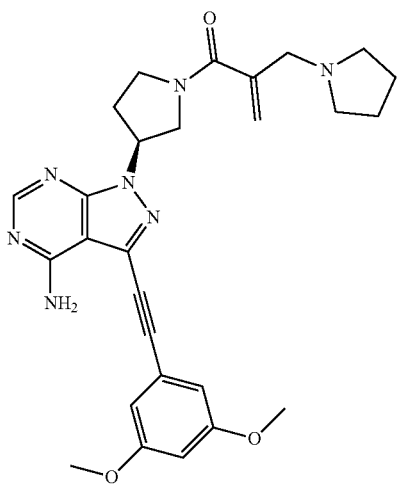 [SMILES: C=C(CN1CCCC1)C(=O)N1CC[C@H](n2nc(C#Cc3cc(OC)cc(OC)c3)c3c(N)ncnc32)C1] | 1H-NMR (CDCl3) δ: 1.70-1.80 (4H, m), 2.42-2.66 (6H, m), 3.20-3.32 (1H, m), 3.40-3.46 (1H, m), 3.76-3.82 (2H, m), 3.82 (6H, s), 3.91-4.15 (3H, m), 5.32-5.56 (3H, m), 5.91 (2H, s), 6.54 (1H, t, J = 2.0 Hz) 6.73 (2H, d, J = 2.4 Hz), 8.36 (1H, s) m/z [M + H]$^+$ 502.2 |
| --- | --- | --- |
| 8 | 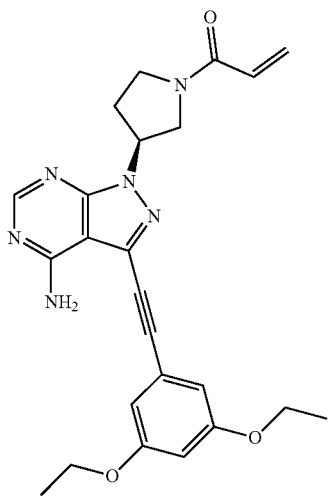 [SMILES: C=CC(=O)N1CC[C@H](n2nc(C#Cc3cc(OCC)cc(OCC)c3)c3c(N)ncnc32)C1] | 1H-NMR (CDCl3) δ: 1.42 (6H, t, J = 6.8 Hz), 2.39-2.72 (2H, m), 3.71-3.84 (1H, m), 3.96-4.12 (3H, m), 4.03 (4H, q, J = 6.8 Hz), 5.48-5.76 (2H, m), 5.84 (2H, br s), 6.38-6.56 (3H, m), 6.70-6.73 (2H, m), 8.36-8.38 (1H, m). m/z [M + H]$^+$ 447.2 |
| 9 | 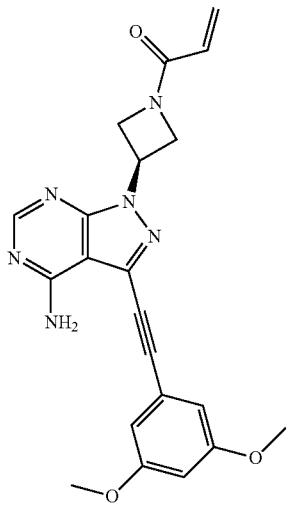 | 1H-NMR (DMS0-d6) δ: 3.78 (6H, s), 4.20-4.35 (1H, m), 4.40-4.50 (1H, m), 4.55-4.65 (1H, m), 4.70-4.80 (1H, m), 5.70-5.80 (2H, m), 6.16 (1H, dd, J = 17.1, 2.1 Hz), 6.38 (1H, dd, J = 17.1, 10.2 Hz), 6.61 (1H, t, J = 2.4 Hz), 6.94 (2H, d, J = 2.4 Hz), 8.26 (1H, s). m/z [M + H]$^+$ 405.1 |

TABLE 3
| | | |
|---|---|---|
| 10 | 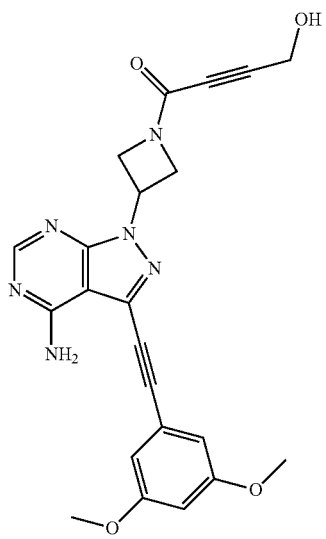 [SMILES: COc1cc(C#Cc2nn(C3CN(C(=O)C#CCO)C3)c3ncnc(N)c23)cc(OC)c1] | 1H-NMR (DMSO-d6) δ: 3.73 (6H, s), 4.12-4.28 (3H, m), 4.35-4.50 (2H, m), 4.55-4.65 (1H, m), 5.55 (1H, brs), 5.67 (1H, brs), 6.56 (1H, s), 6.87 (2H, s), 8.40 (1H, s).<br>m/z [M + H]$^+$ 433.3 |
| 11 | 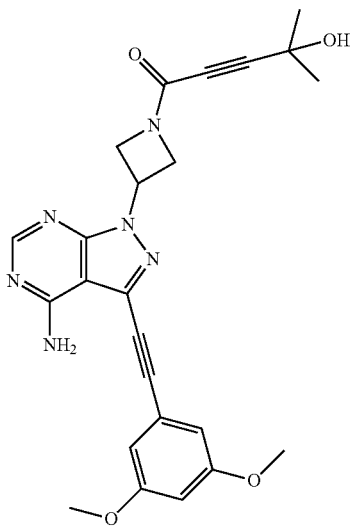 [SMILES: COc1cc(C#Cc2nn(C3CN(C(=O)C#CC(C)(C)O)C3)c3ncnc(N)c23)cc(OC)c1] | 1H-NMR (DMS0-d6) δ: 1.32 (6H, s), 3.70 (6H, s), 4.14-4.19 (1H, m), 4.33-4.44 (2H, m), 4.57 (1H, t, J = 9.3 Hz), 5.61-5.70 (2H, m), 6.53 (1H, s), 6.87 (2H, d, J = 2.2 Hz), 8.18 (1H, s).<br>m/z [M + H]$^+$ 461.4 |
| 12 | 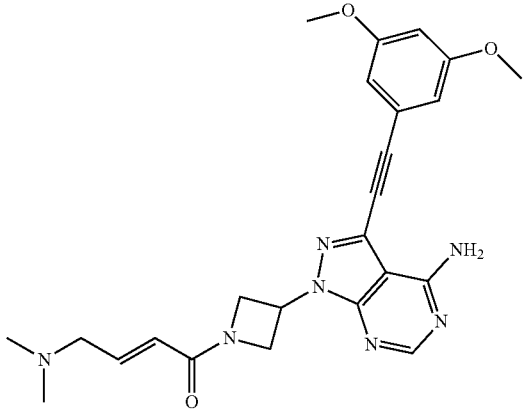 | 1H-NMR (DMS0-d6) δ: 2.08 (6H, s), 2.97 (2H, d, J = 6.2 Hz), 3.72 (6H, d, J = 3.7 Hz), 4.15-4.25 (1H, m), 4.30-4.48 (2H, m), 4.67 (1H, t, J = 9.0 Hz), 5.60-5.70 (1H, m), 6.11 (1H, d, J = 15.0 Hz), 6.55-6.61 (2H, m), 6.88 (2H, d, J = 1.8 Hz), 8.20 (1H, s).<br>m/z [M + H]$^+$ 462.1 |

TABLE 3-continued
| 13 | 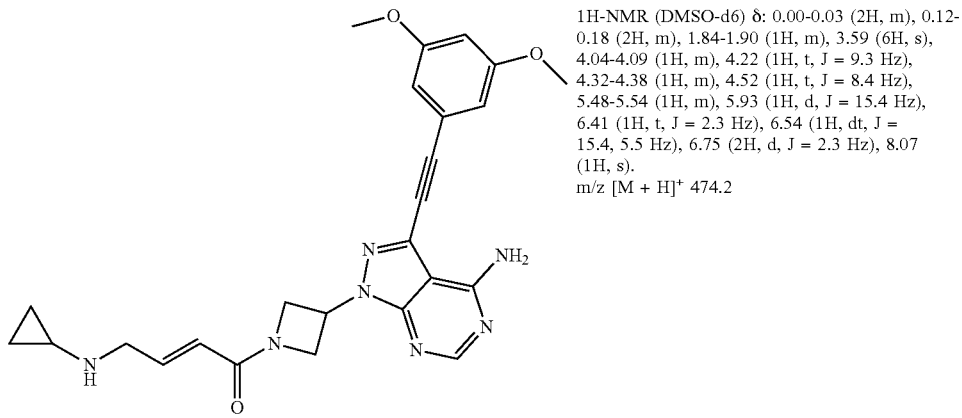 | 1H-NMR (DMSO-d6) δ: 0.00-0.03 (2H, m), 0.12-0.18 (2H, m), 1.84-1.90 (1H, m), 3.59 (6H, s), 4.04-4.09 (1H, m), 4.22 (1H, t, J = 9.3 Hz), 4.32-4.38 (1H, m), 4.52 (1H, t, J = 8.4 Hz), 5.48-5.54 (1H, m), 5.93 (1H, d, J = 15.4 Hz), 6.41 (1H, t, J = 2.3 Hz), 6.54 (1H, dt, J = 15.4, 5.5 Hz), 6.75 (2H, d, J = 2.3 Hz), 8.07 (1H, s).<br>m/z [M + H]⁺ 474.2 |
TABLE 4
| 14 | 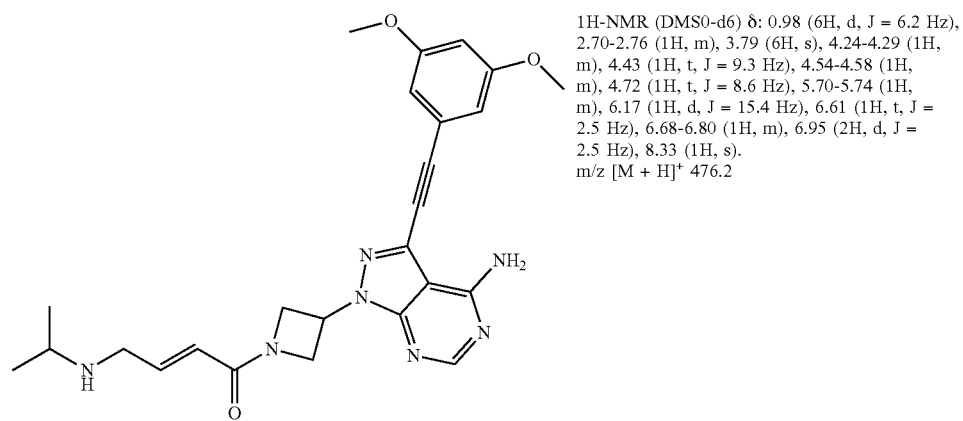 | 1H-NMR (DMS0-d6) δ: 0.98 (6H, d, J = 6.2 Hz), 2.70-2.76 (1H, m), 3.79 (6H, s), 4.24-4.29 (1H, m), 4.43 (1H, t, J = 9.3 Hz), 4.54-4.58 (1H, m), 4.72 (1H, t, J = 8.6 Hz), 5.70-5.74 (1H, m), 6.17 (1H, d, J = 15.4 Hz), 6.61 (1H, t, J = 2.5 Hz), 6.68-6.80 (1H, m), 6.95 (2H, d, J = 2.5 Hz), 8.33 (1H, s).<br>m/z [M + H]⁺ 476.2 |
| 15 | 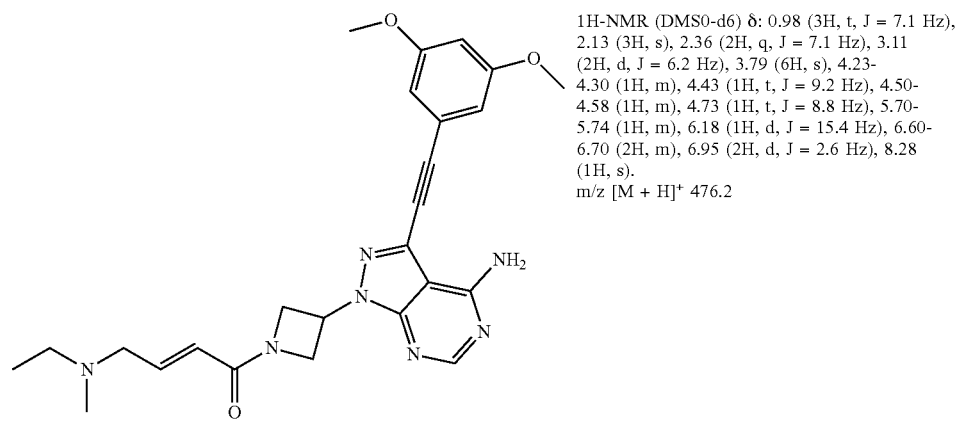 | 1H-NMR (DMS0-d6) δ: 0.98 (3H, t, J = 7.1 Hz), 2.13 (3H, s), 2.36 (2H, q, J = 7.1 Hz), 3.11 (2H, d, J = 6.2 Hz), 3.79 (6H, s), 4.23-4.30 (1H, m), 4.43 (1H, t, J = 9.2 Hz), 4.50-4.58 (1H, m), 4.73 (1H, t, J = 8.8 Hz), 5.70-5.74 (1H, m), 6.18 (1H, d, J = 15.4 Hz), 6.60-6.70 (2H, m), 6.95 (2H, d, J = 2.6 Hz), 8.28 (1H, s).<br>m/z [M + H]⁺ 476.2 |

TABLE 4-continued
| 16 | 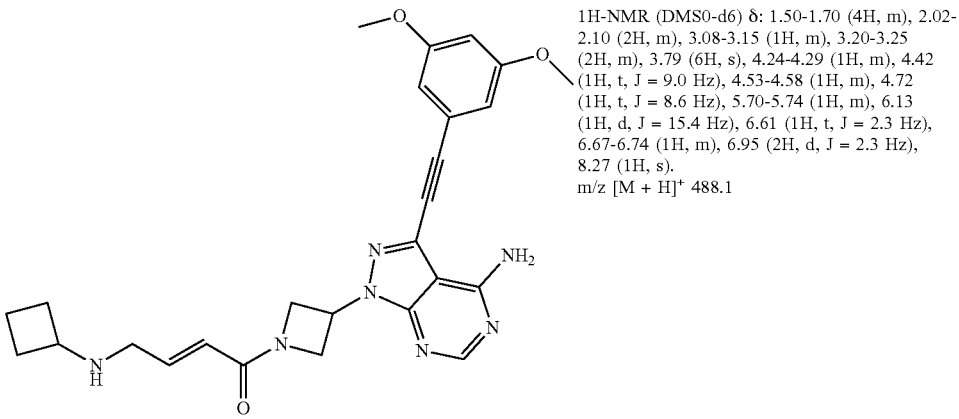 | 1H-NMR (DMS0-d6) δ: 1.50-1.70 (4H, m), 2.02-2.10 (2H, m), 3.08-3.15 (1H, m), 3.20-3.25 (2H, m), 3.79 (6H, s), 4.24-4.29 (1H, m), 4.42 (1H, t, J = 9.0 Hz), 4.53-4.58 (1H, m), 4.72 (1H, t, J = 8.6 Hz), 5.70-5.74 (1H, m), 6.13 (1H, d, J = 15.4 Hz), 6.61 (1H, t, J = 2.3 Hz), 6.67-6.74 (1H, m), 6.95 (2H, d, J = 2.3 Hz), 8.27 (1H, s).<br>m/z [M + H]$^+$ 488.1 |
|---|---|---|
TABLE 5
| 17 | 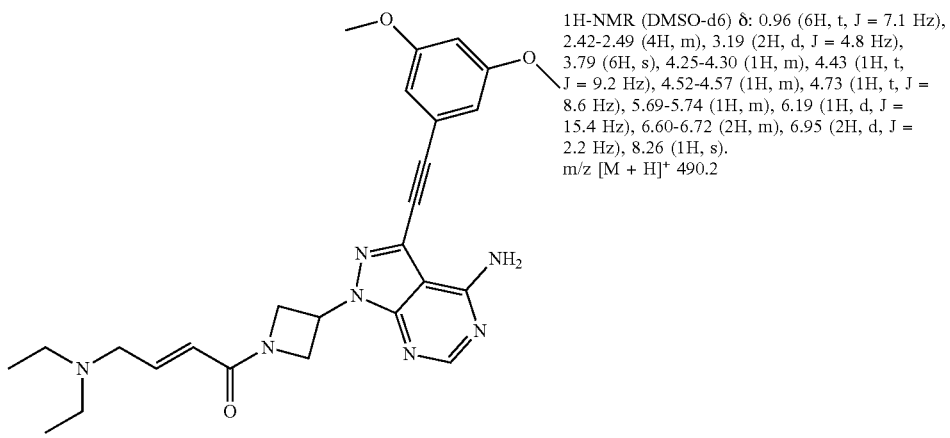 | 1H-NMR (DMSO-d6) δ: 0.96 (6H, t, J = 7.1 Hz), 2.42-2.49 (4H, m), 3.19 (2H, d, J = 4.8 Hz), 3.79 (6H, s), 4.25-4.30 (1H, m), 4.43 (1H, t, J = 9.2 Hz), 4.52-4.57 (1H, m), 4.73 (1H, t, J = 8.6 Hz), 5.69-5.74 (1H, m), 6.19 (1H, d, J = 15.4 Hz), 6.60-6.72 (2H, m), 6.95 (2H, d, J = 2.2 Hz), 8.26 (1H, s).<br>m/z [M + H]$^+$ 490.2 |
|---|---|---|
| 18 | 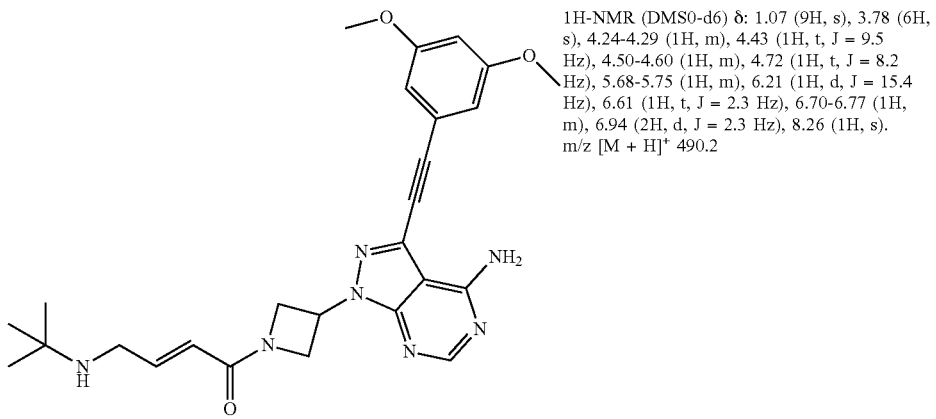 | 1H-NMR (DMS0-d6) δ: 1.07 (9H, s), 3.78 (6H, s), 4.24-4.29 (1H, m), 4.43 (1H, t, J = 9.5 Hz), 4.50-4.60 (1H, m), 4.72 (1H, t, J = 8.2 Hz), 5.68-5.75 (1H, m), 6.21 (1H, d, J = 15.4 Hz), 6.61 (1H, t, J = 2.3 Hz), 6.70-6.77 (1H, m), 6.94 (2H, d, J = 2.3 Hz), 8.26 (1H, s).<br>m/z [M + H]$^+$ 490.2 |

| 19 | 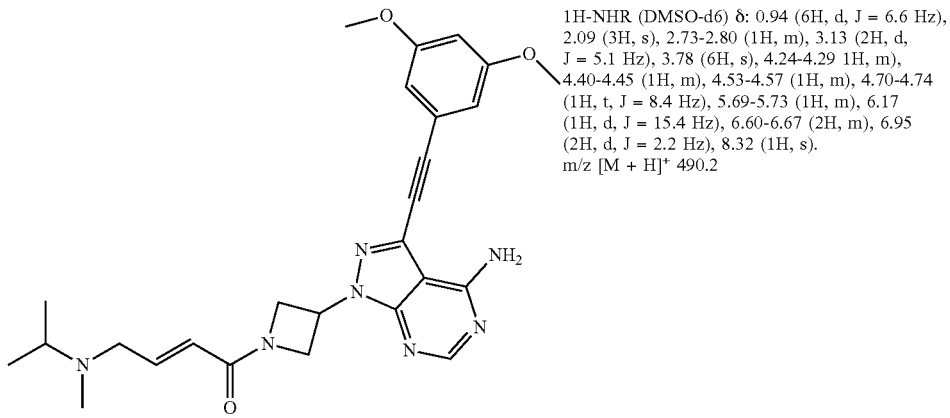 | 1H-NHR (DMSO-d6) δ: 0.94 (6H, d, J = 6.6 Hz), 2.09 (3H, s), 2.73-2.80 (1H, m), 3.13 (2H, d, J = 5.1 Hz), 3.78 (6H, s), 4.24-4.29 1H, m), 4.40-4.45 (1H, m), 4.53-4.57 (1H, m), 4.70-4.74 (1H, t, J = 8.4 Hz), 5.69-5.73 (1H, m), 6.17 (1H, d, J = 15.4 Hz), 6.60-6.67 (2H, m), 6.95 (2H, d, J = 2.2 Hz), 8.32 (1H, s). m/z [M + H]$^+$ 490.2 |
| 20 | 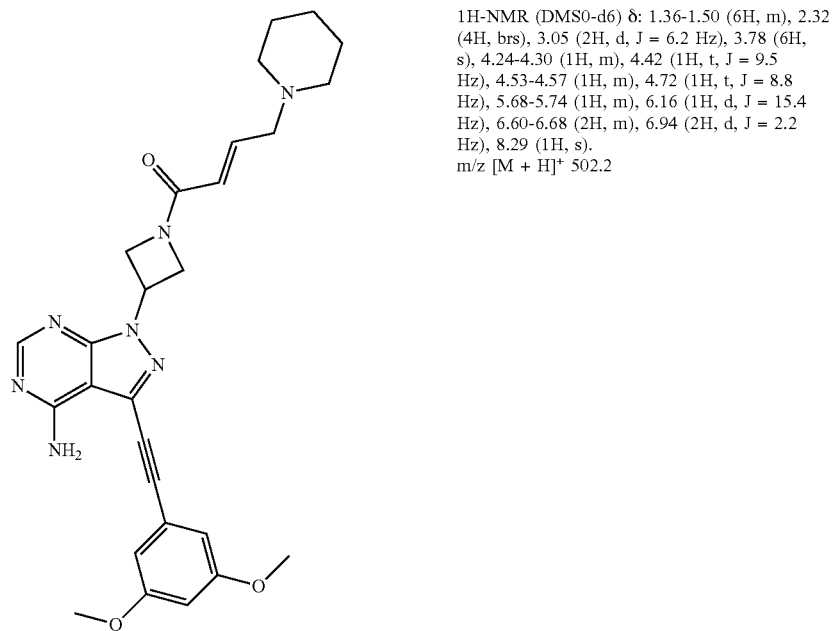 | 1H-NMR (DMS0-d6) δ: 1.36-1.50 (6H, m), 2.32 (4H, brs), 3.05 (2H, d, J = 6.2 Hz), 3.78 (6H, s), 4.24-4.30 (1H, m), 4.42 (1H, t, J = 9.5 Hz), 4.53-4.57 (1H, m), 4.72 (1H, t, J = 8.8 Hz), 5.68-5.74 (1H, m), 6.16 (1H, d, J = 15.4 Hz), 6.60-6.68 (2H, m), 6.94 (2H, d, J = 2.2 Hz), 8.29 (1H, s). m/z [M + H]$^+$ 502.2 |

TABLE 6
| 21 | 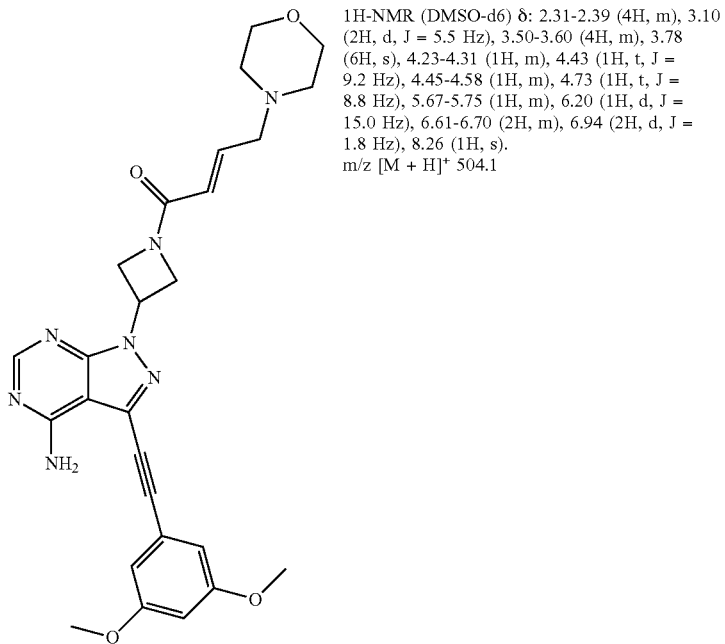 | 1H-NMR (DMSO-d6) δ: 2.31-2.39 (4H, m), 3.10 (2H, d, J = 5.5 Hz), 3.50-3.60 (4H, m), 3.78 (6H, s), 4.23-4.31 (1H, m), 4.43 (1H, t, J = 9.2 Hz), 4.45-4.58 (1H, m), 4.73 (1H, t, J = 8.8 Hz), 5.67-5.75 (1H, m), 6.20 (1H, d, J = 15.0 Hz), 6.61-6.70 (2H, m), 6.94 (2H, d, J = 1.8 Hz), 8.26 (1H, s). m/z [M + H]+ 504.1 |
|---|---|---|
| 22 | 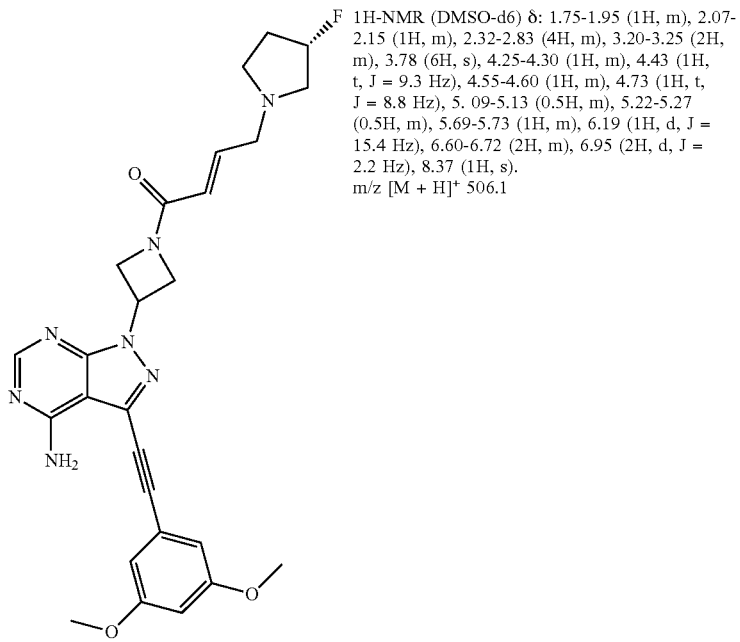 | 1H-NMR (DMSO-d6) δ: 1.75-1.95 (1H, m), 2.07-2.15 (1H, m), 2.32-2.83 (4H, m), 3.20-3.25 (2H, m), 3.78 (6H, s), 4.25-4.30 (1H, m), 4.43 (1H, t, J = 9.3 Hz), 4.55-4.60 (1H, m), 4.73 (1H, t, J = 8.8 Hz), 5. 09-5.13 (0.5H, m), 5.22-5.27 (0.5H, m), 5.69-5.73 (1H, m), 6.19 (1H, d, J = 15.4 Hz), 6.60-6.72 (2H, m), 6.95 (2H, d, J = 2.2 Hz), 8.37 (1H, s). m/z [M + H]+ 506.1 |

TABLE 6-continued
| 23 | 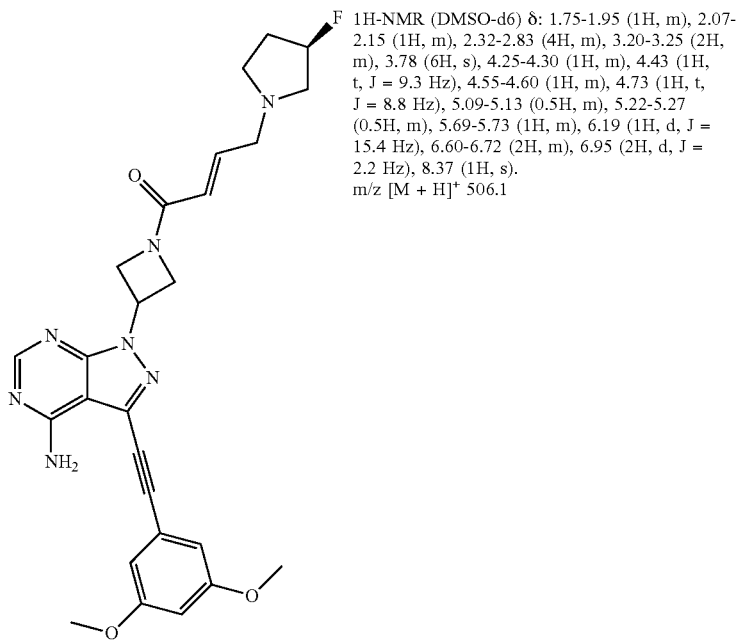 | 1H-NMR (DMSO-d6) δ: 1.75-1.95 (1H, m), 2.07-2.15 (1H, m), 2.32-2.83 (4H, m), 3.20-3.25 (2H, m), 3.78 (6H, s), 4.25-4.30 (1H, m), 4.43 (1H, t, J = 9.3 Hz), 4.55-4.60 (1H, m), 4.73 (1H, t, J = 8.8 Hz), 5.09-5.13 (0.5H, m), 5.22-5.27 (0.5H, m), 5.69-5.73 (1H, m), 6.19 (1H, d, J = 15.4 Hz), 6.60-6.72 (2H, m), 6.95 (2H, d, J = 2.2 Hz), 8.37 (1H, s).<br>m/z [M + H]⁺ 506.1 |
|---|---|---|
TABLE 7
| 24 | 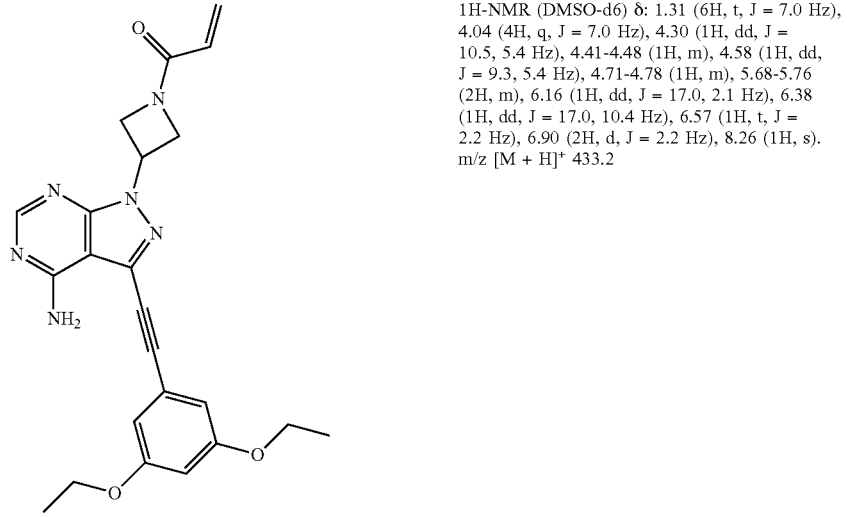 | 1H-NMR (DMSO-d6) δ: 1.31 (6H, t, J = 7.0 Hz), 4.04 (4H, q, J = 7.0 Hz), 4.30 (1H, dd, J = 10.5, 5.4 Hz), 4.41-4.48 (1H, m), 4.58 (1H, dd, J = 9.3, 5.4 Hz), 4.71-4.78 (1H, m), 5.68-5.76 (2H, m), 6.16 (1H, dd, J = 17.0, 2.1 Hz), 6.38 (1H, dd, J = 17.0, 10.4 Hz), 6.57 (1H, t, J = 2.2 Hz), 6.90 (2H, d, J = 2.2 Hz), 8.26 (1H, s).<br>m/z [M + H]⁺ 433.2 |
|---|---|---|

| 25 | 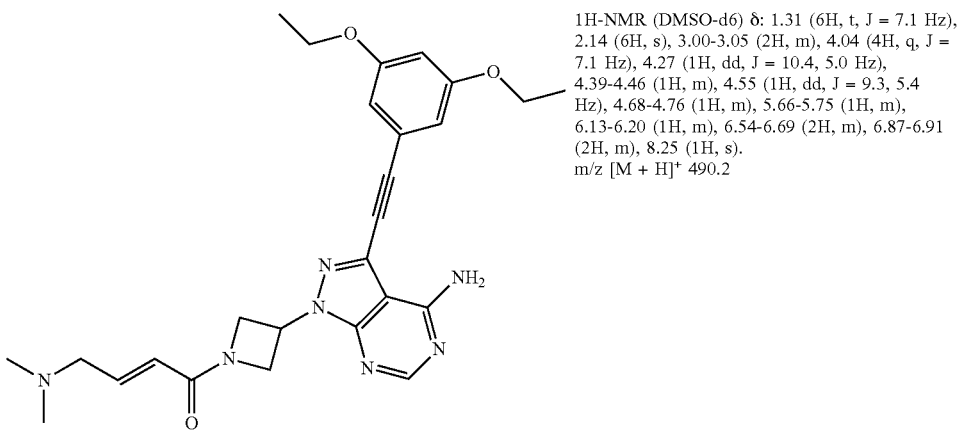 | 1H-NMR (DMSO-d6) δ: 1.31 (6H, t, J = 7.1 Hz), 2.14 (6H, s), 3.00-3.05 (2H, m), 4.04 (4H, q, J = 7.1 Hz), 4.27 (1H, dd, J = 10.4, 5.0 Hz), 4.39-4.46 (1H, m), 4.55 (1H, dd, J = 9.3, 5.4 Hz), 4.68-4.76 (1H, m), 5.66-5.75 (1H, m), 6.13-6.20 (1H, m), 6.54-6.69 (2H, m), 6.87-6.91 (2H, m), 8.25 (1H, s).<br>m/z [M + H]⁺ 490.2 |
|---|---|---|
| 26 | 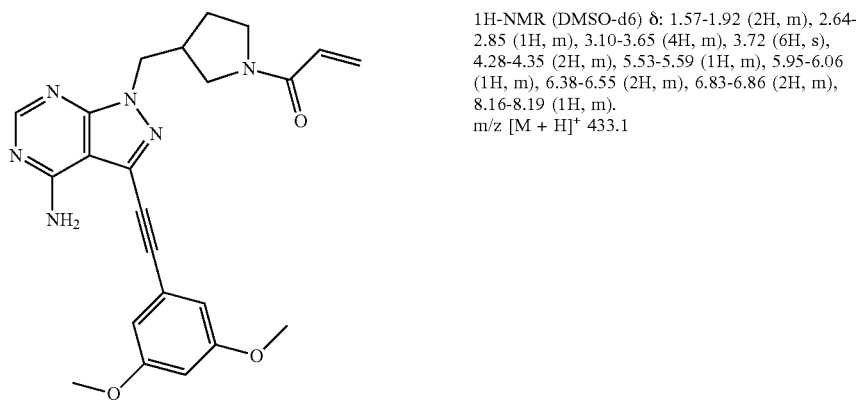 | 1H-NMR (DMSO-d6) δ: 1.57-1.92 (2H, m), 2.64-2.85 (1H, m), 3.10-3.65 (4H, m), 3.72 (6H, s), 4.28-4.35 (2H, m), 5.53-5.59 (1H, m), 5.95-6.06 (1H, m), 6.38-6.55 (2H, m), 6.83-6.86 (2H, m), 8.16-8.19 (1H, m).<br>m/z [M + H]⁺ 433.1 |
| 27 | 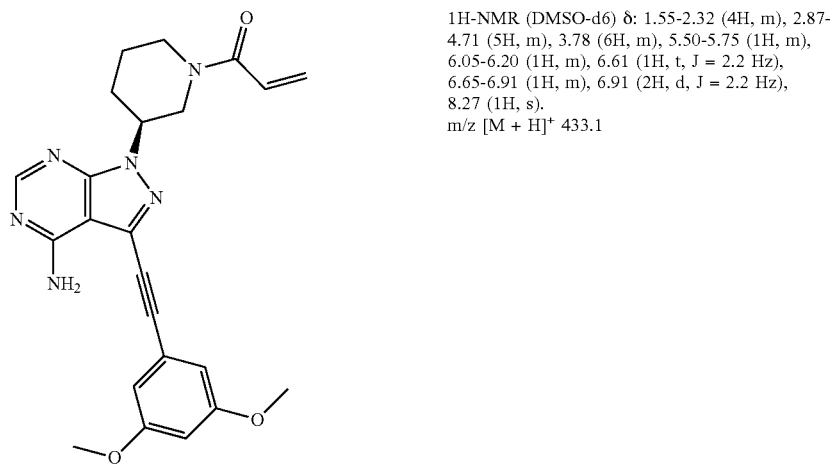 | 1H-NMR (DMSO-d6) δ: 1.55-2.32 (4H, m), 2.87-4.71 (5H, m), 3.78 (6H, m), 5.50-5.75 (1H, m), 6.05-6.20 (1H, m), 6.61 (1H, t, J = 2.2 Hz), 6.65-6.91 (1H, m), 6.91 (2H, d, J = 2.2 Hz), 8.27 (1H, s).<br>m/z [M + H]⁺ 433.1 |

TABLE 8
| | | |
|---|---|---|
| 28 | 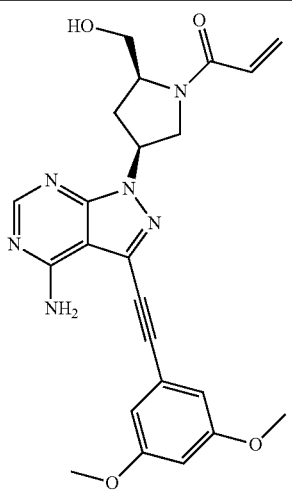 | 1H-NMR (DMSO-d6) δ: 2.48-2.50 (2H, m), 3.27-4.35 (11H, m), 4.89 (0.5H, t, J = 5.7 Hz), 5.02 (0.5H, t, J = 5.7 Hz), 5.28-5.37 (1H, m), 5.66-5.71 (1H, m), 6.13-6.20 (1H, m), 6.60 (1H, t, J = 2.3 Hz), 6.93 (2H, d, J = 2.3 Hz), 8.26 (1H, s). m/z [M + H]+ 449.1 |
| 29 | 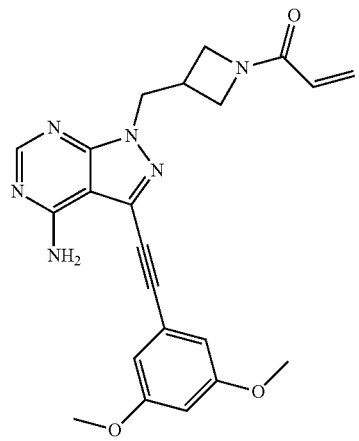 [SMILES: C=CC(=O)N1CC(Cn2nc(C#Cc3cc(OC)cc(OC)c3)c3c(N)ncnc32)C1] | 1H-NMR (CDCl3) δ: 3.20-3.35 (1H, m), 3.81 (6H, s), 3.91-4.02 (1H, m), 4.14-4.38 (3H, m), 4.58-4.70 (2H, m), 5.66 (1H, d, J = 10.5 Hz), 5.85-6.05 (2H, m), 6.16 (1H, dd, J = 17.0, 10.4 Hz), 6.33 (1H, d, J = 17.1 Hz), 6.54 (1H, s), 6.74 (2H, dd, J = 3.3, 2.6 Hz), 8.35 (1H, s). m/z [M + H]+ 419.1 |
| 30 | 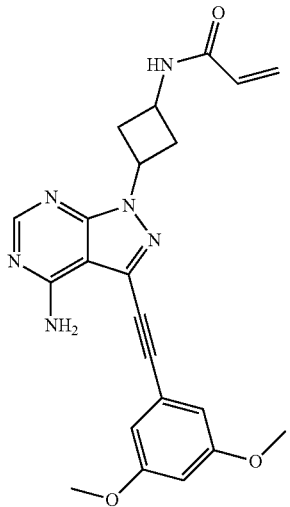 [SMILES: C=CC(=O)NC1CC(n2nc(C#Cc3cc(OC)cc(OC)c3)c3c(N)ncnc32)C1] | m/z [M + H]+ 419.2 |

TABLE 8-continued
| 31 | 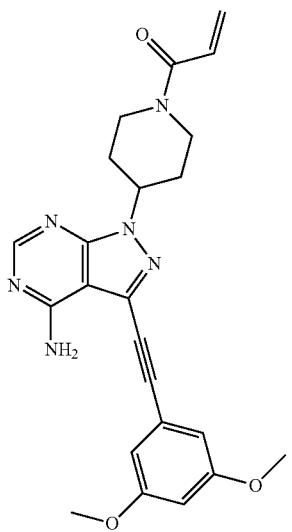 [SMILES: C=CC(=O)N1CCC(n2nc(C#Cc3cc(OC)cc(OC)c3)c3c(N)ncnc32)CC1] | 1H-NMR (CDCl3) δ: 2.08-2.10 (2H, m), 2.20-2.30 (4H, m), 2.81-2.98 (1H, m), 3.22-3.40 (1H, m), 3.82 (6H, s), 4.15-4.25 (1H, m), 4.80-4.88 (1H, m) 4.96-5.04 (1H, m), 5.72 (1H, dd, J = 10.8, 2.0 Hz), 6.30 (1H, dd, J = 16.8, 2.0 Hz), 6.54 (1H, t, J = 12.0 Hz) 6.61 (1H, dd, J = 17.2, 10.8 Hz), 6.73 (2H, d, J = 2.4 Hz), 8.42 (1H, s)<br>m/z [M + H]⁺ 433.2 |
TABLE 9
| 32 | 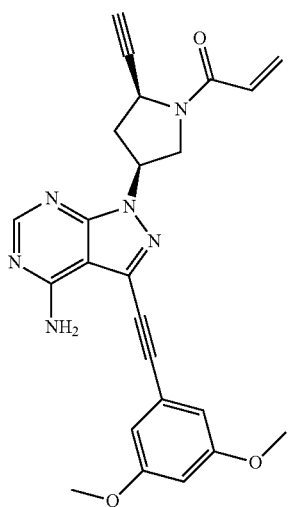 [SMILES: C#C[C@@H]1C[C@H](n2nc(C#Cc3cc(OC)cc(OC)c3)c3c(N)ncnc32)CN1C(=O)C=C] | 1H-NMR (CDCl3) δ: 2.34-2.42 (1H, m), 2.80-3.10 (2H, m), 3.82 (6H, s), 4.05-4.20 (2H, m), 4.20-4.50 (1H, m), 4.70-4.95 (1H, m), 5.30-5.40 (1H, m), 5.75-5.80 (1H, m), 5.98 (2H, brs), 6.40-6.50 (1H, m), 6.54 (1H, s), 6.70-6.73 (2H, m), 8.38 (1H, m).<br>m/z [M + H]⁺ 443.1 |
| 33 | 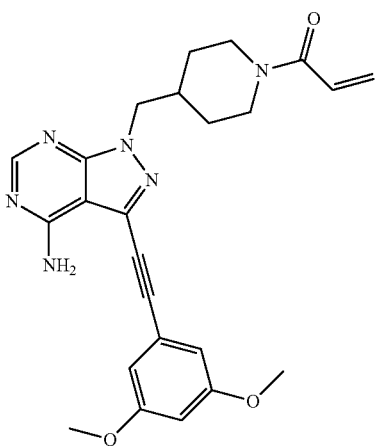 [SMILES: C=CC(=O)N1CCC(Cn2nc(C#Cc3cc(OC)cc(OC)c3)c3c(N)ncnc32)CC1] | m/z [M + H]⁺ 447.2 |

TABLE 9-continued
| 34 | 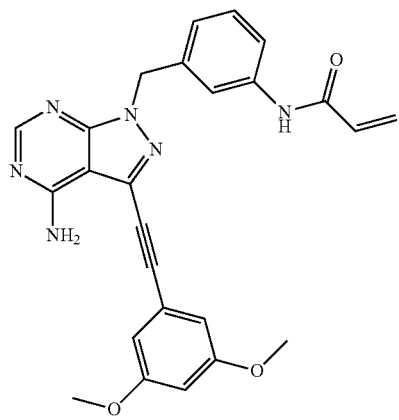 [SMILES: C=CC(=O)Nc1cccc(Cn2nc(C#Cc3cc(OC)cc(OC)c3)c3c(N)ncnc32)c1] | 1H-NMR (DMSO-d6) δ: 3.77 (6H, s), 5.50 (2H, s), 5.72 (1H, dd, J = 10.2, 2.1 Hz), 6.22 (1H, dd, J = 17.1, 2.1 Hz), 6.38 (1H, dd, J = 17.1, 10.2 Hz), 6.59 (1H, t, J = 2.3 Hz), 6.90 (2H, d, J = 2.3 Hz), 7.00 (1H, d, J = 7.8 Hz), 7.29 (1H, t, J = 7.8 Hz), 7.45 (1H, s), 7.63-7.66 (1H, m), 8.28 (1H, s), 10.12 (1H, s). m/z [M + H]+ 455.2 |
|---|---|---|
| 35 | 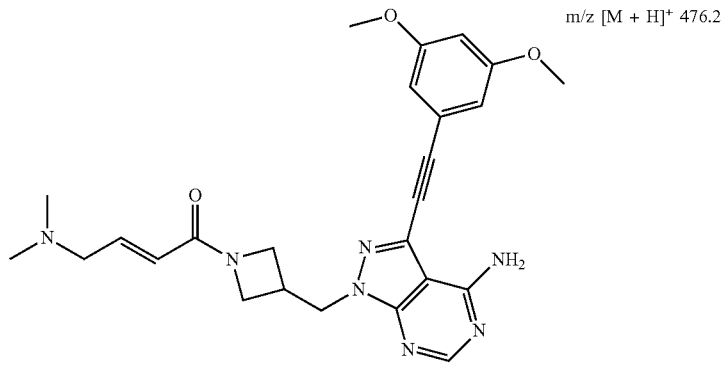 | m/z [M + H]+ 476.2 |
| 36 | 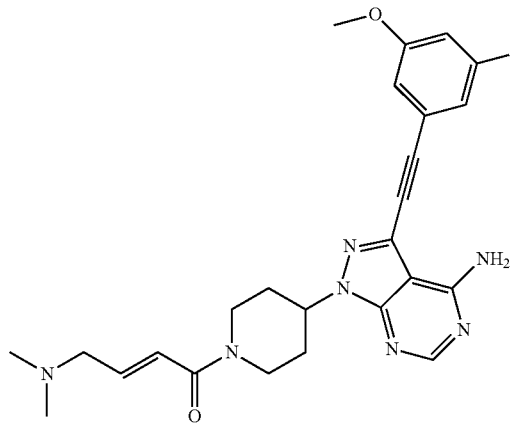 | 1H-NMR (CDCL3) δ: 2.09 (2H, d, J = 10.7 Hz), 2.29 (8H, m), 2.80-2.98 (1H, m), 3.12 (2H, d, J = 4.9 Hz), 3.19-3.40 (1H, m), 3.81 (6H, s), 4.12-4.32 (1H, m), 4.74-4.90 (1H, s), 4.94-4.96 (1H, m), 5.74-5.85 (2H, m), 6.43-6.55 (2H, m), 6.73 (2H, s), 6.80-6.80 (1H, m), 8.37 (1H, s). m/z [M + H]+ 490.2 |

TABLE 10
| 37 | 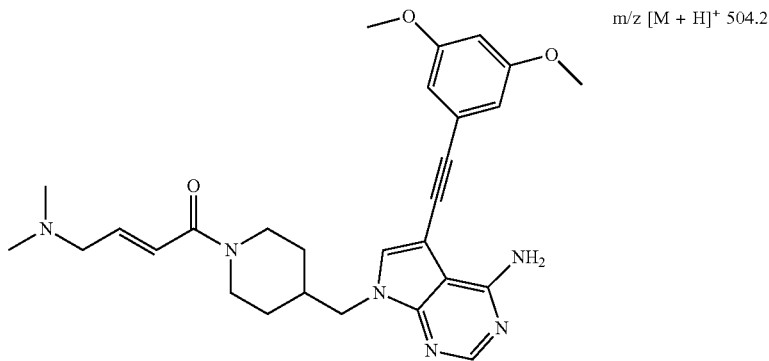 | m/z [M + H]⁺ 504.2 |
|---|---|---|
| 38 | 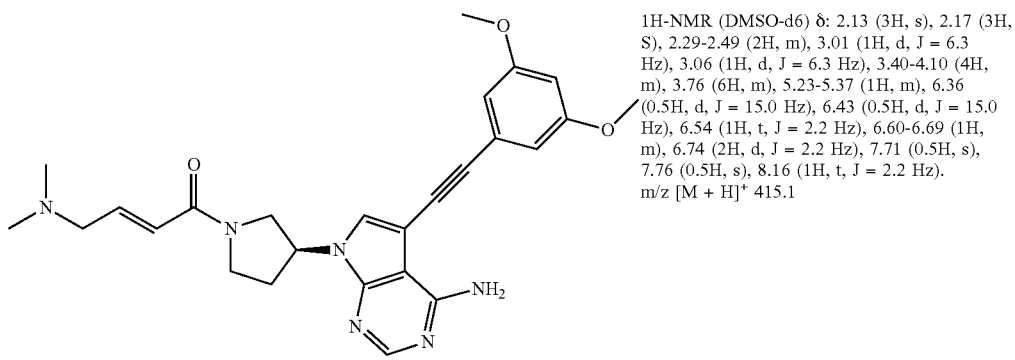 | 1H-NMR (DMSO-d6) δ: 2.13 (3H, s), 2.17 (3H, S), 2.29-2.49 (2H, m), 3.01 (1H, d, J = 6.3 Hz), 3.06 (1H, d, J = 6.3 Hz), 3.40-4.10 (4H, m), 3.76 (6H, m), 5.23-5.37 (1H, m), 6.36 (0.5H, d, J = 15.0 Hz), 6.43 (0.5H, d, J = 15.0 Hz), 6.54 (1H, t, J = 2.2 Hz), 6.60-6.69 (1H, m), 6.74 (2H, d, J = 2.2 Hz), 7.71 (0.5H, s), 7.76 (0.5H, s), 8.16 (1H, t, J = 2.2 Hz). m/z [M + H]⁺ 415.1 |
| 39 | 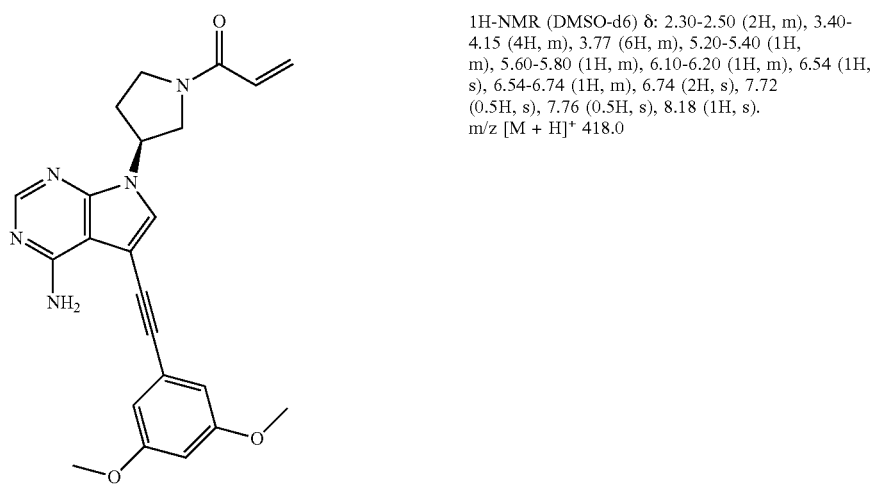 | 1H-NMR (DMSO-d6) δ: 2.30-2.50 (2H, m), 3.40-4.15 (4H, m), 3.77 (6H, m), 5.20-5.40 (1H, m), 5.60-5.80 (1H, m), 6.10-6.20 (1H, m), 6.54 (1H, s), 6.54-6.74 (1H, m), 6.74 (2H, s), 7.72 (0.5H, s), 7.76 (0.5H, s), 8.18 (1H, s). m/z [M + H]⁺ 418.0 |

TABLE 10-continued
| 40 | 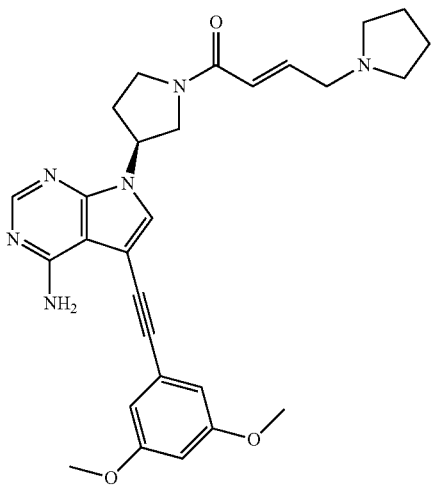 [SMILES: COc1cc(C#Cc2cn([C@H]3CCN(C(=O)/C=C/CN4CCCC4)C3)c3ncnc(N)c23)cc(OC)c1] | 1H-NMR (DMSO-d6) δ: 1.62-1.72 (4H, m), 2.28-2.51 (6H, m), 3.17 (1H, d, J = 5.9 Hz), 3.21 (1H, d, J = 5.9 Hz), 3.52-3.90 (9.5H, m), 4.02-4.12 (0.5H, m), 5.20-5.35 (1H, m), 6.30-6.45 (1H, m), 6.53 (1H, t, J = 2.4 Hz), 6.60-6.80 (3H, m), 7.71 (7.71 (0.5H, s), 7.75 (0.5H, s), 8.17 (0.5H, s), 8.18 (0.5H, m). m/z [M + H]$^+$ 501.1 |
TABLE 11
| 41 | 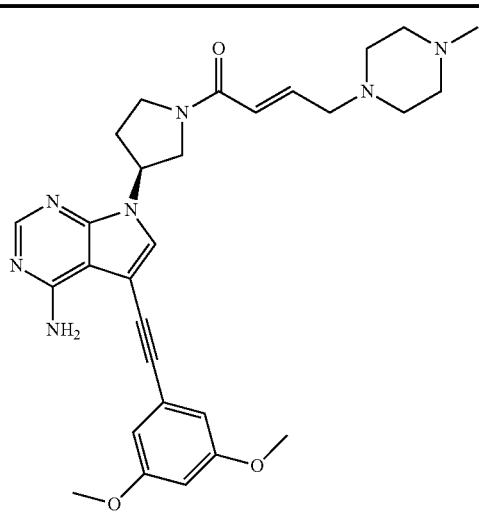 | 1H-NMR (DMSO-d6) δ: 2.15 (1.5H, s), 2.17 (1.5H, s), 2.18-2.42 (10H, m), 3.05 (1H, d, J = 6.2 Hz), 3.10 (1H, d, J = 6.2 Hz), 3.47-3.94 (9.5H, m), 4.02-4.10 (0.5H, m), 5.22-5.38 (1H, m), 6.32-6.45 (1H, m), 6.54 (1H, d, J = 1.8 Hz), 6.57-6.70 (1H, m), 6.74 (2H, d, J = 1.5 Hz), 7.70 (0.5H, s), 7.75 (0.5H, s), 8.14-8.17 (1H, m). m/z [M + H]$^+$ 530.2 |
| 42 | 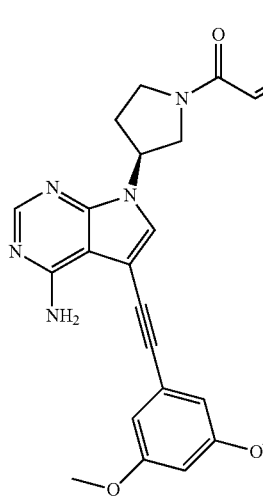 | 1H-NMR (DMSO-d6) δ: 1.32-1.42 (2H, m), 1.60-1.75 (2H, m), 1.95-2.06 (2H, m), 2.29-2.52 (2H, m), 2.60-2.70 (2H, m), 3.04 (1H, d, J = 6.2 Hz), 3.08 (1H, d, J = 6.2 Hz), 3.35-3.94 (10.5H, m), 4.05-4.10 (0.5H, m), 5.23-5.37 (1H, m), 6.34 (0.5H, d, J = 15.4 Hz), 6.41 (0.5H, d, J = 15.4 Hz), 6.53 (1H, t, J = 2.4 Hz), 6.59-6.68 (1H, m), 6.74 (2H, d, J = 1.5 Hz), 7.71 (0.5H, s), 7.75 (0.5H, s), 8.15-8.17 (1H, m). m/z [M + H]$^+$ 531.1 |

TABLE 11-continued
| 43 | 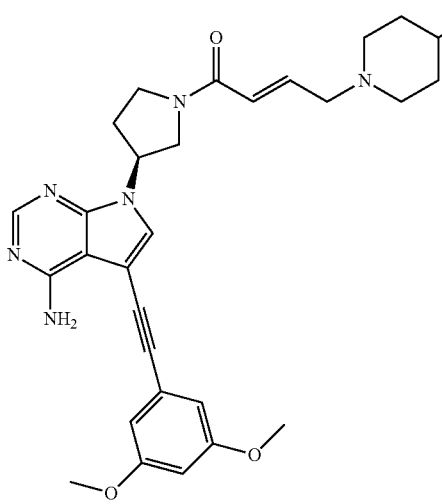 | 1H-NMR (DMSO-d6) δ: 1.60-1.90 (4H, m), 2.20-2.50 (6H, m), 3.07 (1H, d, J = 6.1 Hz), 3.12 (1H, d, J = 6.1 Hz), 3.52-3.89 (9.5H, m), 4.03-4.10 (0.5H, m), 4.55-4.80 (1H, m), 5.20-5.40 (1H, m), 6.35-6.46 (1H, m), 6.53 (1H, t, J = 2.2 Hz), 6.55-6.70 (1H, m), 6.74 (2H, d, J = 2.2 Hz), 7.71 (0.5H, s), 7.76 (0.5H, s), 8.17 (0.5H, s), 8.18 (0.5H, m).<br>m/z [M + H]+ 533.1 |
|---|---|---|
TABLE 12
| 44 | 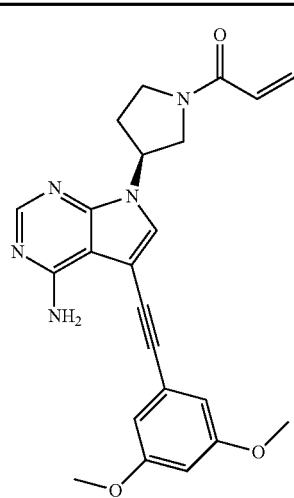 | 1H-NMR (DMSO-d6) δ: 2.18-2.54 (2H, m) 2.66-2.93 (4H, m), 3.18-3.24 (2H, m), 3.65-3.93 (9.5H, m), 4.04-4.10 (0.5H, m), 5.24-5.38 (1H, m), 6.35-6.50 (1H, m), 6.53 (3H, t, J = 2.2 Hz), 6.59-6.69 (1H, m), 6.74 (2H, d, J = 2.2 Hz), 7.71 (0.5H, s), 7.76 (0.5H, s), 8.17 (0.5H, s), 8.18 (0.5H, m).<br>m/z [M + H]+ 537.1 |
|---|---|---|
| 45 | 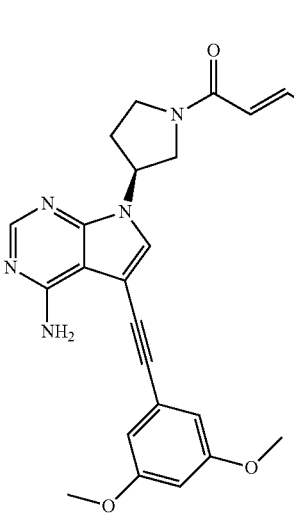 | 1H-NMR (DMSO-d6) δ: 1.88-2.02 (4H, m), 2.42-2.54 (6H, m), 3.15 (1H, d, J = 6.1 Hz), 3.20 (1H, d, J = 6.1 Hz), 3.49-3.92 (9.5H, m), 4.05-4.10 (0.5H, m), 5.22-5.38 (1H, m), 6.38-6.48 (1H, m), 6.54 (1H, t, J = 2.4 Hz), 6.60-6.70 (1H, m), 6.14 (2H, d, J = 2.4 Hz), 1.71 (0.5H, s), 7.76 (0.5H, s), 8.17 (0.5H, s), 8.18 (0.5H, m).<br>m/z [M + H]+ 551.1 |

TABLE 12-continued
| 46 | 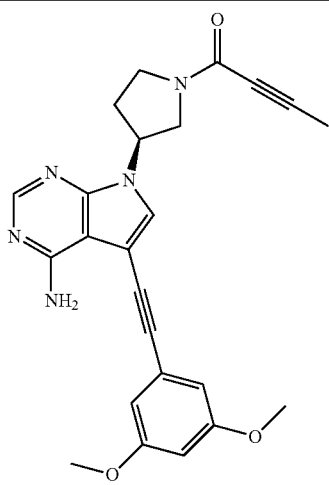 | 1H-NMR (DMSO-d6) δ: 1.97 (1.5H, s), 2.04 (1.5H, s), 2.37-2.43 (2H, m), 2.97-3.89 (9.5H, m), 4.05-4.12 (0.5H, m), 5.25-5.35 (1H, m), 6.54 (1H, d, J = 2.4 Hz), 6.74 (2H, d, J = 2.4 Hz), 7.74 (0.5H, s), 7.76 (0.5H, s), 8.16 (0.5H, s), 8.17 (0.5H, s). m/z [M + H]⁺ 430.1 |
|---|---|---|
| 47 | 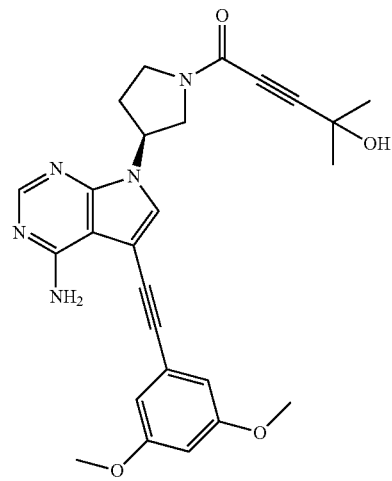 [SMILES: COc1cc(C#Cc2cn([C@H]3CCN(C(=O)C#CC(C)(C)O)C3)c3ncnc(N)c23)cc(OC)c1] | 1H-NMR (DMSO-d6) δ: 1.30 (3H, s), 1.37 (3H, s), 2.30-2.50 (2H, s), 3.06-4.10 (4H, s), 3.70 (6H, s), 5.20-5.35 (1H, m), 5.56 (0.5H, s), 5.64 (0.5H, s), 6.41 (1H, s), 6.68 (2H, d, J = 2.2 Hz), 7.70 (0.5H, s), 7.73 (0.5H, s), 8. 8.10 (0. 5H, s), 8.11 (0.5H, m). m/z [M + H]⁺ 474.4 |
TABLE 13
| 48 | 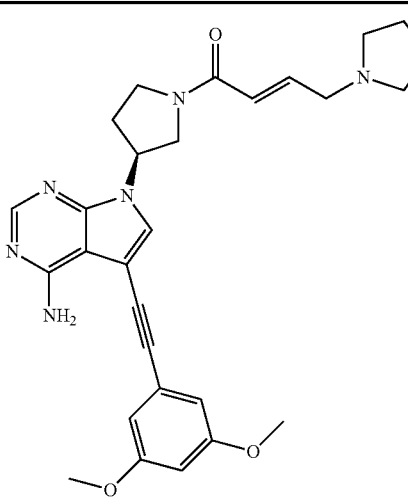 | 1H-NNR (DMSO-d6) δ: 1.76-2.85 (8H, m), 3.16-4.08 (12H, m), 5.05-5.38 (2H, m), 6.35-6.48 (1H, m), 6.53 (1H, t, J = 2.3 Hz), 6.62-6.72 (1H, m), 6.74 (2H, d, J = 2.3 Hz), 7.71 (0.5H, s), 7.76 (0.5H, s), 8.17 (0.5H, s), 8.18 (0.5H, m). m/z [M + H]⁺ 519.1 |
|---|---|---|

TABLE 13-continued
| 49 | 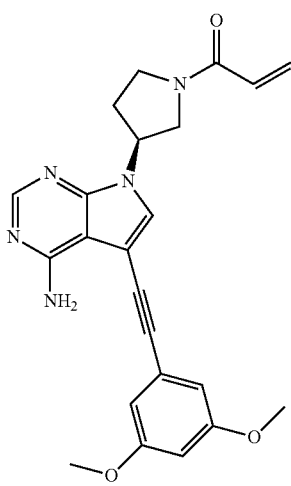 | 1H-NMR (DMSO-d6) δ: 1.76-2.85 (8H, m), 3.16-4.08 (12H, m), 5.05-5.38 (2H, m), 6.35-6.48 (1H, m), 6.53 (1H, t, J = 2.3 Hz), 6.62-6.72 (1H, m), 6.74 (2H, d, J = 2.3 Hz), 7.71 (0.5H, s), 7.76 (0.5H, s), 8.17 (0.5H, s), 8.18 (0.5H, m). m/z [M + H]$^+$ 519.1 |
| --- | --- | --- |
| 50 | 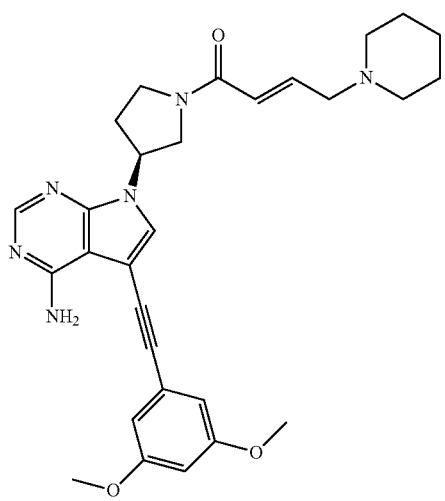 [SMILES: COc1cc(C#Cc2cn([C@H]3CCN(C(=O)/C=C/CN4CCCCC4)C3)c3ncnc(N)c23)cc(OC)c1] | 1H-NMR (DMSO-d6) δ: 1.20-1.50 (6H, m), 2.19-2.43 (6H, m), 2.96 (1H, d, J = 6.2 Hz), 3.00 (1H, d, J = 5.5 Hz), 3.31-4.02 (4H, m), 3.73 (6H, s), 5.15-5.30 (1H, m), 6.31 (1H, dd, J = 28.7, 15.0 Hz), 6.47 (1H, d, J = 2.1 Hz), 6.50-6.65 (1H, m), 6.66 (2H, d, J = 2.1 Hz), 7.63 (0.5H, s), 7.68 (0.5H, s), 8.10 (1H, s). m/z [M + H]$^+$ 515.1 |
| 51 | 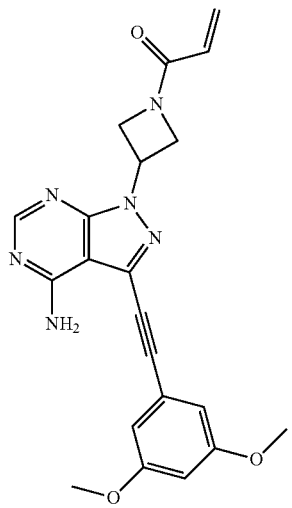 [SMILES: C=CC(=O)N1CC(n2nc(C#Cc3cc(OC)cc(OC)c3)c3c(N)ncnc32)C1] | 1H-NMR (DMSO-d6) δ: 3.76 (6H, s,), 4.20-4.27 (1H, m), 4.30-4.39 (1H, m), 4.50-4.60 (1H, m), 4.62-4.68 (1H, m), 5.50-5.60 (1H, m), 5.64 (1H, dd, J = 10.3, 2.3 Hz), 6.08 (1H, dd, J = 16.9, 2.3 Hz), 6.29 (1H, dd, J = 16.9, 10.3 Hz), 6.47 (1H, t, J = 2.1 Hz), 6.67 (2H, d, J = 2.1 Hz), 7.98 (1H, s), 8.09 (t, s). m/z [M + H]$^+$ 404.0 |

TABLE 14
| 52 | 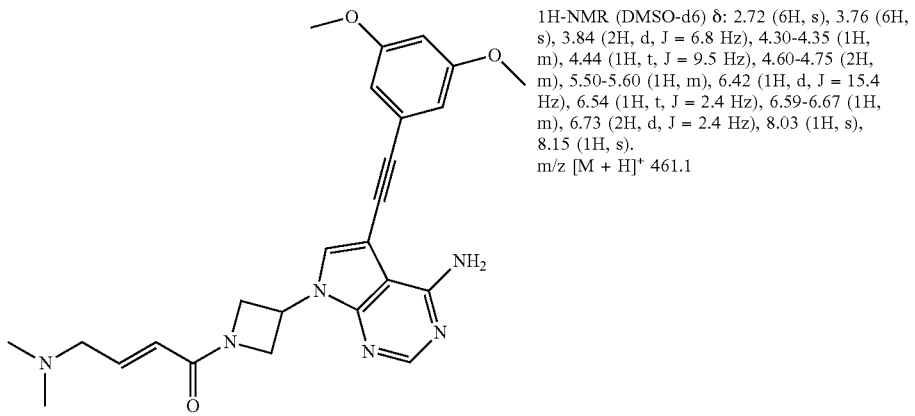 | 1H-NMR (DMSO-d6) δ: 2.72 (6H, s), 3.76 (6H, s), 3.84 (2H, d, J = 6.8 Hz), 4.30-4.35 (1H, m), 4.44 (1H, t, J = 9.5 Hz), 4.60-4.75 (2H, m), 5.50-5.60 (1H, m), 6.42 (1H, d, J = 15.4 Hz), 6.54 (1H, t, J = 2.4 Hz), 6.59-6.67 (1H, m), 6.73 (2H, d, J = 2.4 Hz), 8.03 (1H, s), 8.15 (1H, s).<br>m/z [M + H]⁺ 461.1 |
|---|---|---|
| 53 | 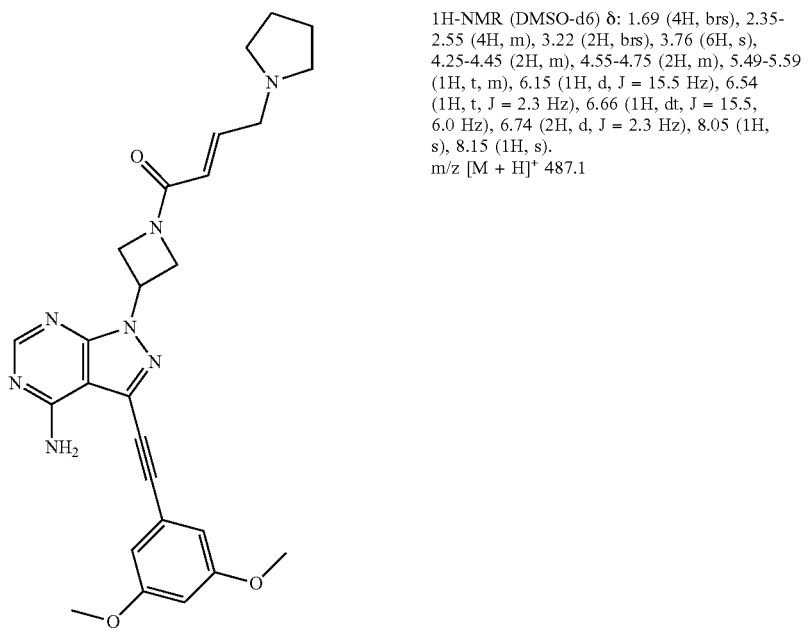 | 1H-NMR (DMSO-d6) δ: 1.69 (4H, brs), 2.35-2.55 (4H, m), 3.22 (2H, brs), 3.76 (6H, s), 4.25-4.45 (2H, m), 4.55-4.75 (2H, m), 5.49-5.59 (1H, t, m), 6.15 (1H, d, J = 15.5 Hz), 6.54 (1H, t, J = 2.3 Hz), 6.66 (1H, dt, J = 15.5, 6.0 Hz), 6.74 (2H, d, J = 2.3 Hz), 8.05 (1H, s), 8.15 (1H, s).<br>m/z [M + H]⁺ 487.1 |
| 54 | 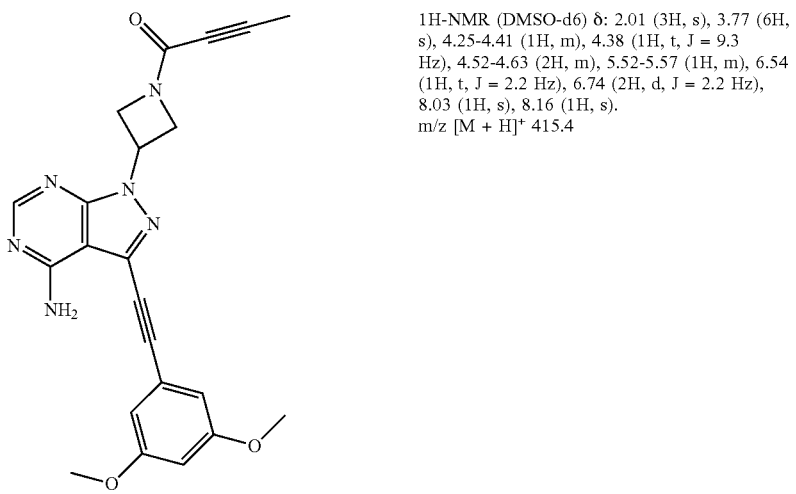 | 1H-NMR (DMSO-d6) δ: 2.01 (3H, s), 3.77 (6H, s), 4.25-4.41 (1H, m), 4.38 (1H, t, J = 9.3 Hz), 4.52-4.63 (2H, m), 5.52-5.57 (1H, m), 6.54 (1H, t, J = 2.2 Hz), 6.74 (2H, d, J = 2.2 Hz), 8.03 (1H, s), 8.16 (1H, s).<br>m/z [M + H]⁺ 415.4 |

TABLE 14-continued
| | | |
|---|---|---|
| 55 | 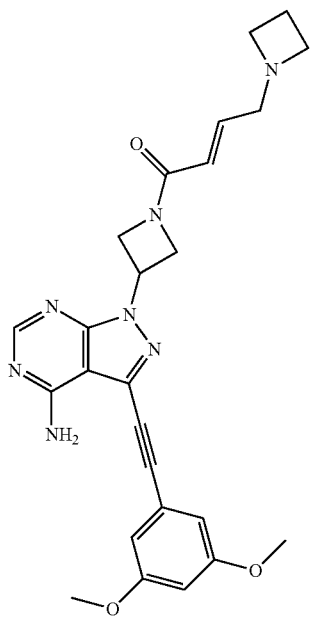 [SMILES: COc1cc(C#Cc2nn(C3CN(C(=O)/C=C/CN4CCC4)C3)c3ncnc(N)c23)cc(OC)c1] | 1H-NMR (DMSO-d6) δ: 1.94-2.00 (2H, m), 3.11-3.15 (6H, t, J = 7.0 Hz), 3.77 (6H, s), 4.25-4.28 (1H, m), 4.39 (1H, t, J = 9.3 Hz), 4.58-4.75 (2H, m), 5.50-5.58 (1H, m), 6.07 (1H, d, J = 15.4 Hz), 6.50-6.58 (2H, m), 6.74 (2H, d, J = 2.6 Hz), 8.05 (1H, s), 8.15 (1H, s).<br>m/z [M + H]$^+$ 473.1 |
TABLE 15
| | | |
|---|---|---|
| 56 | 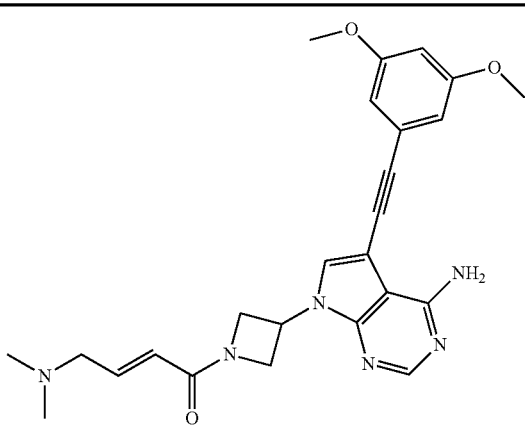 | 1H-NMR (DMSO-6) δ: 0.98 (3H, t, J = 7.1 Hz), 2.13 (3H, s), 2.35 (2H, q, J =7.2 Hz), 3.10 (2H, d, J = 6.2 Hz), 3.77 (6H, s), 4.24-4.29 (1H, m), 4.40 (1H, t, J = 9.5 Hz), 4.65-4.75 (2H, m), 5.53-5.57 (1H, m), 6.15 (1H, d, J = 15.4 Hz), 6.54 (1H, t, J = 2.5 Hz), 6.64 (1H, dt, J = 15.4, 6.1 Hz), 6.74 (2H, d, J = 2.5 Hz), 8.05 (1H, s), 8.15 (1H, s).<br>m/z [M + H]$^+$ 475.1 |
| 57 | 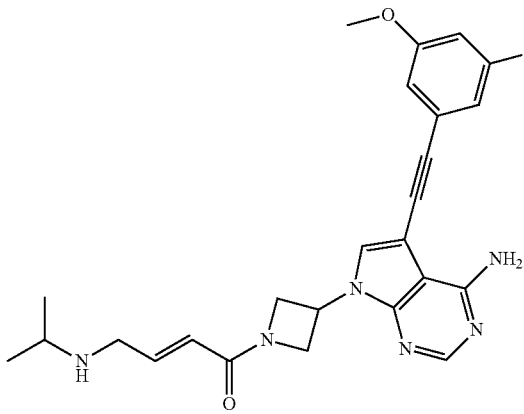 | 1H-NMR (DMSO-d6) δ: 0.95 (3H, d, J = 6.6 Hz), 1.14 (3H, d, J = 6.6 Hz), 3.05-3.15 (1H, m), 3.64 (2H, d, J = 5.9 Hz), 3.77 (6H, s), 4.22-4.70 (4H, m), 5.50-5.60 (1H, m), 6.25-6.36 (1H, m), 6.52-6.57 (1H, m), 6.63-6.70 (1H, m), 6.73-6.79 (2H, m), 8.02 (0.5H, s), 8.04 (0.5H, s), 8.16 (1H, s).<br>m/z [M + H]$^+$ 475.1 |

TABLE 15-continued
| 58 | 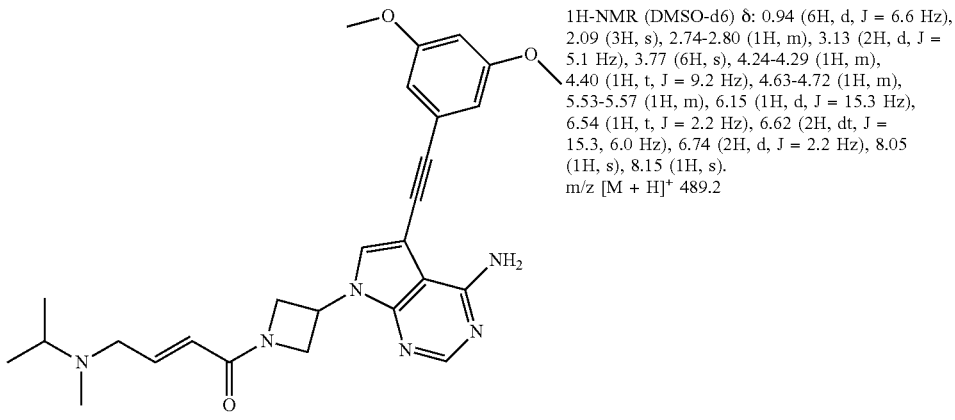 | 1H-NMR (DMSO-d6) δ: 0.94 (6H, d, J = 6.6 Hz), 2.09 (3H, s), 2.74-2.80 (1H, m), 3.13 (2H, d, J = 5.1 Hz), 3.77 (6H, s), 4.24-4.29 (1H, m), 4.40 (1H, t, J = 9.2 Hz), 4.63-4.72 (1H, m), 5.53-5.57 (1H, m), 6.15 (1H, d, J = 15.3 Hz), 6.54 (1H, t, J = 2.2 Hz), 6.62 (2H, dt, J = 15.3, 6.0 Hz), 6.74 (2H, d, J = 2.2 Hz), 8.05 (1H, s), 8.15 (1H, s). m/z [M + H]+ 489.2 |
TABLE 16
| 59 | 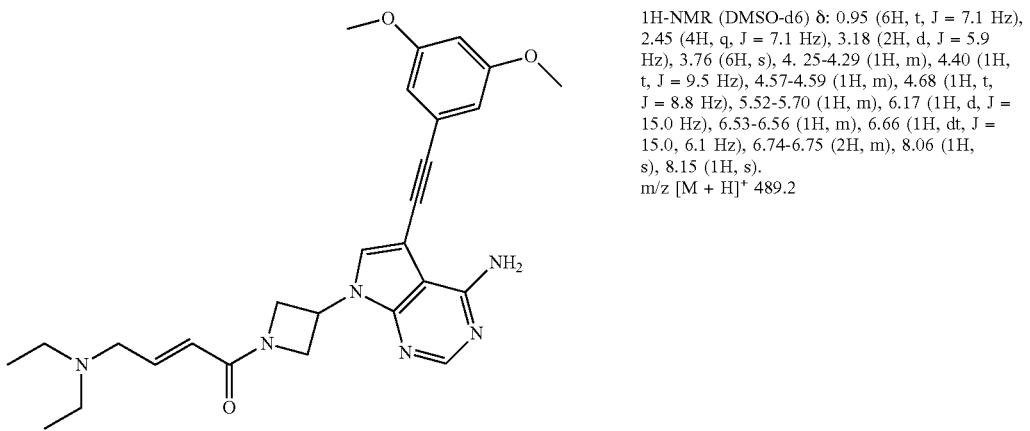 | 1H-NMR (DMSO-d6) δ: 0.95 (6H, t, J = 7.1 Hz), 2.45 (4H, q, J = 7.1 Hz), 3.18 (2H, d, J = 5.9 Hz), 3.76 (6H, s), 4.25-4.29 (1H, m), 4.40 (1H, t, J = 9.5 Hz), 4.57-4.59 (1H, m), 4.68 (1H, t, J = 8.8 Hz), 5.52-5.70 (1H, m), 6.17 (1H, d, J = 15.0 Hz), 6.53-6.56 (1H, m), 6.66 (1H, dt, J = 15.0, 6.1 Hz), 6.74-6.75 (2H, m), 8.06 (1H, s), 8.15 (1H, s). m/z [M + H]+ 489.2 |
| 60 | 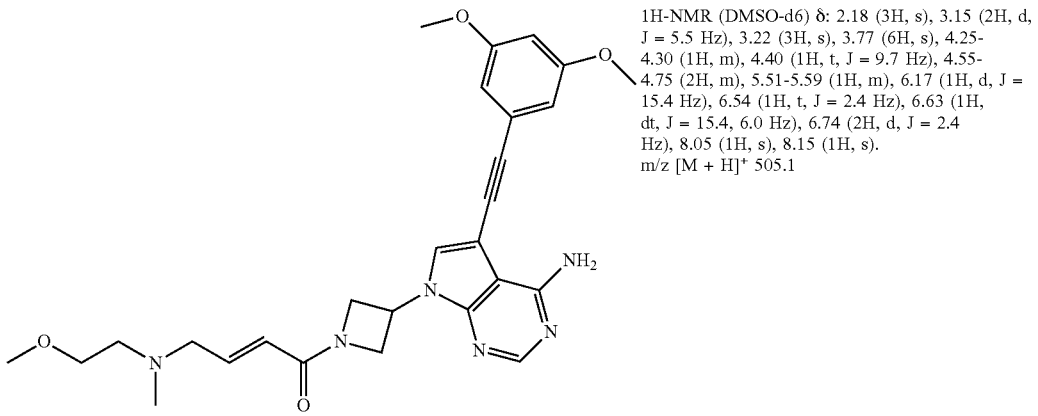 | 1H-NMR (DMSO-d6) δ: 2.18 (3H, s), 3.15 (2H, d, J = 5.5 Hz), 3.22 (3H, s), 3.77 (6H, s), 4.25-4.30 (1H, m), 4.40 (1H, t, J = 9.7 Hz), 4.55-4.75 (2H, m), 5.51-5.59 (1H, m), 6.17 (1H, d, J = 15.4 Hz), 6.54 (1H, t, J = 2.4 Hz), 6.63 (1H, dt, J = 15.4, 6.0 Hz), 6.74 (2H, d, J = 2.4 Hz), 8.05 (1H, s), 8.15 (1H, s). m/z [M + H]+ 505.1 |

TABLE 16-continued
| 61 | 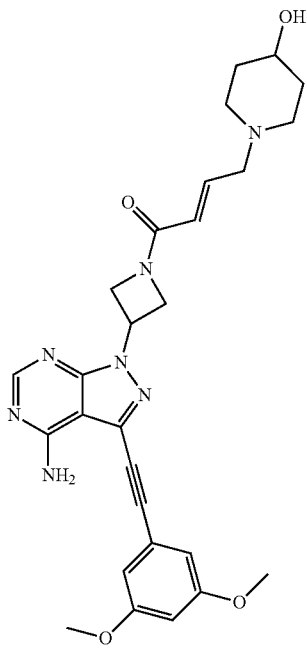 [SMILES: COc1cc(C#Cc2nn(C3CN(C(=O)/C=C/CN4CCC(O)CC4)C3)c3ncnc(N)c23)cc(OC)c1] | 1H-NMR (DMSO-d6) δ: 1.30-1.42 (2H, m), 1.65-1.75 (2H, m), 2.03 (2H, t, J = 10.3 Hz), 2.62-2.70 (2H, m), 3.06 (2H, d, J = 5.1 Hz), 3.77 (6H, s), 4.22-4.30 (1H, m), 4.40 (1H, t, J = 9.2 Hz), 4.55-4.72 (2H, m), 5.52-5.58 (1H, m), 6.13 (1H, d, J = 15.0 Hz), 6.54 (1H, t, J = 2.3 Hz), 6.58-6.65 (1H, m), 6.74 (2H, d, J = 2.3 Hz), 8.06 (1H, s), 8.15 (1H, s).<br>m/z [M + H]$^+$ 517.1 |
TABLE 17
| 62 | 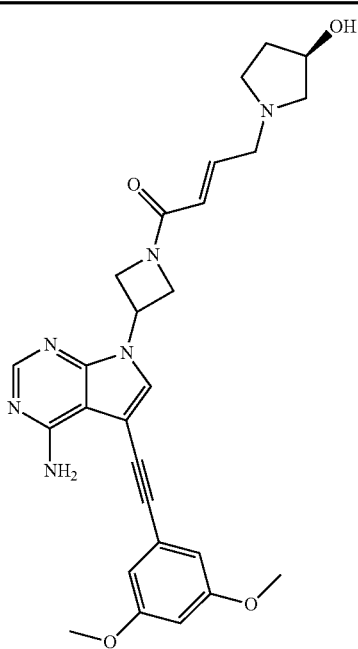 | 1H-NMR (DMSO-d6) δ: 1.48-1.58 (1H, m), 1.92-2.00 (1H, m), 2.31-2.71 (4H, m), 3.19 (2H, brs), 3.77 (6H, s), 4.15-4.30 (2H, m), 4.35-4.44 (1H, m), 4.55-4.72 (2H, m), 5.50-5.60 (1H, m), 6.15 (1H, d, J = 15.4 Hz), 6.54 (1H, t, J = 2.2 Hz), 6.60-6.70 (1H, m), 6.75 (2H, d, J = 2.2 Hz), 8.05 (1H, s), 8.15 (1H, d, J = 1.8 Hz).<br>m/z [M + H]$^+$ 503.1 |

TABLE 17-continued
| 63 | 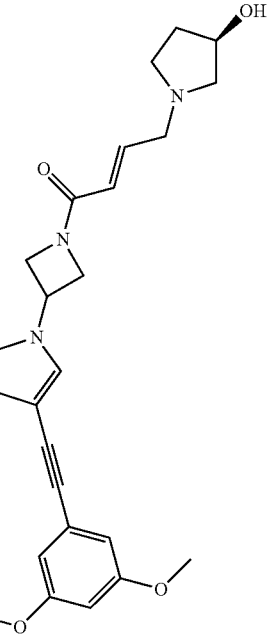 | 1H-NMR (DMSO-d6) δ: 1.48-1.58 (1H, m), 1.92-2.00 (1H, m), 2.31-2.71 (4H, m), 3.19 (2H, brs), 3.77 (6H, s), 4.15-4.30 (2H, m), 4.35-4.44 (1H, m), 4.55-4.72 (2H, m), 5.50-5.60 (1H, m), 6.15 (1H, d, J = 15.4 Hz), 6.54 (1H, t, J = 2.2 Hz), 6.60-6.70 (1H, m), 6.75 (2H, d, J = 2.2 Hz), 8.05 (1H, s), 8.15 (1H, d, J = 1.8 Hz). m/z [M + H]+ 503.1 |
| --- | --- | --- |
| 64 | 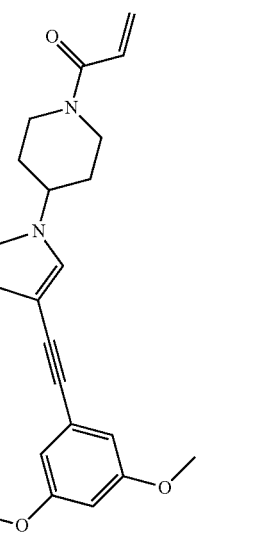 | 1H-NMR (CDCl3) δ: 1.67-2.22 (4H, m), 2.71-2.95 (1H, m), 3.19-3.35 (1H, m), 3.81 (6H, s), 4.09-4.25 (1H, m), 4.83-4.95 (2H, m), 5.61-5.78 (3H, m), 6.28-6.68 (5H, m), 7.24 (1H, s), 8.31 (1H, s). m/z [M + H]+ 422.2 |
| 65 | 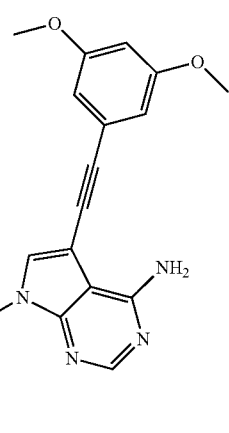 | 1H-NMR (CDCl3) δ: 1.65-2.00 (4H, m), 2.29 (6H, s), 2.77-2.92 (1H, m), 3.12 (2H, d, J = 5.9 Hz), 3.22-3.38 (1H, m), 3.81 (6H, s), 4.14-4.30 (1H, m), 4.85-4.97 (2H, m), 5.66 (2H, br s), 6.44-6.55 (2H, m), 6.65 (2H, d, J = 2.2 Hz), 6.84-6.95 (1H, m), 7.24 (1H, m), 8.31 (1H, s). m/z [M + H]+ 489.2 |

TABLE 18
| 66 | 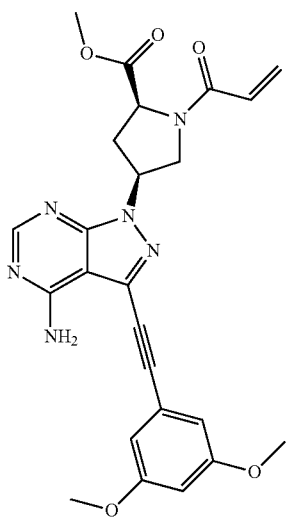 [SMILES: C=CC(=O)N1C[C@@H](n2nc(C#Cc3cc(OC)cc(OC)c3)c3c(N)ncnc32)C[C@H]1C(=O)OC] | 1H-NMR (CDCl3) δ: 2.37-2.48 (1H, m), 2.82-2.93 (1H, m), 3.41-3.52 (1H, m), 3.82 (9H, s), 3.86-3.95 (1H, m), 4.25-4.38 (1H, m), 4.69 (1H, t, J = 8.3 Hz), 5.43-5.56 (1H, m), 5.65-5.83 (2H, m), 6.36-6.50 (3H, m), 6.65 (2H, d, J = 2.0 Hz), 1.37 (1H, s), 8.30 (1H, s).<br>m/z [M + H]$^+$ 476.2 |
|---|---|---|
| 67 | 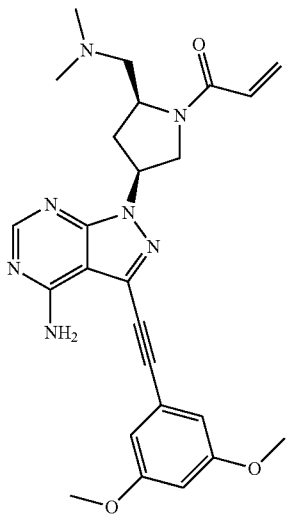 [SMILES: C=CC(=O)N1C[C@@H](n2nc(C#Cc3cc(OC)cc(OC)c3)c3c(N)ncnc32)C[C@H]1CN(C)C] | m/z [M + H]$^+$ 475.2 |
| 68 | 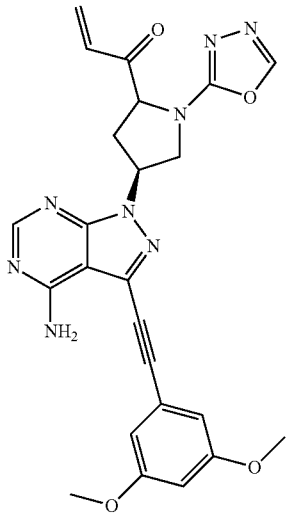 [SMILES: C=CC(=O)C1C[C@H](n2nc(C#Cc3cc(OC)cc(OC)c3)c3c(N)ncnc32)CN1c1nnco1] | 1H-NMR (CDCl3) δ: 2.75-2.95 (1H, m), 2.99-3.15 (1H, m), 3.82 (6H, s), 4.00 (1H, t, J = 9.8 Hz), 4.32-4.50 (1H, m), 5.44-5.85 (5H, m), 6.44 (2H, d, J = 5.9 Hz), 6.49 (1H, t, J = 2.2 Hz), 6.66 (2H, d, J = 2.2 Hz), 1.44 (1H, br s), 8.30 (1H, s), 8.40 (1H, s).<br>m/z [M + H]$^+$ 486.1 |

TABLE 18-continued
| | | |
|---|---|---|
| 69 | 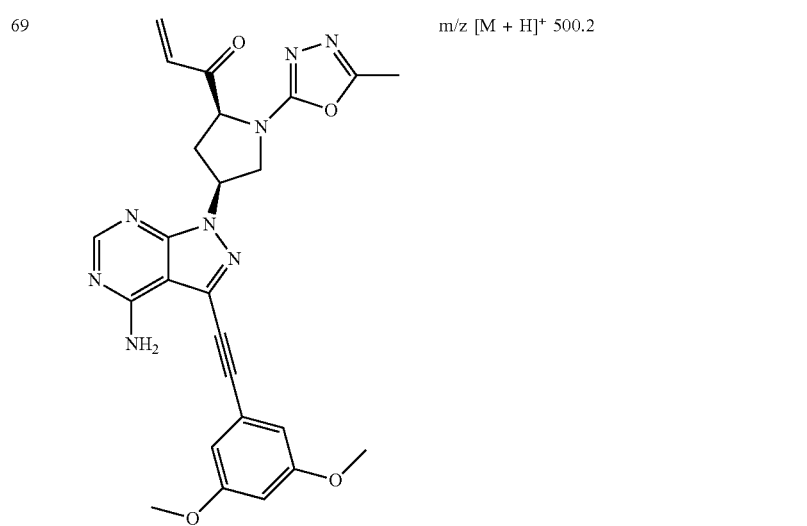 | m/z [M + H]+ 500.2 |
| 70 | 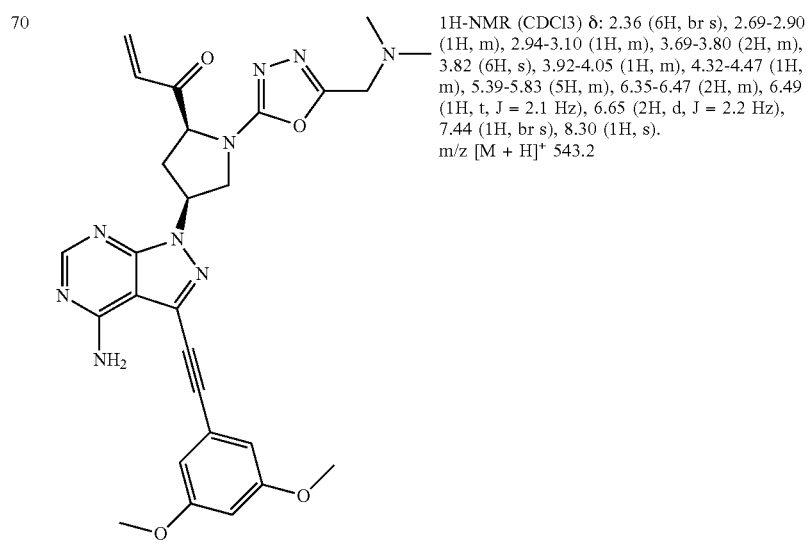 | 1H-NMR (CDCl3) δ: 2.36 (6H, br s), 2.69-2.90 (1H, m), 2.94-3.10 (1H, m), 3.69-3.80 (2H, m), 3.82 (6H, s), 3.92-4.05 (1H, m), 4.32-4.47 (1H, m), 5.39-5.83 (5H, m), 6.35-6.47 (2H, m), 6.49 (1H, t, J = 2.1 Hz), 6.65 (2H, d, J = 2.2 Hz), 7.44 (1H, br s), 8.30 (1H, s).<br>m/z [M + H]+ 543.2 |

TABLE 19
| | | |
|---|---|---|
| 71 | 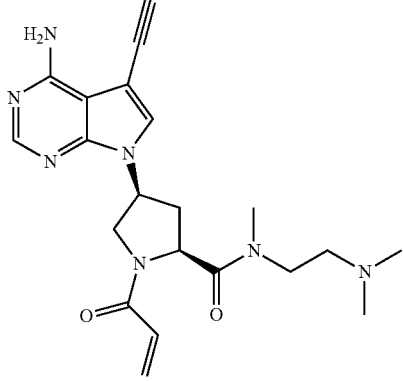 | 1H-NMR (CDCl3) δ: 2.30 (6H, d, J = 7.6 Hz), 2.35-2.68 (3H, m), 2.77-2.92 (1H, m), 3.14 (3H, d, J = 79.5 Hz), 3.31-3.47 (1H, m), 3.69-3.81 (1H, m), 3.82 (6H, s), 3.95 (2H, q, J = 9.9 Hz), 4.35 (1H, t, J = 8.9 Hz), 5.08 (1H, t, J = 7.3 Hz), 5.50-5.79 (4H, m), 6.37-6.52 (3H, m), 6.65 (2H, t, J = 2.2 Hz), 7.59 (1H, d, J = 28.0 Hz), 8.30 (1H, s).<br>m/z [M + H]$^+$ 546.3 |
| 72 | 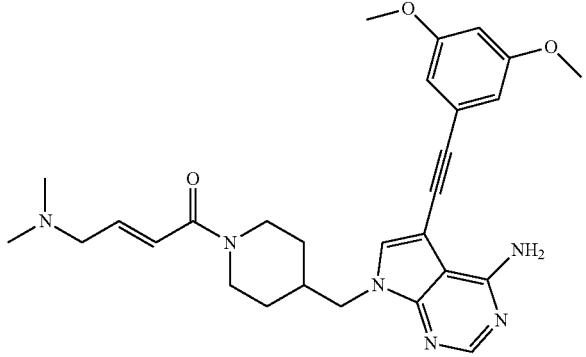 | m/z [M + H]$^+$ 503.3 |
| 73 | 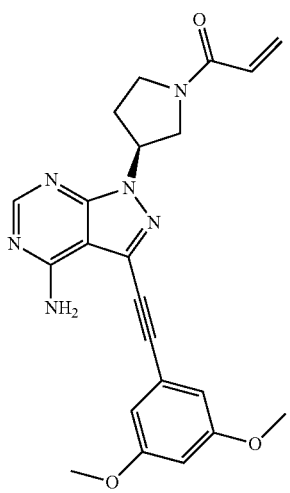 [SMILES: C=CC(=O)N1CC[C@H](n2nc(C#Cc3cc(OC)cc(OC)c3)c3c(N)ncnc32)C1] | 1H-NMR (DMSO-d6) δ: 2.21-2.44 (2H, m), 3.34-3.87 (9.5H, m), 4.00-4.10 (0.5H, m), 5.02-5.18 (1H, m), 5.58-5.68 (1H, m), 5.88 (2H, brs), 6.05-6.18 (1H, m), 6.45-6.65 (4H, m), 6.82-6.88 (1H, m), 7.60-7.63 (2H, m).<br>m/z [M + H]$^+$ 417.5 |

TABLE 20

| Ref. Ex Comp. | Structural formula | Physical properties |
|---|---|---|
| 1 | | m/z [M + H]+ 441.2 |
| 2 | | m/z [M + H]+ 289.1 |
| 3 | | m/z [M + H]+ 421.2 |

TABLE 20-continued

| Ref. Ex Comp. | Structural formula | Physical properties |
|---|---|---|
| 4 | 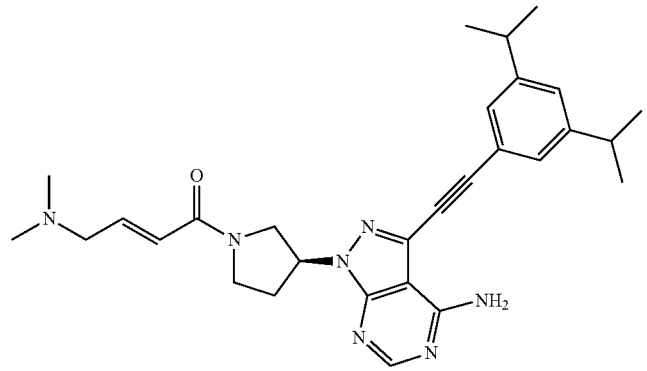 [SMILES: CC(C)c1cc(C#Cc2nn([C@H]3CCN(C(=O)/C=C/CN(C)C)C3)c3ncnc(N)c23)cc(C(C)C)c1] | m/z [M + H]+ 500.3 |
| 5 | 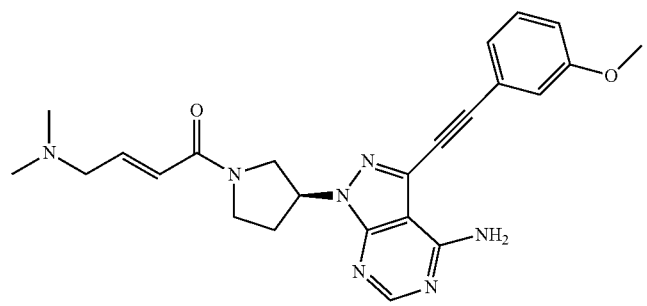 | m/z [M + H]+ 446.2 |
| 6 | 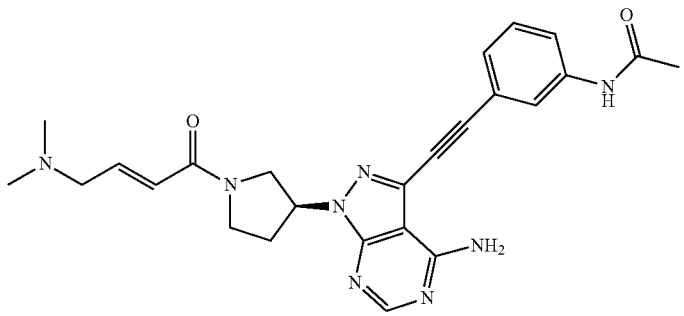 [SMILES: CC(=O)Nc1cccc(C#Cc2nn([C@H]3CCN(C(=O)/C=C/CN(C)C)C3)c3ncnc(N)c23)c1] | m/z [M + H]+ 473.2 |
| 7 | 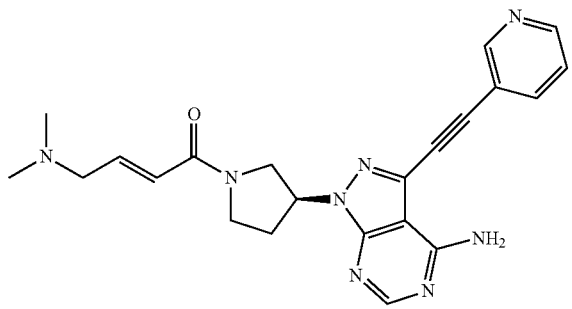 [SMILES: CN(C)C/C=C/C(=O)N1CC[C@H](n2nc(C#Cc3cccnc3)c3c(N)ncnc32)C1] | m/z [M + H]+ 417.2 |

Test Example 1

Measurement of Inhibitory Effect on FGFR2 Kinase Activity

When setting conditions for the measurement of the inhibitory effect of the compounds on FGFR2 kinase activity, FL-Peptide 22 (Caliper Life Sciences, Inc.) was used as a substrate. The purified recombinant human FGFR2 protein used in the test was purchased from Carna Biosciences, Inc.

In the measurement of the inhibitory effect of the compounds, first, a test compound was gradually diluted with dimethylsulfoxide (DMSO) to a concentration that was 20 times higher than the final concentration. Next, the purified human FGFR2 protein, FL-Peptide 22 (final concentration: 1.5 μM), magnesium chloride (final concentration: 5 mM), ATP (final concentration: 75 μM), and the test compound DMSO solution (final concentration of DMSO: 5%) were added to a reaction buffer (15 mM Tris-HCl pH 7.5, 0.01%

Tween-20, 2 mM DTT), and the mixture was incubated at 25° C. for 120 minutes to perform a kinase reaction. EDTA (final concentration: 30 mM) diluted with a separation buffer (Caliper Life Sciences, Inc.) was added thereto to terminate the kinase reaction. Finally, using a LabChip (registered trademark) 3000 system (Caliper Life Sciences, Inc.; excitation wavelength: 488 nm, detection wavelength: 530 nm), phosphorylated peptides and non-phosphorylated peptides were separated, and the amount of each peptide was measured. The level of phosphorylation was determined from the quantitative ratio. The compound concentration at which phosphorylation was inhibited by 50% was defined as the $IC_{50}$ value (nM). Table 21 shows the results.

The results demonstrated that all of the compounds of the present invention, represented by the test compounds, which had a dialkoxy benzene ethynyl group and a partial structure of α,β-unsaturated amide, exhibited a high FGFR2 inhibitory effect. Conversely, the compounds of the Reference Examples, which did not have a dialkoxy benzene ethynyl group or a partial structure of α,β unsaturated amide, showed a remarkably lower FGFR2 inhibitory effect.

TABLE 21

| Test compound | $IC_{50}$ value (nM) |
| --- | --- |
| Ex. Compound 1 | 2.4 |
| Ex. Compound 2 | 1.1 |
| Ex. Compound 5 | 1.1 |
| Ex. Compound 8 | 6.9 |
| Ex. Compound 9 | 1.1 |
| Ex. Compound 10 | 1.2 |
| Ex. Compound 12 | 2.2 |
| Ex. Compound 14 | 3.8 |
| Ex. Compound 15 | 3.0 |
| Ex. Compound 16 | 3.8 |
| Ex. Compound 17 | 4.1 |
| Ex. Compound 18 | 4.3 |
| Ex. Compound 19 | 2.7 |
| Ex. Compound 20 | 3.3 |
| Ex. Compound 22 | 5.6 |
| Ex. Compound 23 | 6.8 |
| Ex. Compound 24 | 7.2 |
| Ex. Compound 28 | 3.7 |
| Ex. Compound 29 | 9.3 |
| Ex. Compound 32 | 0.4 |
| Ex. Compound 38 | 4.7 |
| Ex. Compound 39 | 0.4 |
| Ex. Compound 40 | 3.2 |
| Ex. Compound 42 | 6.6 |
| Ex. Compound 46 | 4.3 |
| Ex. Compound 47 | 2.0 |
| Ex. Compound 48 | 6.8 |
| Ex. Compound 49 | 7.0 |
| Ex. Compound 50 | 5.8 |
| Ex. Compound 51 | <0.3 |
| Ex. Compound 52 | 1.0 |
| Ex. Compound 53 | 0.6 |
| Ex. Compound 55 | 2.5 |
| Ex. Compound 56 | 1.5 |
| Ex. Compound 57 | 1.5 |
| Ex. Compound 59 | 1.2 |
| Ex. Compound 60 | 1.5 |
| Ex. Compound 61 | 2.3 |
| Ex. Compound 63 | 1.0 |
| Ex. Compound 64 | 7.9 |
| Ex. Compound 65 | 7.0 |
| Ex. Compound 66 | <0.3 |
| Ex. Compound 68 | 1.2 |
| Ex. Compound 69 | 8.8 |
| Ex. Compound 73 | 4.9 |
| Ref. Ex. Compound 1 | 280 |
| Ref. Ex. Compound 2 | 270 |
| Ref. Ex. Compound 3 | 190 |
| Ref. Ex. Compound 4 | >10000 |
| Ref. Ex. Compound 5 | 190 |
| Ref. Ex. Compound 6 | 110 |
| Ref. Ex. Compound 7 | 1600 |

Test Example 2

Cell Growth-Inhibitory Effect on Human-Derived Gastric Cancer Cell Line with High Expression of FGFR Human-derived gastric cancer OCUM-2MD3 cells, which overexpressed FGFR2, were subcultured daily in a Dulbecco's modified Eagle's medium (DMEM) containing 10% fetal bovine serum (FBS) at a cell density of not more than 80%. In order to initiate a test of the cell growth-inhibitory effect of the compounds, the OCUM-2MD3 cells were suspended in the above DMEM medium and seeded in a 96-well flat-bottom plate so that each well contained 3,000 cells. Then, the cells were cultured in an incubator containing 5% carbon dioxide gas at 37° C. for one day. On the following day, the test compound was gradually diluted with DMSO to a concentration 100 times higher than the final concentration. The DMSO solution of the test compound was diluted with the medium used for cultivation, and the diluted solution was added to each well of the cell culture plate so that the final concentration of DMSO became 0.5%. Then, the cells were cultured in an incubator containing 5% carbon dioxide gas at 37° C. for 72 hours. The number of cells was measured at the time of the addition of the test compound and 72 hours later after culture by using a Cell Counting Kit-8 (produced by Dojindo Laboratories) according to a protocol recommended by Dojindo Laboratories. The reagent of the kit was added to each plate, and a color reaction was performed in an incubator containing 5% carbon dioxide gas at 37° C. for a predetermined time. After completion of the reaction, the absorbance at a wavelength of 450 nm was measured by a microplate reader. The cell-growth inhibition rate was calculated by the following formula, and the concentration of the test compound at which the cell growth was inhibited by 50% ($GI_{50}$ (nM)) was determined. Table 22 shows the results.

The results demonstrated that all of the compounds of the present invention, represented by the test compounds, showed a high growth inhibitory effect on the human-derived gastric cancer OCUM-2MD3 cell line.

Growth inhibition rate (%)=$(C-T)/(C-C0) \times 100$

T: absorbance of well to which test compound was added
C: absorbance of well to which test compound was not added
C0: absorbance of well measured before addition of compound

TABLE 22

| Test compound | $GI_{50}$ (nM) |
| --- | --- |
| Ex. Compound 2 | <4.6 |
| Ex. Compound 4 | 17 |
| Ex. Compound 8 | 5 |
| Ex. Compound 12 | <4.6 |
| Ex. Compound 15 | <4.6 |
| Ex. Compound 17 | 4.6 |
| Ex. Compound 19 | <4.6 |
| Ex. Compound 24 | 13 |

TABLE 22-continued

| Test compound | $GI_{50}$ (nM) |
| --- | --- |
| Ex. Compound 25 | 13 |
| Ex. Compound 28 | 5 |
| Ex. Compound 29 | 20 |
| Ex. Compound 32 | <4.6 |
| Ex. Compound 39 | <4.6 |
| Ex. Compound 40 | 7 |
| Ex. Compound 64 | 12 |
| Ex. Compound 65 | 13 |
| Ex. Compound 66 | <4.6 |
| Ex. Compound 68 | 8 |
| Ex. Compound 73 | 7 |

Test Example 3

Measurement of Inhibitory Effect on FGFR1 Kinase Activity

When setting conditions for the measurement of the inhibitory effect of the compounds on FGFR1 kinase activity, a biotinylated peptide (biotin-EEPLYWSFPAKKK) was synthesized for use as a substrate by utilizing the amino acid sequence of FL-Peptide 22 (Caliper Life Sciences, Inc.) with biotin. The purified recombinant human FGFR1 protein used in the test was purchased from Carna Biosciences, Inc. In the measurement of the inhibitory effect of the compounds, first, a test compound was gradually diluted with dimethylsulfoxide (DMSO) to a concentration 20 times higher than the final concentration. Next, the purified human FGFR1 protein, substrate peptide (final concentration: 250 nM), magnesium chloride (final concentration: 5 mM), ATP (final concentration: 190 µM), and the test compound DMSO solution (final concentration of DMSO: 5%) were added to a reaction buffer (15 mM Tris-HCl pH 7.5, 0.01% Tween-20, 2 mM DTT), and the mixture was incubated at 25° C. for 120 minutes to perform a kinase reaction. EDTA was added thereto to a final concentration of 40 mM to thereby terminate the reaction. Then, a detection solution containing Eu-labeled anti-phosphorylated tyrosine antibody PT66 (PerkinElmer) and SureLight APC-SA (PerkinElmer) was added, and the resulting mixture was allowed to stand at room temperature for 2 hours or more. Finally, the intensity of fluorescence when excitation light with a wavelength of 337 nm was irradiated was measured by a PHERAstar FS (BMG LABTECH) at two wavelengths of 620 nm and 665 nm. The amount of phosphorylation was determined from the fluorescence intensity ratio of the two wavelengths. The compound concentration at which phosphorylation was inhibited by 50% was defined as the $IC_{50}$ value (nM). Table 23 below shows the results.

Test Example 4

Measurement of Inhibitory Effect on FGFR3 Kinase Activity

The inhibitory effect of the compounds on FGFR3 kinase activity was measured according to the method of Test Example 3. Purified recombinant human FGFR3 protein was purchased from Carna Biosciences, Inc. The final concentration of ATP was 50 µM. Table 23 shows the results.

Test Example 5

Measurement of Inhibitory Effect on FGFR4 Kinase Activity

The inhibitory effect of the compounds on FGFR4 kinase activity was measured according to the method of Test Example 3. Purified recombinant human FGFR4 protein was purchased from Carna Biosciences, Inc. The final concentration of ATP was 200 µM. Table 23 shows the results.

The results of Test Examples 3 to 5 demonstrated that all of the compounds of the present invention, represented by the test compound, showed a high inhibitory effect on FGFR1, FGFR3, and FGFR4, and served as pan-FGFR inhibitors.

TABLE 23

| | $IC_{50}$ value (nM) | | |
| --- | --- | --- | --- |
| Test compound | Test Example 3 | Test Example 4 | Test Example 5 |
| Ex. Compound 2 | 3.6 | 0.5 | 3.4 |
| Ex. Compound 5 | 1.4 | 0.2 | 0.5 |
| Ex. Compound 9 | 3.2 | 0.3 | 4.9 |
| Ex. Compound 47 | 20 | 0.5 | 11 |
| Ex. Compound 51 | 1.2 | 0.1 | 1.7 |
| Ex. Compound 52 | 2.8 | 0.7 | 21 |
| Ex. Compound 62 | 3.1 | 0.7 | 19 |

Test Example 6

Suppression of Increase in Blood Phosphorus Levels and Reduction of Systemic Toxicity by Intermittent Administration Female SD rats (9 weeks after birth) were assigned to six groups so that the average body weight of each group was equivalent. The day in which the grouping (n=3) was conducted was taken as Day 1. The compound of Example 2 was prepared as follows: 15, 30, and 100 mg/kg/day. The compound was orally administered daily, and intermittently administered, from Day 1 (Table 24).

Figure 2:
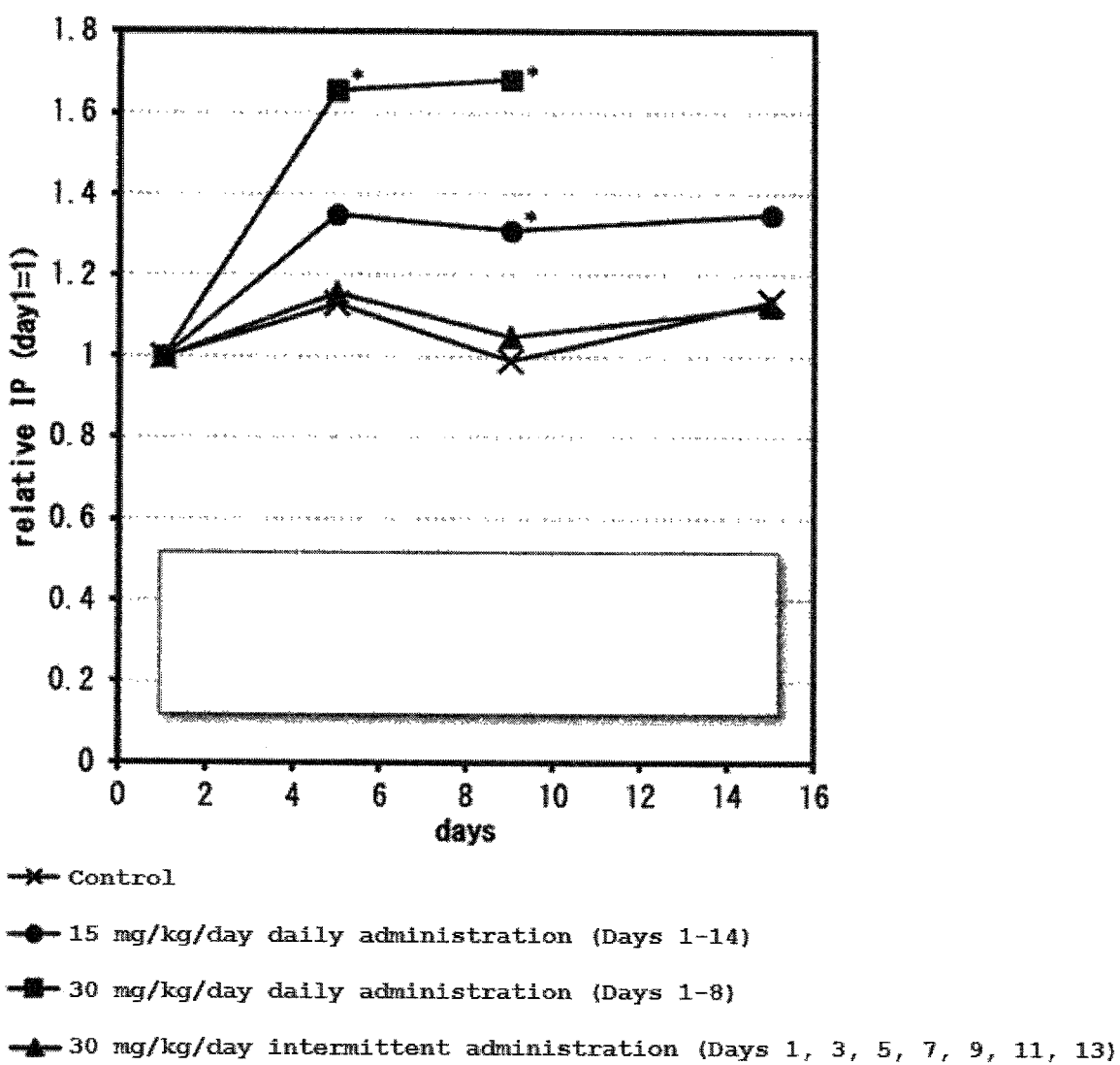
FIG. 2 shows relative phosphorus levels when the blood phosphorus level on Day 1 is taken as 1 in Test Example 6.
Figure 3:
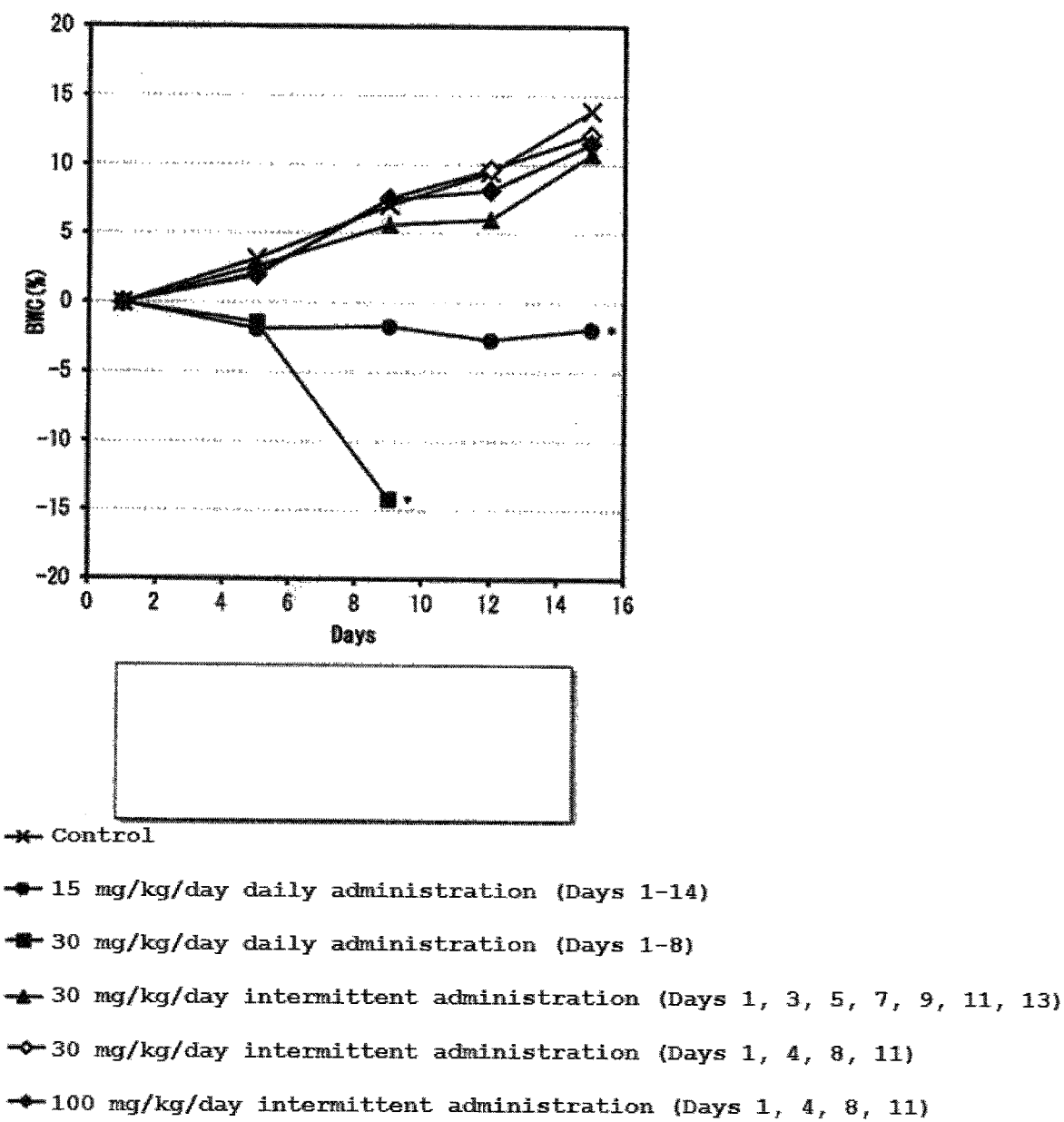
FIG. 3 shows the average weight change [BWC (%)] relative to the body weight on Day 1 in Test Example 6.

Blood sampling (about 100 µL/rat) was conducted in each group on Day 1, Day 5, Day 9, and Day 15, and blood phosphorus levels were measured. Blood sampling on each day was conducted before the administration of the compound on that day. FIG. 1 shows the measurement results of blood phosphorus levels, and FIG. 2 shows relative phosphorus levels when the blood phosphorus level on Day 1 is taken as 1. In FIG. 2, the symbol * indicates that a statistically significant difference (Dunnett's test, $p<0.05$) from the control group was observed on each measurement day. As the index of toxicity during the dosing period, The body weight was sequentially measured, and the average body weight change [BWC (%)] until the last evaluation day relative to the body weight on Day 1 was calculated by the following formula (n: day of body weight measurement performed twice a week; the last measurement day corresponds to Day 15, which is the last evaluation day). FIG. 3 shows the results. The symbol * indicates that a statistically significant difference (Dunnett's test, $p<0.05$) from the control group was observed on the last measurement day of each group.

BWC (%)=[(BW on Day $n$)−(BW on Day 1)]/(BW on Day 1)×100

TABLE 24

| Group | Compound | Dose (mg/kg/day) | Administration schedule | Blood sampling day | Last evaluation day |
|---|---|---|---|---|---|
| 1 | Control | — | — | Days 1, 5, 9, 15 | Day 15 |
| 2 | Ex. Compound 2 | 15 | Daily administration (Days 1-14) | Days 1, 5, 9, 15 | Day 15 |
| 3 | Ex. Compound 2 | 30 | Daily administration (Days 1-8) | Days 1, 5, 9 | Day 9 |
| 4 | Ex. Compound 2 | 30 | Intermittent administration (Days 1, 3, 5, 7, 9, 11, 13) | Days 1, 5, 9, 15 | Day 15 |
| 5 | Ex. Compound 2 | 30 | Intermittent administration (Days 1, 4, 8, 11) | — | Day 15 |
| 6 | Ex. Compound 2 | 100 | Intermittent administration (Days 1, 4, 8, 11) | Day 15 | Day 15 |

Test Example 7

Antitumor Effect of Intermittent Administration Schedule in Rats

Human gastric cancer (OCUM-2MD3) cells were implanted in the right thorax of male nude rats (6 weeks after birth). After implantation of the tumor, the major axis (mm) and minor axis (mm) of the tumor were measured, and the tumor volume (TV) was calculated. Then, the rats were assigned to groups so that the average TV of each group was equivalent. The day in which the grouping (n=5) was conducted was taken as Day 0. The compound of Example 2 was prepared as follows: 3 mg/kg/day, 30 mg/kg/day, and 100 mg/kg/day. The compound was orally administered daily at 3 mg/kg/day, orally administered every other day at 30 mg/kg/day, and orally administered twice a week at 100 mg/kg/day, from Day 1. The evaluation period was set to 14 days, and the last evaluation day was set to Day 15.

Figure 4:
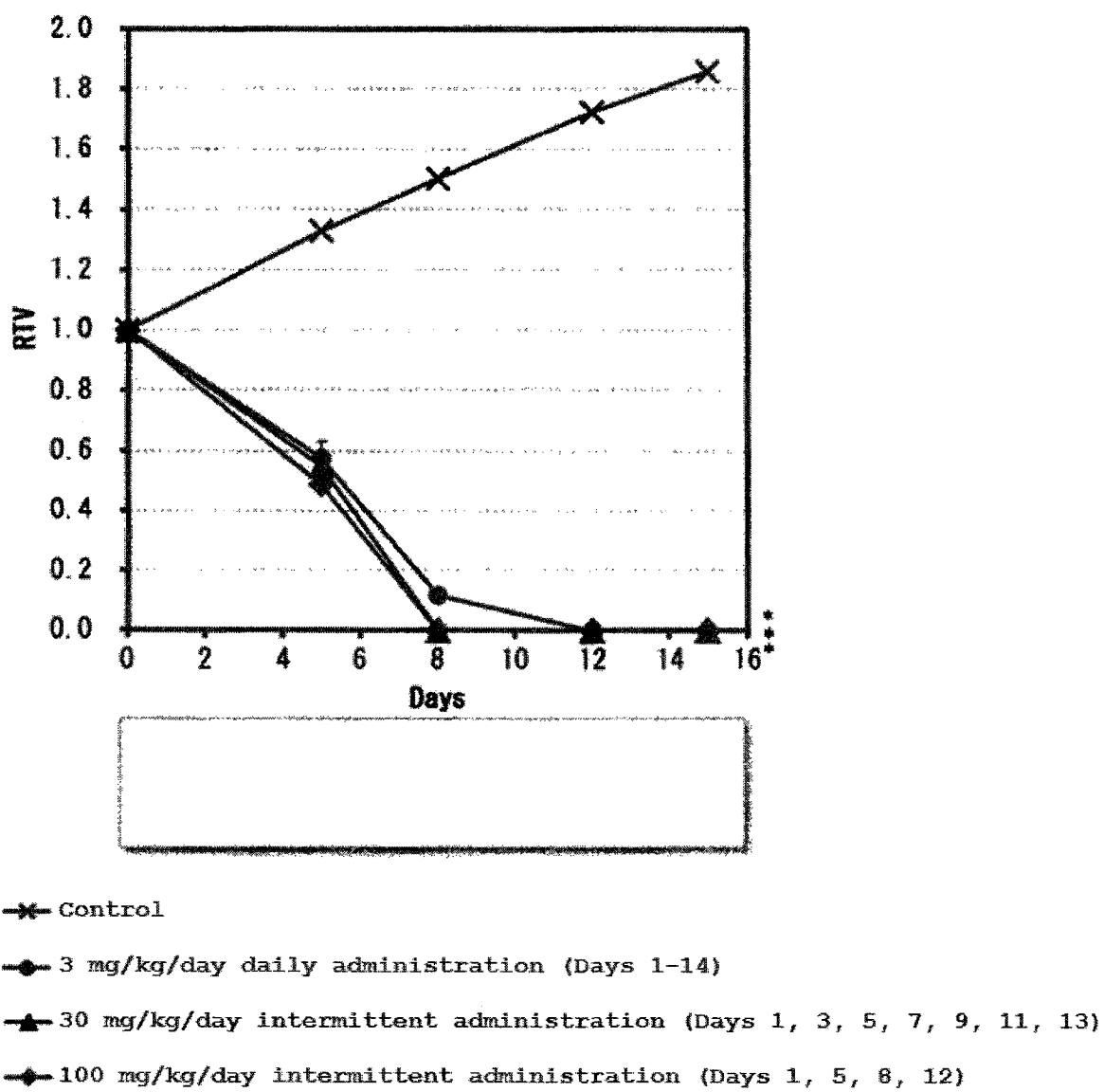
FIG. 4 shows relative tumor volumes with respect to the tumor volume on Day 1 in Test Example 7.

As the index of antitumor effects, TV on Day 15 was measured in each group, and the relative tumor volume (RTV) with respect to TV on Day 0 was calculated by the following formula to evaluate the antitumor effects. The evaluation assessment of effects was as follows: when the average RTV value of the administration group was statistically significantly (Dunnett's test, p<0.05) less than the average RTV value of the control group, it was determined that there were antitumor effects. FIG. 4 shows the results. In the figure, the symbol * indicates that a statistically significant difference from the control group was observed.

$$TV\ (mm^3) = (major\ axis \times minor\ axis^2)/2$$

$$RTV = (TV\ on\ Day\ 15)/(TV\ on\ Day\ 0)$$

Test Example 8

Antitumor Effect of Intermittent Administration Schedule in Mice Human gastric cancer (SNU-16) cells were implanted in the right thorax of male nude mice (6 weeks after birth). After implantation of the tumor, the major axis (mm) and minor axis (mm) of the tumor were measured, and TV was calculated. Then, the mice were assigned to groups so that the average TV of each group was equivalent. The day in which the grouping (n=6) was conducted was taken as Day 0. The compound of Example 2 was prepared as follows: 100 mg/kg/day, 350 mg/kg/day, and 700 mg/kg/day. The compound was orally administered daily at 100 mg/kg/day, orally administered twice a week at 350 mg/kg/day, and orally administered once a week at 700 mg/kg/day, from Day 1. The evaluation period was set to 14 days, and the last evaluation day was set to Day 15.

Figure 5:
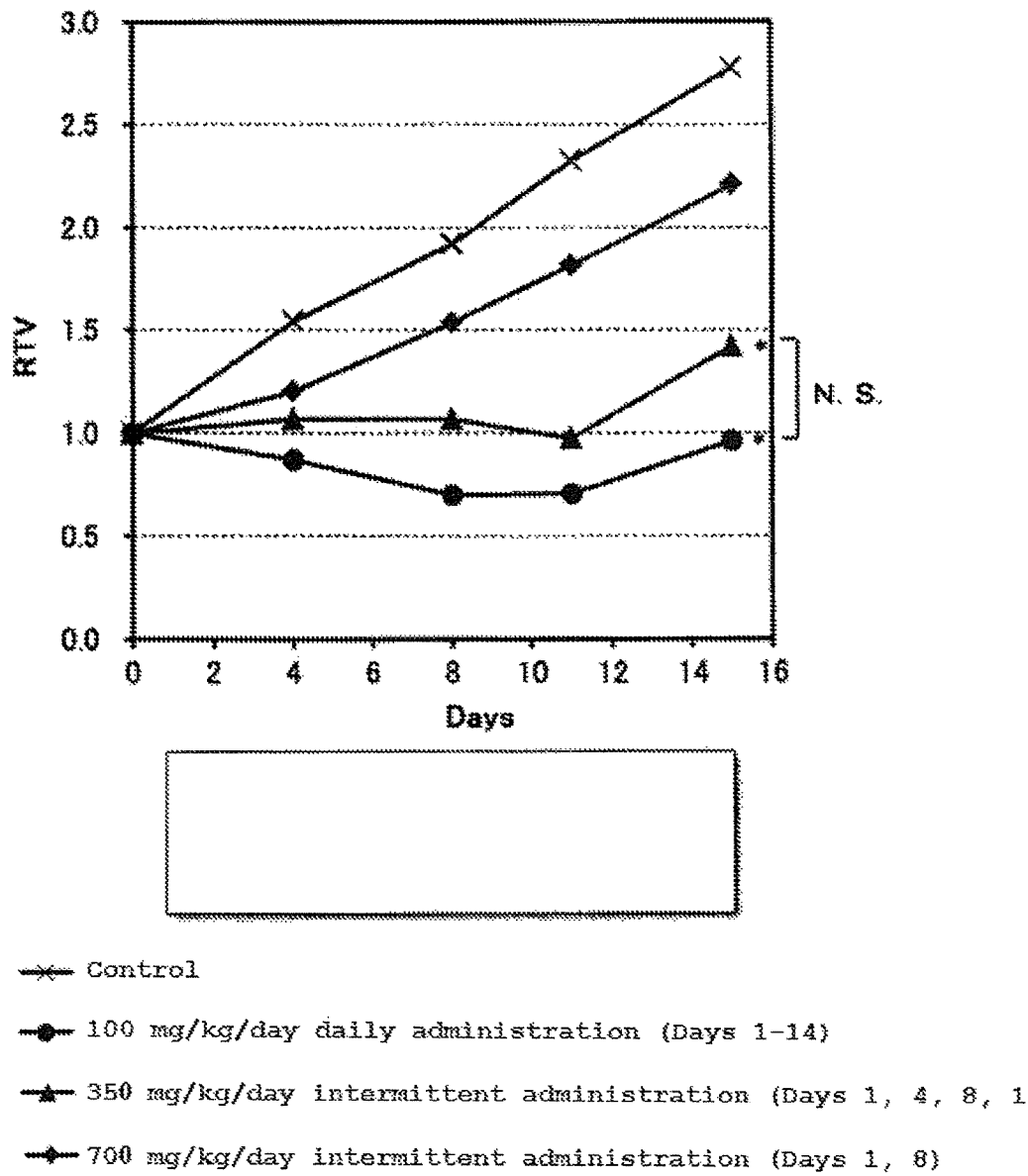
FIG. 5 shows relative tumor volumes with respect to the tumor volume on Day 1 in Test Example 8.

As the index of antitumor effects, TV on Day 15 was measured in each group, and RTV with respect to TV on Day 0 was calculated to evaluate the antitumor effects. The evaluation assessment of effects was as follows: when the average RTV value of the administration group was statistically significantly (Dunnett's test, p<0.05) less than the average RTV value of the control group, it was determined that there were antitumor effects. FIG. 5 shows the results. In the figure, the symbol * indicates that a statistically significant difference from the control group was observed.

Figure 6:
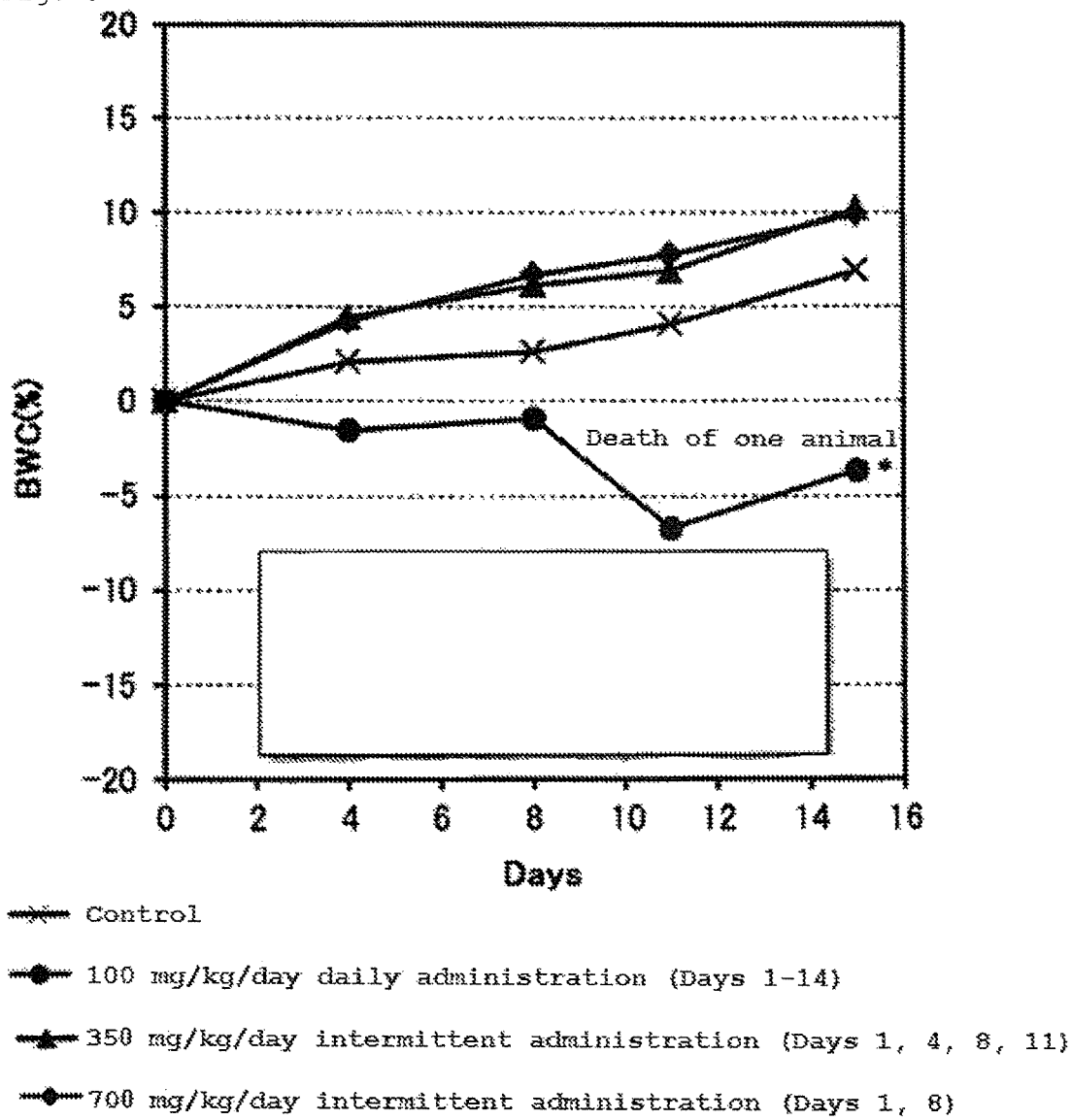
FIG. 6 shows BWC (%) relative to the body weight on Day 1 in Test Example 8.

As the index of toxicity during the dosing period, BW (g) was measured with time, and BWC (%) until the last evaluation day relative to the body weight on Day 0 was calculated. FIG. 6 shows the results. The symbol * indicates that a statistically significant difference (Dunnett's test, p<0.05) from the control group was observed on the last measurement day.

DISCUSSION

As is clear from FIGS. 1 and 2, regarding the blood phosphorus level change after administration of the compound of Example 2, the trough blood phosphorus levels of the 15-mg/kg/day daily administration group and the 30-mg/kg/day daily administration group increased about 1.3 times and 1.7 times, respectively, higher than the blood phosphorus level before initial administration on Day 1. These levels were maintained until the last evaluation day. In contrast, the blood phosphorus levels of the 30-mg/kg/day intermittent administration (alternate-day administration) group were comparable with the blood phosphorus level before initial administration. No increase was observed in trough levels. Although the 100-mg/kg/day intermittent administration group (twice a week) was not measured for the blood phosphorus level before initial administration, the blood phosphorus level on the last evaluation day (Day 15) was equivalent to that of the control group. It was suggested that no increase in trough levels was continued. This demonstrated that a continuous increase in blood phosphorus levels was avoided by intermittent administration, rather than by daily administration.

FIG. 3 shows the body weight changes in this case. As for the influence of compound administration on body weight, body weight gain was suppressed in the 15-mg/kg/day 14-day daily administration group, and body weight loss was observed in the 30-mg/kg/day 8-day daily administration group. On the other hand, body weight gain was observed in all of the intermittent administration groups, similar to the control group. This demonstrated that intermittent administration had less influence on body weight than daily administration.

FIG. 4 shows the antitumor effects of the intermittently administered compound of Example 2 in the rats. The tumor was eliminated in all the animals during the evaluation period in all of the test compound administration groups. It was shown that intermittent administration could exhibit antitumor effects equivalent to those of daily administration.

FIG. 5 shows the antitumor effects of the intermittently administered compound of Example 2 in the mice. Compared with the control group, more significant antitumor effects were observed in the 100-mg/kg/day daily administration group and the 350-mg/kg/day intermittent administration group (twice a week). No significant antitumor effects were observed in the 700-mg/kg/day intermittent administration group (once a week). Further, when the antitumor effects were compared between the 350-mg/kg/day intermittent administration group (twice a week) and the 100-mg/kg/day daily administration group (Student's t-test), no significant difference was observed between the two groups, showing that the antitumor effects of these groups were equivalent.

FIG. 6 shows the body weight changes in this case. As for the influence of compound administration on body weight, body weight loss was observed in the 100-mg/kg/day daily administration group, and one case died. On the other hand, the 350-mg/kg/day intermittent administration group (twice a week) and the 700-mg/kg/day intermittent administration group (once a week) showed body weight changes similar to that of the control group. These results demonstrated that among the intermittent administration groups, the 350-mg/kg/day oral administration group (twice a week) exhibited antitumor effects without suppression of body weight gain.

The above results revealed that by administration at appropriate intervals, such as alternate-day administration or intermittent administration twice a week, the 3,5-disubstituted benzene alkynyl compound represented by Formula (I) and a salt thereof reduced a continuous increase in blood phosphorus levels and suppression of body weight gain, and exhibited antitumor effects similar to those of daily administration. The method for administering a compound having FGFR inhibitory activity is sufficiently expected to become a very useful method that exhibits antitumor effects while avoiding toxicity resulting from FGFR inhibition in clinical treatment.

The invention claimed is:

1. A method of treating a cancer patient, the method comprising
administering a 3,5-disubstituted benzene alkynyl compound or a salt thereof on an administration schedule consisting of at least twice a week and a dosing interval between a day of administration and the next day of administration being at least one day, the 3,5-disubstituted benzene alkynyl compound being represented by Formula (I):

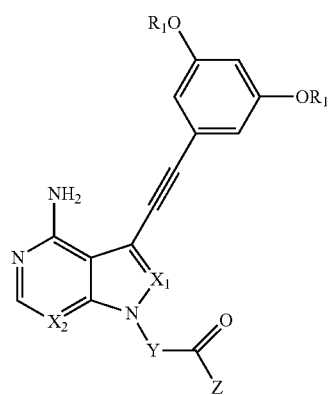

wherein $R_1$ is the same or different, and each represents $C_1$-$C_6$ alkyl;
$X_1$ and $X_2$ independently represent N or CH;
Y is a group represented by Formula (A):

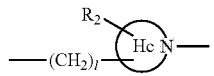

wherein the divalent moiety represented by

is a nitrogen-containing $C_3$-$C_{10}$ heterocycloalkylene group, a group represented by Formula (B):

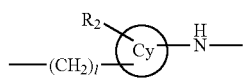

wherein the divalent moiety represented by

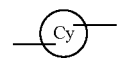

is a $C_3$-$C_{10}$ cycloalkylene group, or a group represented by Formula (C):

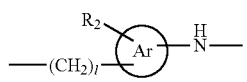

wherein the divalent moiety represented by

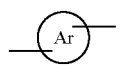

is a $C_6$-$C_{12}$ arylene group;
$R_2$ is hydrogen, $C_2$-$C_6$ alkynyl, —C(=O)$OR_x$, —C(=O)N($R_x$)($R_y$), hydroxy-$C_1$-$C_6$ alkyl, di($C_1$-$C_6$ alkyl)amino-$C_1$-$C_6$ alkyl, or $C_2$-$C_9$ heteroaryl optionally having $R_3$; and $R_3$ is $C_1$-$C_6$ alkyl or di($C_1$-$C_6$ alkyl)amino-$C_1$-$C_6$ alkyl;
Z is —C($R_4$)=C($R_5$)($R_6$) or —C≡C—$R_7$;
$R_4$, $R_5$, and $R_6$ are the same or different, and each represents hydrogen, halogen, $C_1$-$C_6$ alkyl optionally having $R_8$, or a group represented by Formula (D):

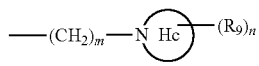

wherein the monovalent moiety represented by

is a nitrogen-containing $C_3$-$C_{10}$ heterocycloalkyl group,
$R_7$ is hydrogen, $C_1$-$C_6$ alkyl, or hydroxy-$C_1$-$C_6$ alkyl;
$R_8$ is —$OR_x$ or —N($R_x$)($R_y$);

$R_9$ is $C_1$-$C_6$ alkyl, halogen, or —$OR_x$;

$R_x$ and $R_y$ are the same or different, and each represents hydrogen, $C_1$-$C_6$ alkyl, $C_3$-$C_{10}$ cycloalkyl, di($C_1$-$C_6$ alkyl)amino-$C_1$-$C_6$ alkyl, or $C_1$-$C_6$ alkoxy-$C_1$-$C_6$ alkyl;

l is an integer of 0 to 3;

m is an integer of 1 to 3; and n is an integer of 0 to 2, wherein said 3,5-disubstituted benzene alkynyl compound is (S)-1-(3-(4-amino-3-((3,5-dimethoxyphenyl)ethynyl)1H-pyrazolo[3,4-d]pyrimidin-1-yl)pyrrolidin-1-yl)prop-2-en-1-one.

2. The method according to claim 1, wherein the administration schedule is based on a 1-week cycle.

3. The method according to claim 1, wherein the administration schedule is based on a 1-week cycle, in which the 3,5-disubstituted benzene alkynyl compound or a salt thereof is administered at least twice and the interval between a day of administration and the next day of administration being one to three days per cycle, and this cycle is performed once or repeated twice or more.

4. The method according to claim 1, wherein the effective amount is 0.05 to 1,000 mg for an oral preparation, 0.01 to 500 mg for an injection, and 1 to 1,000 mg for a suppository.

5. The method according to claim 1, wherein the 3,5-disubstituted benzene alkynyl compound is administered orally.

6. The method according to claim 1, wherein the administering includes administering a pharmaceutical preparation comprising the 3,5-disubstituted benzene alkynyl compound and a pharmaceutical carrier.

7. The method according to claim 1, wherein the administering includes administering a pharmaceutical preparation comprising the 3,5-disubstituted benzene alkynyl compound and a pharmaceutical carrier comprising at least one carrier selected from the group consisting of excipient, binder, disintegrant, lubricant, colorant, solvent, solubilizing agent, suspending agent, isotonizing agent, buffer, and soothing agent.

8. The method according to claim 1, wherein the cancer patient is diagnosed with cancer selected from the group consisting of head and neck cancer, esophagus cancer, colon cancer, rectum cancer, gallbladder cancer, biliary tract cancer, pancreatic cancer, lung cancer, ovarian cancer, cervical cancer, endometrial cancer, renal cancer, bladder cancer, prostate cancer, testicular tumor, osteosarcoma, soft-tissue sarcoma, blood cancer, multiple myeloma, skin cancer, brain tumor, and mesothelioma.

9. The method according to claim 1, wherein the patient is diagnosed with gastric cancer.

10. The method according to claim 1, wherein the patient is diagnosed with liver cancer.

11. The method according to claim 1, wherein the patient is diagnosed with cholangiocarcinoma.

12. The method according to claim 1, wherein the patient is diagnosed with breast cancer.

13. The method according to claim 1, wherein the 3,5-disubstituted benzene alkynyl compound is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one;

the effective amount is 0.05 to 1,000 mg;

the 3,5-disubstituted benzene alkynyl compound is administered orally; and the cancer patient is diagnosed with gastric cancer.

14. The method according to claim 1, wherein the 3,5-disubstituted benzene alkynyl compound is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one;

the effective amount is 0.05 to 1,000 mg;

the 3,5-disubstituted benzene alkynyl compound is administered orally; and the cancer patient is diagnosed with liver cancer.

15. The method according to claim 1, wherein the 3,5-disubstituted benzene alkynyl compound is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one;

the effective amount is 0.05 to 1,000 mg;

the 3,5-disubstituted benzene alkynyl compound is administered orally; and the cancer patient is diagnosed with cholangiocarcinoma.

16. The method according to claim 1, wherein the 3,5-disubstituted benzene alkynyl compound is (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one;

the effective amount is 0.05 to 1,000 mg;

the 3,5-disubstituted benzene alkynyl compound is administered orally; and the cancer patient is diagnosed with breast cancer.

17. A method of suppressing weight loss during treatment with a 3,5-disubstituted benzene alkynyl compound in a cancer patient, comprising administering a pharmaceutical composition comprising (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one to the cancer patient on an administration schedule consisting of at least twice a week with an interval of at least one day.

18. A method of suppressing blood phosphorus level increase during treatment with a 3,5-disubstituted benzene alkynyl compound in a cancer patient, comprising administering a pharmaceutical composition comprising (S)-1-(3-(4-amino-3-((3,5-dimethoxyphenyl)ethynyl)-1H-pyrazolo[3,4-d]pyrimidin-1-yl)pyrrolidin-1-yl)prop-2-en-1-one to the cancer patient on an administration schedule consisting of at least twice a week with an interval of at least one day.

* * * * *